US011202420B2

(12) United States Patent
Vriezen et al.

(10) Patent No.: US 11,202,420 B2
(45) Date of Patent: *Dec. 21, 2021

(54) PLANTS WITH AN INTENSE FRUIT PHENOTYPE

(71) Applicant: NUNHEMS B.V., Nunhem (NL)

(72) Inventors: Willem Hendrik Vriezen, Haelen (NL); Henricus Maria Verbakel, Boekel (NL); Franco Vecchio, Fidenza (IT)

(73) Assignee: NUNHEMS B.V., Nunhem (NL)

( * ) Notice: Subject to any disclaimer, the term of this patent is extended or adjusted under 35 U.S.C. 154(b) by 149 days.

This patent is subject to a terminal disclaimer.

(21) Appl. No.: 16/041,344

(22) Filed: Jul. 20, 2018

(65) Prior Publication Data

US 2019/0014732 A1 Jan. 17, 2019

Related U.S. Application Data

(63) Continuation of application No. 15/022,895, filed as application No. PCT/EP2014/069863 on Sep. 18, 2014, now Pat. No. 10,212,898.

(30) Foreign Application Priority Data

Sep. 18, 2013 (EP) ..................................... 13184924

(51) Int. Cl.
*A01H 5/08* (2018.01)
*A01H 1/06* (2006.01)
*C12Q 1/6895* (2018.01)
*C07K 14/415* (2006.01)
*A01H 1/02* (2006.01)
*A01H 1/04* (2006.01)

(52) U.S. Cl.
CPC ............... *A01H 5/08* (2013.01); *A01H 1/02* (2013.01); *A01H 1/04* (2013.01); *A01H 1/06* (2013.01); *C07K 14/415* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| 7,179,957 | B1 * | 2/2007 | Zhao ................... C07K 14/415 800/285 |
| 10,212,898 | B2 * | 2/2019 | Vriezen ............... C07K 14/415 |

FOREIGN PATENT DOCUMENTS

| WO | 2008092505 A1 | 8/2008 |
| WO | WO 2013/135726 A1 * | 3/2012 |
| WO | 2013135726 A1 | 9/2013 |
| WO | 2016113329 A1 | 7/2016 |

OTHER PUBLICATIONS

Asaf A. Salamov et al., "Ab initio Gene Finding in *Drosophila* Genomic DNA", Genome Research, 2000, vol. 10, pp. 516-522.
Audrey Darrigues et al., "Tomato Analyzer-color Test: A New Tool for Efficient Digital Phenotyping," J. Americ. Soc. Hort. Sci, 2008, vol. 133, No. 4, pp. 579-586.
Bradley J. Till et al., "A protocol for TILLING and Ecotilling in plants and animals," Nature Protocols, 2006, vol. 1, No. 5, pp. 2465-2477.
Bradley J. Till et al., "Discovery of chemically induced mutations in rice by TILLING," BMC Plant Biology, BMC Plant Biology, 2007, vol. 7, No. 19, pp. 1-12.
Bradley J. Till et al., "Discovery of induced point mutations in maize genes by TILLING," BMC Plant Biology, 2004, vol. 4, No. 12, pp. 1-8.
Bradley J. Till et al., "High-Throughput TILLING for *Arabidopsis*," Methods in Molecular Biology, 2006, vol. 323, pp. 127-135.
Bruno Gobin et al. "Rassenproef Tomaat Vor Verwerking in Tunnel," http://www.pcgroenteteelt.be/Portals/0/Documents/Publicaties/Jaarverslag/2012/Rassenproef%20tomaat (English abstract), Sep. 2013, pp. 1-7.
Charles H. Leesberg et al., "Interaction study of MADS-domain proteins in tomato," Journal of Experimental Botany, 2008, vol. 59, No. 8, pp. 2253-2265.
Diana Rigola et al., "High-Throughput Detection of Induced Mutations and Natural Variation Using KeyPoingTM Technology", PLOS One, Mar. 2009, vol. 4, No. 3, e4761, pp. 1-9.
Erik J. Sacks et al., "Genetic and Environmental Variation for Tomato Flesh Color in a Population of Modern Breeding Lines," J. Amer. Soc. Hort. Sci., 2001, vol. 126, No. 2, pp. 221-226.
Gang Fang et al., "Getting started in Gene Orthology and Functional Analysis," PLOS, 2010, vol. 6, No. 3, e1000703, pp. 1-8.
GenBank Accession No. XM_004241858, version XM_004241858.1 GI: 460392604, as given by NCBI on ncbi.nlm.nih.gov/nuccore/XM_004241858.1, updated Mar. 12, 2013.
GenBank Accession No. XP_004241906, PREDICTED: Agamous-like MADS-box Protein AGL11-like [Solanum lycopersicum], Mar. 12, 2013.
Gill Ronen et al., "An Alternative Pathway to •-carotene Formation in Plant Chromoplasts Discovered by Map-based Cloning of Beta and Old-gold Color Mutations in Tomato," PNAS 2000, vol. 97, No. 20, pp. 11102-11107.
International Search Report and Written Opinion issued in International Patent Application No. PCT/EP2014/069863 dated Dec. 11, 2014.

(Continued)

*Primary Examiner* — Bratislav Stankovic
(74) *Attorney, Agent, or Firm* — Arent Fox LLP

(57) ABSTRACT

The present invention relates to plants comprising a modified amount, activity or function of AGL11-like protein, wherein the plant is a member of plant family Cucurbitaceae or of species *Solanum lycopersicum*; characterized in that the plant is not a *Solanum lycopersicum* plant having a deletion from nucleotide 1042 to nucleotide 637 upstream of the ATG start codon of SEQ ID NO: 1.

17 Claims, 7 Drawing Sheets

Figure 1:

Specification includes a Sequence Listing.

(56) References Cited

OTHER PUBLICATIONS

Lena C. Hileman et al., "Molecular and Phylogenetic Analyses of the MADS-Box Gene Family in Tomato," Mol. Biol. Evol., 2006, vol. 23, No. 11, pp. 2245-2258.
Lincoln D. Stein et al., "The Generic Genome Browser: A Building Block for a Model Organism System Database", Genome Research, 2002, vol. 12, pp. 1599-1610.
Lucas Comai et al., "Efficient discovery of DNA polymorphisms in natural populations by Ecotilling," The Plant Journal, 2004, vol. 37, pp. 778-786.
Lucie Parenicova et al., "Molecular and Phylogenetic Analyses of the Complete MADS-Box Transcription Factor Family in *Arabidopsis*: New Openings to the MADS World," The Plant Cell, Jul. 2003, vol. 15, pp. 1538-1551.
Maarten G. Verlaan et al., Chromosomal rearrangements between tomato and Solanum chilense hamper mapping and breeding of the TYLCV resistance gene Ty-1, The Plant Journal, 2011, vol. 68, pp. 1093-1103.
Naruya Saitou et al., "The Neighbor-joining Method: A New Method for Reconstructing Phylogenetic Trees," Mol. Biol. Evol., 1987, vol. 4, No. 4, pp. 406-425.
Nunhems, "Catálogo de variedades, Tomates Híbridos" http://nunhems.mx/www/NunhemsInternet.nsf/CropData/MX_ES_TOF/$file/TOF_MX_ES_2010.pdf, 2010, pp. 1-6.
Paul Shore et al., "The MADS-box family of transcription factors," Eur. J. Biochem., 1995, vol. 229, pp. 1-13.
Ramu Chenna et al., "Multiple sequence alignment with the Clustal series of programs," Nucleic Acids Research, 2003, vol. 31, No. 13, pp. 3497-3500.
Stephan F. Altschul et al., "Basic Local Alignment Search Tool," J. Mol. Biol., 1990, vol. 215, pp. 403-410.
Steven Henikoff et al., "TILLING. Traditional Mutagenesis Meets Functional Genomics," Plant Physiology, Jun. 2004, vol. 135, pp. 630-636.
Steven Henikoff et al.,"Amino acid substitution matrices from protein blocks," PNAS, 1992, 89, pp. 10915-10919.
Tomato Tilling,"http://tilling.ucdavis.edu/index.php/Tomato_Tilling," last accessed Jul. 29, 2015, pp. 1-3.
Victoria María Busi et al., "MADS-box Expressed During Tomato Seed and Fruit Development," Plant Molecular Biology 2003, vol. 52, pp. 801-815.
Yuling Bai et al. "QTLs for Tomato Powdery Mildew Resistance (*Oidium lycopersici*) in Lycopersicon parviflorum G1.1601 Co-localize with Two Qualitive Powdery Mildew Resistance Genes," MPMI, 2003, vol. 16, No. 2, pp. 169-176.
Yuling Bai et al., "Tomato Defense to Oidium Neolycopersici: Dominant Ol Genes Confer Isolate-Dependent Resistance Via a Different Mechanism than Recessive ol-2," MPMI 2005, vol. 18, No. 4, pp. 354-362.
Busi et al (2003, "MADS-Box Genes Expressed during Tomato See and Fruit Development". Plant Molecular Biology 552:801-815).
Busi et al (2003, NCBI Accession No. AY098736).
Busi et al (2003, Plant Molecular Biology 52:801-815).
Mejia et al (2011, BMC Plant Biology 11:57; http://www.biomedcentral.com/1471-2229/11/57).
Ronen et al (2000, PNAS 97(20): 11102-11107).

* cited by examiner

Figure 2

```
                            20                   40
M3          M---------  ----------  ------FQNQ  EEKMS-----  -DSPQRKMGR  19
C3          MSKHYQSPLT  RMIKEEGKGK  LQIKGMFQNQ  EEKMS-----  -DSPQRKMGR  44
M4          M--------S  ----------  -----CYEEE  DEESGVVGLR  KSSSSSRTGR  27
C4          MFCRKRKKMS  ----------  -----CYEEE  DEESGVVGLR  RSSSSSRTGR  35
M1          M---------  ----------  ----------  ----------  --------GR  3
C1          M---------  ----------  ----------  ----------  --------GR  3
M2          M---------  ----------  ----------  ----------  --------GR  3
C2          M---------  ----------  ----------  ----------  --------GR  3
TAGL11-like MMILC-----  ----------  ----------  ----------  -------MGR  8
Consensus   M.........  RMIKEEGKGK  LQIKG.....  .E...VVGLR  ...S.....GR 60                  80                  100
GKIEIKRIEN  TTNRQVTFCK  RRNGLLKKAY  ELSVLCDAEV  ALIVFSSRGR  69
GKIEIKRIEN  TTNRQVTFCK  RRNGLLKKAY  ELSVLCDAEV  ALIVFSSRGR  94
GKIEIKRIEN  TTNRQVTFCK  RRNGLLKKAY  ELSVLCDAEV  ALIVFSSRGR  77
GKIEIKRIEN  TTNRQVTFCK  RRNGLLKKAY  ELSVLCDAEV  ALIVFSSRGR  85
GKIEIKRIEN  TTNRQVTFCK  RRNGLLKKAY  ELSVLCDAEV  ALIVFSTRGR  53
GKIEIKRIEN  TTNRQVTFCK  RRNGLLKKAY  ELSVLCDAEV  ALIVFSTRGR  53
GKIEIKRIEN  TTNRQVTFCK  RRNGLLKKAY  ELSVLCDAEV  ALIVFSTRGR  53
GKIEIKRIEN  TTNRQVTFCK  RRNGLLKKAY  ELSVLCDAEV  ALIVFSSRGR  53
GKIEIKRIEN  NTNRQVTFCK  RRNGLLKKAY  ELSVLCEAEI  ALIVFSTRGR  58
GKIEIKRIEN  .TNRQVTFCK  RRNGLLKKAY  ELSVLC.AE.  ALIVFS.RGR 120                 140
LYEYANNSVK  ATIDRYKKAS  SDSSNTG-ST  SEANTQFYQQ  EAAKLRVQIG  118
LYEYANNSVK  ATIDRYKKAS  SDSSNTG-ST  SEANTQFYQQ  EAAKLRVQIG  143
LYEYANNSVR  ATISRYKKAY  SDPSTAM-SV  SEANTQFYQQ  ESAKLRAQIG  126
LYEYANNSVR  ATISRYKKAY  SDPSTAM-TV  SEANTQFYQQ  ESAKLRAQIG  134
LYEYANNSVR  GTIERYKKAF  ADSSNSGLSV  AEANVQFYQQ  EATKLKRQIR  103
LYEYANNSVR  GTIERYKKAF  ADSSNSGLSV  AEANVQFYQQ  EATKLKRQIR  103
LYEYSNNSIK  TTIERYKKAC  SDSSATS-SV  TELNTQYYQQ  ESAKLRQQIQ  102
LYEYSNNSIK  TTIERYKKAC  SDSSATS-SV  TELNTQYYQQ  ESAKLRQQIQ  102
VYEYSNNNIK  ATIERYKKAT  AETSNAC-TT  QELNAQFYQQ  ESKKLRQQIQ  107
.YEY.NN...  .TI.RYKKA.  ...S...L..  .E.N.Q.YQQ  E..KL..QI.

160                 180                 200
NLQNSN----  RNMLGESLSS  LTAKDLKGLE  TKLEKGISRI  RSKKNELLFA  164
NLQNSN----  RNMLGESLSS  LTAKDLKGLE  TKLEKGISRI  RSKKNELLFA  189
NLRNLN----  RHLLGESISS  LSVKDLKSLE  VKLEKGLSRI  RSRKNELLFS  172
NLQNLN----  RHLLGESISS  LSVKDLKSLE  VKLEKGISRI  RSRKNELLFS  180
EIQNSN----  RHILGEALSS  LPLKELKSLE  GRLERGISKV  RAKKNETLFA  149
EIQNSN----  RHILGEALSS  LPLKELKSLE  GRLERGISKV  RAKKNETLFA  149
MLQNSNSNLV  RHLMGDSLSA  LTVKELKQLE  NRLERGITRI  RSKKHEMLLA  152
MLQNSN----  RHLMGDSLSA  LTVKELKQLE  NRLERGITRI  RSKKHEMLLA  148
MMQNSN----  RHLVGEGLSC  LNVRELKQLE  NRLERGISRI  RSKKHEMILA  153
...N.NSNLV  R...G...S.  L....LK.LE  ..LE.G....  R..K.E....

220                 240
EIEYMRRREI  DLHNNNQMLR  AKIAESER--  -NVNM-----  ----------  196
EIEYMRKREI  DLHNNNQMLR  AKIAESER--  -NVNM-----  ----------  221
EIEYMQKREI  ELHTNNQLIR  AKIAETERSQ  QNRNASNNGI  AATGGRGDEG  222
```

Figure 2 (continued)

```
EIEYMQKREI ELHTNNQLIR AKIAETERSQ QNTNASNNNG IATR-RGEEG  229
EMEFMQKREV ELQSHNNYLR AQIAEHERIQ QQQQQQQQTN MMQRATYE--  197
EMEFMQKREM ELQSHNNYLR AQIAEHERIQ QQQQQQQQTN MMQRATYE--  197
EIEYLQKREI ELENENVCIR TKIAEVERVQ QANM------ ----------  186
EIEYLQKREI ELENENVCIR TKIAEVERVQ QANM------ ----------  182
ETENLQKREI LLEQENAFLR SKIAENERLQ ELSMMP---- ----------  189
E.E....RE. .L...N...R ..IAE.ER.Q .......... ........EG 260        280        300
-MGGEFELMQ SH-PYDPRDF FQVNGLQHNH QY-------P RQDNMALQLV *  238
-MGGEFELMQ SH-PYDPRDF FQVNGLQHNH QY-------P RQDNMALQLV -  262
SMATNLEVNN HHHQYDSTNY FDPH---HNH P--------- ----ISLQLV *  257
SMGTNLEDNN HH-QYDSTNY FDPH---HNH P--------- ----ISLQLV -  262
SVGGQYD-DE NRSTYGAVGA LMDS---DSH YA-------P QDHLTALQLV *  237
SVGGQYD-DE NRSTYGAVGA LMDS---DSH YA-------P QDHLTALQLV -  236
AVSGQ-ELNA IQALANSRNF FSPNIMETAG PVSFS----- HQDKKMLHLG *  231
-VSGQ-ELNA IQALANSRNF FSPNIMEPAG PVSYS----- HQDKKMLHLG -  225
AAGGQ-DYSA IQQYL-ARNM LQLNMMEGQG VSSYDPLPPP HHDKKSLEL- Q  237
.......... .......... .......... ..S..PLPPP ......L.L.
```

Figure 3

TGTTGAATGATGGAATGAAATACAAACTTACAAAATTTTTATTATTTTCTACTTTCAGAAATCATTTTTTTATTTTTATTTTT
ACAAGAAAAGCCATTCTTTATTGTTAAATTATCTTCCTTTTTTGAAAAAAAAGATATTGACCAATTTAACATTAAAATTACAGAA
AAACACAATCATCTTGCCATAATACAATTCCATAATTCTGTCTTAATTAACTATAAATCACCTCACTCAATTCTATCTGGAACTC
AACAAATCAACCCTAACTTTCATTTCAACGTGCGGTTTCACAAAACCCTAAAAAAGTTAAATCTTCACTTTATCTATCAATTGAC
ACTCCATAACGGATTTAGAATTTTAATTCCATGAGTTAAGCATTTCTAGATGTTTAGTATTGAGTCAATTATATGTTTGAAGTTA
TAATTCATGTAACTTTGCCTATGAATTTATGCTTCATCAGAAGTTATGATTTCAATTAAACTTGTATCCTTCCCTATAGATATGA
TATGAATTTATATCATCGAGTTAAATTACTTCAAGTTTGACGGAAATATTATTCTTAAATTTCAAACAAGTTGATATTGATTATA
TGAATTTTTACCATGAATTCAGAAGTAGAATTAATATCTATGTTTTTCTTAATTAAACAAAATTAGAGCCCGTTTGAATAGGTTT
AGTAGTCGGTCAAACCTACTTTTAAATCAATTTTTTGACTTCTGAAAGTGTTAGGCAAATATAAAAAGTAACTAAAATAAGTTACG
AAGTGTCTGACAAAGTAAAAAATGACTCAAAACAAATAAAAAATGATTTAAAATAAGTCAAAAACCAAAAGTAGATCCCCTATTA
CTTTTTATTT TTTGACTTAA AAGTCATTTC ATTTTGATTT TTTATTTTTA ATTTAAAA [**start deletion
causing** *intense* phenotype in *Sol lycopersicum*] <u>**GC TATTTTTTTA AGCCAATCCA GACGGTCTCT
TAATATACAG GTCAAACCTC ATTAAATAAA ATTTAAATAT TTGAAAGAAA AGTTTGAGAG ATTTTAAACA
GCACAAGGGG CATATTAGTC AAGAAGAAAC AAAAATAACA CGCTTTGCAA TAATTGGTGA AATTTTAGTC
TGCAATAAAC AATCCCATAA CATCACGTCT GGTTTATATC TGGAAAAAAG CCATTTGAAT GTCATTTTCT
TGGCCAGCCA TCTCTATTAT CTCTCTTCAC TTTAATTTTG AGTGATACTT TCTTCGTCCA TCCGACTCAA
CACACATCTT TTAAGAAATA ATAAATTCGA AGAGTAATTT TATTATATAT CATCAGTCAC CCCTATTGGT
AACACGTCAT CTAAATATTA AAA**</u> [end deletion] AGTAAAT AAAATGGTAA AACATCTCTT GTGTTTTTCA
AATTGAATAA TTATTTTTAG TATAGTAAAC AAGTAAAAAT AGTCGTAGCT AGGGATAAAG TTAGGGTAAG
TAGGGATATA ATATAAAAAG AAAGAAAAGC ATATAAGTAT TATGTTTTTT CTTCATTGAT CAGTGTACAA
ATAAGAAGTC TTTGGAAGTT GTGTGAGTTT TCAGAAAGCC TTTGAAGTTC GCCGGAAAAT AGCAATATTT
TCAATTCAAG CCAATCAGGT CTATTACGTT GATATTTTAC ATAGCATCAA ATTTTAGAAA GAAAAAAATA
TATGAAAAAA CTTAAATTTC CCATTCTTCC ATGCATTTTT TAAATTTTTT TTTTTTGCA GATTCTGAAA TGT
[Start 5'UTR mRNA] TTCTCTC TGTGTTCATT ATGACAAAAT TAATTTGTGT TTCGTGTGGA ACTAAGTCAA
GCTTTAGATC TATCTGCAAA TTACATAGGT TATAGAAATA TGAAAGATTT CATTTTTATA TCTATCAAGC
GCGTGCATTT TTTTTTTCTT TTAATCTTTC ACTTATTTGA AAGGGAAGGG TGCTTACTAT CTGAGTAACC
TCCTCTTGTC ACGGAAATTT TGGTTGATCA ATAAAAGATC TCCTTGAAAC [Exon 1] <u>ATGATGATCTTGTGT</u>
[Intron 1] GTAAGTTATGTTTACACAAGATTTTTTTTAATTTGTGTGTATCTTTTCTTGCATATCATGAGGAGAAAA
AAAAGGAATTGGAAAAACATTTGTACTACTTTTTTATTATATTTGGAGGTAGCTTCTCCCAAGAAAATAAAAATTTAATTCTTCA
AATACTAATTAATTTGGATGATTATGTGAGTTATTATTGCTTAAATTCTTGTATTGGATGGTTGTTTTTTTTTAGTGATAGAGA
GATTTTAGAATCATTTCTCAAATCTCTTGTTTTAAATTTCTTCTTTGTTTAATCTCTTTGAATACTTAGTTCTACACATGCACGA
CTTTTAATATGAGGTGTTTTAGAGATACATATAACAATTTTACCAGTCGTTTTTAATAATACTACTTTTTTTTTTTAAAAAAAAA
AAGACAGTCTAATTTGGAGCAATTCTCCAAGAAAGAACTAGTTTAAAACATTGATTTTGTATTATAAATTTATTTTACTTCATCA
TCAAACATGGAGTTACTTCTGCTTCATCTTTCGTTTATTTAGTTAGACCTAACTACCTCTTCAATTTCTACTGAATGGAAGAAAA
AAAATGATATAAGTTATTGCTTAGATTCTTGTATTGAAAGCGTTTTCATAAATTTAATCGAAACTTTAAAATTTTTTATAGAAGA
TGAATTGAAGAATCAATTTTTGGATTTCTTTTTGGAGTATAAGCGAAATTTATCCGAAAAACTGATTTGGGCAAATTTTTGGAGT
TAGATTTTTTTTTTGAAGATGGTAAATTTTCAAGAAAAGAAAAGAAAAAAACAAATCTCATGAAGAAACGGTATTTTAATTTTT
TTAGAAAAATCTATGATCGAACCAGAGCTAATTAGTTCATAGATTTCTTGTTCTAGATTTCTACTAATTTTTCTCTTGTTATAG
AATGAGATATGTCCGATTTATTCATTACTCTCAAAATTAAAACATAGGTATTAATTAATTAAATATAAATGTGTTATATTCTCTT
TTATGTGGTTAATACAG [Exon 2] **ATGGGAAGAGGAAAGATAGAGATAAAGAGGATAGAGAACAACACAAA
CAGGCAGGTTACATTTTGCAAGAGAAGAAATGGATTGTTGAAGAAAGCCTATGAACTCTCTGTTCTATGTGAAGCTGAGATTGCT
CTTATTGTTTTCTCCACACGTGGACGCGTCTATGAATACTCTAACAACAA** [Intron 2] GTAATTTCTTATTTA
TCTCTCATATAGTTAAATTTGTTCAATTAGACGATCATATATATCGTTATATAACATATAATATATGGACATAAATATGGCATTTC
ATTAGCATCTACTTCTTTCTTGATATCATAATCATTCGCTTATCTCTTGATGTTTGAAATCTGAATAATCATTTTGTTAGTGCAT
AAAATAATTGAGCTGTAAGAAAGCATATATGAATACACTGTTCCTCAAAATTTATAGTAGTTGTTTGATTCACACACAAATGACA

Figure 3 (continued)

```
GAATCGGAGGTGGAGGATACTTACAATCAACTCTTCTCGTCTTTAATTGTGTTTGAGTTATATGTAAAAAATATTATCATAAAAG
GATTTACATATAATAATCTAGATAAATAATACTATGAAAGGTTTGAGGATAGATAACATAATCAATATAGAATGTTATTTGTGAA
ACTTATTGTCCTTACTTTCACTAGAAAATTAGTCTATTTTTCTCAATTTTAAGAAATTTGTTTTTTTTTTGAAAAAAAATTAT
TCTAAAATTTTGGCTAACCAAATGGAGAAGATAAAAAAAAAAAAGTAAAATAGAAAATATTTTCCCCCATATCGAAAATATCCT
ATATATCCAACACCGTACCTAAGTCACAAAAGATCAATAAGAAAAGTGATCTTGAGCCTAACTTTATCTTCGAAGGTTTGCTTAT
GAGGTAAAAATTATAATAAGAAAAGTGATTTGAGGCATAATTAACTCTACTTCAAAACTTAGTTCATGAGGTAAAAACTATCCAA
AATCATATACCAACACACATCCGTCATTAACCATCAATATGACATACTAATATTTTTCCTACAATTACTCCTCTCAACTAAAGCC
TGAACAATATAATATAAAGATCCAACGTCAAAATAAGTTAAGAAATGAGATGAATATAAATTTACTATCTCTTAATCACAATTAA
AAAAAGGAAGGCATTCTCAGGTGATATCGAATAATAGTACACTAGTGTTTTAGGAGATGTTCACACATATAGTTTAACTTAGTTG
AATCTCTACCCAATCCTCGAGCCCTCTGTCGAAGCTTAGTTAATAATTCAATCTCAATTGCTAGTTCATGAGAATGAGATCTGCC
AAAAGTTAAACCATCTTAGAAGATTAATAATTGCCACTTTGTTTTGAATTTTGAATAACACAAATTTTTCTTTTAAAAAAAAAAA
AATATTAATAAAAAAAATTTGCCACATCCATCACCAGCCTGTGAAATAATTAAAGTGAAATGAAATATCCTCTCGCGATAAACTT
TTACATGAGATGATTTATACTTCAATATAATTATAGTATAATAGTACCAAAGCTATAGGTATAAGTCTTGAGTTTGAATCGTACA
GTAACTAACTCATCATCATCAATTAAAAACGAATTTTTCACGTGCTTGGCCGTACATATTCTCTCTCTAACTTCTTTAAATTCTT
AAATAAGATGGTTTATGCACTTCAAACAACTATGATAATTACCTTGAAAGATCCATGTGTGAGTATATATATATATATATATGCA
AGAAAAGTGAATGAGTGACAAATAATATTTATTGGTTTTATACATGAAAAAGTGTCAAGGACACTCCAGATTAATAAGTACTAAA
AGAAGTATATATTGAGAAGTCCCATCATGAGTGACTTGTGACTATTGTGTTCTGCTGTTATGAGGGCCTTTTGTTTCCTCTTGT
AGCTTATGCATTATAAAGTTCTCCTGCTTTGGTTTGTATCTATTCTAGTTCTAGTCAATATATGTTCTCTCTTTCACTTTTATGT
CTACATATATTAATTAATTAAAAAGTACTTCTCCCATATATAAGGTCTCCCTATTGCATGCATATGGAATATTAAAAAAAAATA
AAAAAGTACATATTATTATCACCCTAAAATGTAAAAAAGATATGATTCCAAAGATAGTGCAACATAAAAGGAGAGAAGAGAAAT
CTTCAAAAATTACATCATCACAAATTAGATTTTCTTATCAATGTTTTTTTTTTTTAATCTGCACTCTGATGAGTAAATCATTCTCT
TGCTTTTAGTTGTTTCCATTGCTAGCTTTTGGTTTCATTGAACATGATCTTTTTATGCAACACAAAGTACTACCTATCTTTGTAC
TAATTTATATTGCATTGTTTGAATTTCAAAAGAGTCAGTTTAAATAGTAAGACCGAATACAAACATATAAAAAGTGTTTTATAAT
AAAATTTACATATTTAAAAATTAGATAAAAAAATATGATAAGTCGTAATAATTAACTTTGTGGATAGAGATGGCTCATTAAAGGTT
TAATGCAATGGCTTGTTTTAATTGACCACCTGAAAATATATATTATAAAAAAATATTCTTATTAGACACTTCCCGTTTAAATTTA
GAAAATGACTTTTGGGCATGTGTGTTCTCAAGTACCTTGACTACTTAAAATATGTATCACCTTATTTTTAATTATATACATTAGC
CTCGAATATTTATTGTTTATAAAGTATATGATAAAACTTTTGGTATACACAG    [Exon 3] **CATTAAGGCAACTAT
TGAACGATACAAGAAGGCAACTGCTGAAACCTCTAATGCTTGCACCACTCAAGAGCTCAATGCTCAG** [Intron 3]
GTAATTAGTTAAGCAAAATCATTTAACTTTTTGATGCTAAACAATAAAAATTCATCATTAATTCTATTTCGGGATGGATTATAAA
AAAAAAACAAATTATTAGCTATATGACAAAATATTGTTTTGGCTGTCATGTATGTAG [Exon 4] **TTTTATCAA
CAAGAATCAAAAAAGCTGCGCCAACAGATACAAATGATGCAGAATTCAAACAGG**  [Intron 4] TAACACCATAA
TTAATTCAATAAATTAAATTTGGGATGAATTTTAAAACTAATTCGATTATATGCACAAAATATTTTATATATTCCACGTGTAGG
[Exon 5] **CATCTGGTTGGTGAAGGATTAAGTTGTTTGAACGTAAGAGAGCTGAAGCAGTTGGAAAATAGACTTGAACG
AGGCATCAGCAGAATCAGATCAAAAAAG**   [Intron 5]
GTATATTGTAATGGTTGGATTACTAAAATATTGTTGTAAGTGCATACTATTGCATTGTTTGGAGTTGTAAACCAAACACATTTT
TCCTTAGAAGTTACTCGCGCTTTGAAATTACGCGTTATGATAAAATTATTTCATAAAAATATGACTCGGAAAGTTTGTTTCAAGC
CATTTGGATCTGCTCACATATAGTACAAGGCCCTAAATGAGTAATAGGAAACCTTGCACTTTTTTTTTGATAAGTGTCATATAG
AGAAAGGAAACAAAAACTTTGATATTATTTTGTTTGGTAATTAAATGAATTATAAGAAAACAAATGAATTAATTGAAACTTGAT
AAGAGTTAGACAACATTGATTATGATCCATTTTTTAGTCCATCGTGATCCAACTTGTGACAGATAATCGATATACGATCCGTTCA
TTTATTAACTTAACTCACTTTAATTTTGATCTGTCCATCTGACAACATTACATGTAGTGAAAATGTCAGCCTAAGTAGCAAAATT
TTTTATGTTGATTATACAAATCCTCATAACAGTAGCTTTGATGTTTGTTATGTGGTTGAACAG [Exon 6] **CATGAGA
TGATACTGGCTGAAACTGAGAATTTGCAGAAGAGGG**   [Intron 6] TAATAATTTATTGAAAAATTGTTTTTATCCTTT
TTATGTTTTAGGTTCAGACTAAATATAATTATGCTTTGGCATATTTTATAATCTTTCAACTTGCTGTTTTAATAGG   [Exon
7] AAATTCTACTGGAACAGGAGAATGCATTCCTTAGATCAAAG    [Intron 7] CTACTTAATTACTACCA
CACATTTCTTTTAAATTGGTTACTTAGAAAAAGAATACATTTTAATATTTATAGATAGACATTAACATCGATAATCACTTAATCT
TGTTAGTATATTTTTTAGACCCTTGAACTATGGTCTATTCCACTTAAGCAACGGAACACGATAAAGTGTTCCTAATTATAAGAA
ACTTCTGGTTTAACTTTTTGACAGATGTTTGCGCGTGTTCTTAATTATATATTAGGTATTAACTAATCACAAAATATGTCATTTC
```

Figure 3 (continued)

```
ATTTTAATTATTCACATCGACCTCAATTAAAACATGCATGCTTAAGACTTTGTTACTTATTGAGGCTAATGCATGTAATCTAAGC
AAGCGATGACACTTTTTAAGCGATCACCTTCTCCATGTAATTGACTCTTAGAATATTCCGAAAAGTTATTAAAGTGCCAAATAGA
AACACTTTATCATATGTTTAGGCGCTCAATTAGAATAAAACAAGCAAAAGTTTGTTTAAATGAAACTGACGTACACTTTAATCCC
CAAAAATTGCAAATTTTCATTTAGTTACTTTATTATTAGTACTTTATTTTTAAAAGAGAATCCGGGAGGGGATTATAAGGTGGAA
AAACAAACTCTTACCAATAAGGTGAGAGTTAAGATAACGAACCATCTGGCTAGCTACGTACTAAGATTCCCATTTAGTTATTTTC
TCTCATGGAGATTAATGAAAATATTATTGCTTTCAG    [Exon 8] ATAGCAGAAAATGAGAGGCTTCAGGAACT
AAGCATGATGCCAGCAGCAGGAGGACAAGATTACAGTGCAATACAGCAATATTTAGCAAGAAATATGCTTCAACTTAATATGATG
GAAGGCCAAGGAGTCTCTTCCTATGATCCATTGCCTCCTCCTCATCATGACAAGAAGTCCCTTGAACTTCAGTAGA    [Intron
8 ] GTATGTAGTCTTCACTTCCTCAAACAAATATCTTTATATTG TCACTATTAATTTTTTAGTTCAAGTTATATACACTGT
TAGAGTAATTAAGTAAAGTTTTGTACTATCCATAAGTCACATCTACATGTCATAGCAAATAACCTATCTTACTTTCGAGATTCCA
AATATCACAATACAAGTAGTATCATTTAGGTGAAAAAGCCCACAATTTGAGCCAAGAGTCTTTCAAAGACAGTCTCTCTATCTCT
ATGAGGTAGGGTTAAGATTTGCGTACACTCTACTCTCTCCAGGATTTCACCGGATATGTTCTTATTGCAGATACTGTAAAAGATT
TACACCAATGGTATATATAACTTGAACCTTTTTGTTGCAAAACTAAGCTCAAAATGTATGTTTGAACGTACCGATTTCTCCACTG
ATGATTCGTGTTTCTTTTGATGCAG [end Intron 8] ATAAAATCCCCAGCAAGAGGTTTGAGAATTTTACAAAAGAAC
TTTTAATGTCTACAACCTATCAAGTAATCTCTAATGACTGTATGTTGCTTAAATTAGTACCTTATTTTGTGTATTTGAATTGTTT
GTTTTGGGATTTGTAAGAAATTTGAACTTATGATGAGCTTAGAGAGTATGTTGAAGTTCAC [End 3'UTR mRNA]
TTTCTATTAGTCTTTGAGAAACTATAGCCCTCAAAGTCAATAGAAATAGGATTGATAAACCAGCAAATCCGACTTATTAGGAATG
AGTACATATATACTTTCTGAAGACAATCGCGAATACAGAAAATTTATAAAACAGAAGTAACAAAATCAGTTAATTATGAGGAACA
AAAGATGTTATAACGTGAAATGAAAGTAGCAATACGGATGGTTGATAATTCTGATGGAAAGTTAGGTAGTGCGAAAGCTCAGAAA
CGGAGAAAAAATACTTGCATCAAAGTACTAACATATAAAATAAAAAAGACTCTGGTTATGAGTTACCAATTGTCTTTAACAATTT
TGCATAGCTCGAGTACGAATTTCCCTTCCTTGTACTTCTGCGATGGCTCAACAGTTCTTTCATACTTCCAGCCCAATACCTCGTT
GCAATCCACACAGTGTATGTCAGCAATTGTGTGGAGACCAGTTGTGAGACGTTTTTGTTCATAGGTTCCAACAACAACATTTCTC
ACATGAGCAAAAGGAAAGCCTTGCTATTCTTTGACTGAAAAACAGATAATAATTTTTTCTACAGTTAATGGACAGAAACCAGAC
GATCACAGATAAAGTGCACGACAATACCAATCTAGTAACTATACATGGGCAGATGAAATCGTTCACCTGGAAGTTGGTAGAGATG
ATATCATCGTGAAATGAGACATGTCTTCGACATTTGTAGCAGCTGTAAGAGCGAGTTTTGACTAATTCATCCATCCAACAAACC
GTAACACGAAAGTTAATACTTTACACCAGGACAACTGGATACAAGGAGTAAGCCAAACTTAGAAGGAAATGAGAACGATCCAGAA
ATCTGTACTAGTTTAAACTTACAAAATTACATCAACAACTAATAGAATAGATACTGACCTGTGAGCTCCTCAGTCTCTCTTTGAG
CTTTCTCTAAGCTATCTTTCAATTCACGAATTTCTTTTTCTGCCTCTAAACGAGCAGTACGCTCT
```

PLANTS WITH AN INTENSE FRUIT PHENOTYPE

CROSS REFERENCED TO RELATED APPLICATION

This application is a continuation of U.S. patent application Ser. No. 15/022,895 filed Mar. 17, 2016, which is a 35 U.S.C. 371 National Phase of PCT Patent Application No. PCT/EP2014/069863 filed Sep. 18, 2014, which claims priority to European Patent Application No. 13184924.2 filed Sep. 18, 2013, the disclosure of these prior applications are hereby incorporated by reference in their entireties.

FIELD OF THE INVENTION

The present invention relates to the field of plant breeding, in particular tomato or Cucurbitaceae breeding. The invention provides for a plant comprising a modified amount, activity or function of AGL11-like protein, wherein the plant is a member of plant family Cucurbitaceae or of species *Solanum lycopersicum*; characterized in that the plant is not a *Solanum lycopersicum* plant having a deletion from nucleotide 1042 to nucleotide 637 upstream of the ATG start codon of SEQ ID NO: 1 (See also FIG. 3). The invention further provides seeds, parts and fruits from such plant. Also provided is the use of marker for the identification of the intense phenotype in *Solanum lycopersicum*, a method of producing tomato plants and tomato plants with intense and old-gold-crimson (ogc) phenotype and optionally powdery mildew resistance.

BACKGROUND

Intense tomato varieties, such as commercial varieties NUN 3155 TO F1 and NUN 3362 TO (Nunhems B.V.) comprise a mutation in an unknown gene (of which also the location in the genome was unknown), which converts the locular gel found in the seed cavities of tomato fruits into fleshy tissue. To see this "intense phenotype" the mutation needs to be present in homozygous form, i.e. the intense allele which confers the intense phenotype is recessive. As the mutant intense allele is present in the cultivated *S. lycopersicum* genome, which has a low degree of polymorphism in many genomic regions, it is difficult to map the responsible gene.

PCT/EP2013/055044 discloses a *Solanum lycopersicum* plant comprising a TYLCV resistance phenotype and an intense fruit phenotype, wherein said plant comprises at least one recombinant chromosome 6 comprising the recessive intense allele and an introgression fragment comprising an allele conferring TYLCV resistance in coupling configuration. This application shows that the recessive intense allele is located on chromosome 6 of *Solanum lycopersicum*, close to the locus of Ty-1 and Ty-3. This application does not show which gene, or genomic mutation, is responsible for the intense phenotype, nor does it show markers to identify the intense phenotype.

Tomato fruits with the intense phenotype have essentially no gel in the seed cavities surrounding the seeds and the locular gel (i.e. placenta tissue) is replaced by fleshy tissue. Such a phenotype is also of interest in breeding with other plant species having gel or non-fleshy tissue around the seeds.

A problem vegetable breeders are faced with is that no marker for the intense phenotype is known. Consequently, a breeder can only select plants with intense phenotype once the plant has mature fruit.

It is an object of the invention to find the genetic cause for the intense phenotype in tomato and to identify othologs of this gene in other plant species. It is also an object to provide tomato plants and plants of other species (especially cucumber and melon plants), which produce fruits having an intense phenotype, conferred by one or more mutations in the endogenous intense gene or ortholog of the gene, whereby said mutations lead to an altered expression, function or activity of the encoded protein. It is a further object to develop a marker that can be used in the selection of plants with an intense phenotype.

SUMMARY OF THE INVENTION

It was surprisingly found by the inventors that plants of species *Solanum lycopersicum* having a deletion in the promoter of the Tomato AGL11-like (TAGL11-like) gene sequence produced intense phenotype tomato fruits (such as for example NUN 3155 TO F1 and NUN 3362 TO). It is known in the art that promoters are extremely diverse and have regulatory elements several kilobases (kb) away from the transcriptional start site. They thereby influence the degree of transcription of DNA into RNA and consequently also the amount of protein being generated.

It is generally assumed that orthologs have the same biological functions in different species. Identification of orthologs allows for creating groups of genes with the same biological functions across crops. Orthologs of AGL11-like protein in other species are likely to be involved in fruit texture or fruit tissue characteristics, too.

The intense phenotype according to the present invention is based on a modified or altered, level, activity or function of the wild type AGL11-like protein in planta. The term AGL11-like protein in this respect relates to the AGL11-like gene product, such as the protein encoded by the NCBI accession number XP_004241906 (version XP_004241906.1 GI:460392605) for tomato.

The invention thus relates to a plant comprising a modified amount, activity or function of (wild type) AGL11-like protein, wherein the plant is a member of plant family Cucurbitaceae or of species *Solanum lycopersicum*; characterized in that the plant is not a *Solanum lycopersicum* plant having a deletion from nucleotide 1042 to nucleotide 637 upstream of the ATG start codon of SEQ ID NO: 1 (counting the A of the ATG start codon as number 1, see also FIG. 3). In one specific aspect the plant is a cucumber plant, melon plant or tomato plant comprising one or more mutations in the endogenous AGL11-like gene, which result in a modified (especially reduced) amount, activity or function of the AGL11-like protein encoded by the gene, and thereby result in an intense fruit phenotype (cucumber fruits, melon fruits or tomato fruits having an intense fruit phenotype).

General Definitions

The indefinite article "a" or "an" does not exclude the possibility that more than one of the element is present, unless the context clearly requires that there be one and only one of the elements. The indefinite article "a" or "an" thus usually means "at least one".

As used herein, the term "plant" includes the whole plant or any parts or derivatives thereof, such as plant organs (e.g., harvested or non-harvested storage organs, tubers, fruits, leaves, seeds, etc.), plant cells, plant protoplasts, plant cell or tissue cultures from which whole plants can be regenerated, plant calli, plant cell clumps, and plant cells that are intact in plants, or parts of plants, such as embryos, pollen, ovules, ovaries, fruits (e.g., harvested tissues or organs, such as harvested tomatoes or parts thereof), flowers, leaves, seeds, tubers, bulbs, clonally propagated plants, roots, root-stocks, stems, root tips and the like. Also any developmental stage is included, such as seedlings, immature and mature, etc.

A plant part can be regenerable or non-regenerable; alternatively a plant part can be propagating or non-propagating, for example a non-propagating plant cell, in particular a non-propagating plant cell comprising in its genome an allele causing the modified amount, activity or function of AGL11-like protein of the invention as disclosed herein is provided.

"Plant variety" is a group of plants within the same botanical taxon of the lowest grade known, which (irrespective of whether the conditions for the recognition of plant breeder's rights are fulfilled or not) can be defined on the basis of the expression of characteristics that result from a certain genotype or a combination of genotypes, can be distinguished from any other group of plants by the expression of at least one of those characteristics, and can be regarded as an entity, because it can be multiplied without any change. Therefore, the term "plant variety" cannot be used to denote a group of plants, even if they are of the same kind, if they are all characterized by the presence of one or two loci or genes (or phenotypic characteristics due to these specific loci or genes), but which can otherwise differ from one another enormously as regards the other loci or genes.

"F1, F2, etc." refers to the consecutive related generations following a cross between two parent plants or parent lines. The plants grown from the seeds produced by crossing two plants or lines is called the F1 generation. Selfing the F1 plants results in the F2 generation, etc.

"F1 hybrid" plant (or F1 hybrid seed) is the generation obtained from crossing two inbred parent lines. Thus, F1 hybrid seeds are seeds from which F1 hybrid plants grow.

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous).

The term "gene" means a DNA sequence comprising a region (transcribed region), which is transcribed into a messenger RNA molecule (mRNA) in a cell, and an operably linked regulatory region (e.g. a promoter). Herein in certain embodiments the "promoter" sequence and the "gene sequence" of the AGL11-like gene are distinguished, whereby the "gene sequence" thus refers to the DNA sequence downstream of the promoter, comprising the transcribed region (genomic DNA, transcribed into precursor-mRNA and spliced into mRNA, which is translated into protein).

The term "locus" (loci plural) means a specific place or places or a site on a chromosome where for example a gene or genetic marker is found. The intense locus is thus the location in the genome where the intense gene is found on chromosome 6 of the tomato genome or where the ortholog of the intense gene is found in cucumber or melon. Likewise the Ol-6 locus (or ogc locus) is the *S. lycopersicon* locus where the Ol-6 gene (or ogc gene) is found on chromosome 6.

"Genetic distance" between loci on the same chromosome is measured by frequency of crossing-over, or recombination frequency (RF) and is indicated in centimorgans (cM). One cM corresponds to a recombination frequency of 1%. If no recombinants can be found, the RF is zero and the loci are either extremely close together physically or they are identical. The further apart two loci are, the higher the RF.

"Introgression fragment" or "introgression segment" refers to a chromosome fragment (or part) which has been introduced into another plant of the same or related species by crossing or traditional breeding techniques. In tomato, wild relatives of tomato are often used to introgress fragments of the wild genome into the genome of cultivated tomato, *S. lycopersicum*. Such a cultivated tomato plant thus has a "genome of *S. lycopersicum*", but comprises in the genome a fragment of a wild relative of tomato, e.g. an introgression fragment of a related wild species'genome, such as *Solanum chilense* or another wild relative of tomato. It is understood that the term "introgression fragment" never includes a whole chromosome, but only a part of a chromosome.

"Intense allele" (or "Int") or "intense allele" (or "i") refers herein refers to an allele conferring a "normal fruit phenotype" (Int) or an "intense phenotype" (i), respectively. The "Intense allele" is herein used interchangeably with "AGL11-like allele" (leading to expression of a wild type, functional AGL11-like protein) and the "intense allele" is used interchangeably with agl11-like allele (leading to reduced amount, activity or function of the wild type AGL11-like protein). In *Solanum lycopersicum*, and likely also in cucumber and melon, the Intense allele is dominant, i.e. it is the allele which, when present in the genome in one (heterozygous) or two (homozygous) copies confers normal tomato fruits, having normal seed cavities, i.e. with gel around the seeds (locular gel). Tomato fruits having a "normal fruit phenotype" thus refer to fruits which have locular gel, as shown for example in FIG. 1, left side. The intense allele is recessive, i.e. only when the dominant Intense allele is lacking from the genome is the intense phenotype seen. Thus *Solanum lycopersicum* (or cucumber or melon)plants having an Intense/Intense (Int/Int) or Intense/intense (Int/i) genotype have a normal fruit phenotype, while homozygous intense/intense (i/i) plants have an "intense fruit phenotype", as shown e.g. in FIG. 1, right side (see further below).

Epicarp is a botanical term for the outermost layer of the pericarp (or fruit). The epicarp forms the tough outer skin of the fruit. The epicarp is sometimes called the exocarp. Mesocarp is the botanical term for the succulent and fleshy middle layer of the pericarp of a fruit, between the epicarp and the endocarp; it is usually the major part of the fruit that is eaten, for example, mesocarp makes up a considerable proportion of a tomato. This term may also refer to any fruit that is fleshy throughout. Endocarp is a botanical term for the inside layer of the pericarp (or fruit), which directly surrounds the seeds.

Endocarp tissue in cucumber refers to the gelatinous tissue surrounding the seeds and includes the associated placental tissue. Mesocarp tissue refers the fleshy tissue between the peel and gelatinous endocarp tissue, i.e. the edible fruit tissue.

The "intense phenotype" or "intense fruit phenotype" is the phenotype conferred by the presence of two mutant *Solanum lycopersicum* (or *Cucumis sativus* or *Cucumis melo*) intense alleles in the genome, whereby in tomato the homozygous intense alleles (intense/intense) cause the locular gel (i.e placenta tissue) found in the seed cavities of tomato fruits to become fleshy tissue. The mature tomato fruits therefore have essentially no gel in the seed cavities surrounding the seeds and the locular gel is replaced by fleshy tissue. The intense phenotype of tomato is depicted e.g. in FIG. 1, fruit on the right. In other crops the intense phenotype can be present in a similar way, i.e. altering the inner fruit tissue characteristics, especially making the inner fruit tissue (e.g. the placental tissue or tissue around the seeds) more solid than in normal fruits. In Cucurbiteae, e.g. *Cucumis melo*, which normally has a cavity in the middle comprising the melon seeds and a gel-like texture (placenta tissue), the intense phenotype may cause the placenta tissue to become more solid. The degree of solidity may depend on several parameters such as type of fruit variety and ripeness of fruit. In some cases the intense phenotype may cause the placenta tissue to be so solid that it binds the majority of (melon) seeds to each other. E.g., at least 50% of the seeds or at least 60%, 70%, 80%, 90%, or even at least 95% or 99% of the seeds are bound to together by the placenta tissue of the fruit.

In other cases, like for example in seedless fruits, the intense phenotype causes the (placenta) tissue at the position where the seeds are normally located, to become more solid, this can for example be the case in cucumber.

The "normal fruit phenotype" or "wild type fruit phenotype" refers to the tomato or Cucurbitaceae (especially cucumber and melon) fruits comprising gel or softer tissue in the seed cavities or around the seeds or where normally seeds would be (e.g. locular gel or placenta tissue) compared to the outer fruit tissue, due to the presence of an (wild type) Intense allele, either in homozygous or heterozygous form (Intense/Intense or Intense/intense). The normal fruit phenotype in tomato is depicted e.g. in FIG. 1, fruit on the left.

The "ogc allele" refers to an old-gold-crimson-conferring allele on *Solanum lycopersicum* chromosome 6 (ogc). The recessive allelic mutations old-gold-crimson (ogc), has the phenotype of deep red fruits that lack b-carotene and tawny orange flowers. The locus ogc was found to be on chromosome 6 of the tomato (Ronen et al 2000 PNAS vol 97 pp 11102-11107). Ogc has been used extensively in processing tomato breeding programs for the midwestern and eastern United States. This gene works through a biochemical mechanism that is distinct from the high pigment genes, as it increases lycopene content and reduces β-carotene content (Sacks et al 2001, J. Amer. Soc. Hort. Sci. vol 126 pp 221-226).

The "ogc phenotype" or "ogc fruit phenotype" is the phenotype conferred by the presence of two recessive *Solanum lycopersicum* ogc alleles in the genome. It presence can be easily determined visually by analysing ripe tomato fruits: cut the ripe tomato fruit into two halves and determine the tomato flesh colour. Compare the colour to a normal fruit type like e.g. Heinz or Moneymaker. Ogc phenotype has deep red flesh colour (red towards purple red) while a normal tomato has a less red flesh colour (red towards yellow-red). Pericarp of a normal tomato sometimes even has a white or green-white colour.

Alternatively the 'ogc phenotype can be objective measured using a colorimeter as described by Darrigues et al (Darrigues et al 2008, J Amer Soc Hort Scir vol 133 pp 579-586).

The "Ol-6 allele" refers to a dominant *Oidium lycopersicum* resistance conferring allele on chromosome 6.

An "Oidium resistance phenotype" or "Oidium lycopersici resistance" or refers to resistance against powdery mildew (*Oidium neolycopersici*) conferred by the Ol-6 allele when present in the tomato genome in one or two copies.

A "Oidium resistance assay" or powdery mildew resistance test can be carried out in different ways, either as an artificial inoculation assay or as a field test, as commonly known in the art. For example using the method as described by Bai et al (Bai Y. et al. 2003 Molecular Plant Microbe Interactions, vol 16/2, pp 169-176).

The "Ol-6 marker assay" is a molecular marker assay which can be used to test the presence of Ol-6 allele "Tomato plants" or "cultivated tomato plants" are plants of the *Solanum lycopersicum*, i.e. varieties, breeding lines or cultivars of the species *Solanum lycopersicum*, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of a species. The so-called heirloom varieties or cultivars, i.e. open pollinated varieties or cultivars commonly grown during earlier periods in human history and often adapted to specific geographic regions, are in one aspect of the invention encompassed herein as cultivated tomato plants.

Tomato and the wild relatives of tomato is/are diploid and has/have 12 pairs of homologous chromosomes, numbered 1 to 12. "Tomato chromosome 6" refer to the *Solanum lycopersicum* chromosome 6, as known in the art. "Orthologous chromosome 6" refers to the chromosome 6 of wild relatives of tomato, parts of which can be introgressed into tomato chromosome 6.

"Wild relatives of tomato" include *S. arcanum*, *S. chmielewskii*, *S. neorickii* (=*L. parviflorum*), *S. cheesmaniae*, *S. galapagense*, *S. pimpinellifolium*, *S. chilense*, *S. corneliomulleri*, *S. habrochaites* (=*L. hirsutum*), *S. huaylasense*, *S. sisymbriifolium*, *S. peruvianum*, *S. hirsutum* or *S. pennellii*.

"Cucumber plants" or "cultivated cucumber plants" as used here denotes varieties, breeding lines or cultivars of *Cucumis sativus* L. cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of a species. The term "cucumber fruit" is used to refer specifically to the fruit. This cucumber fruit can be a gherkin, a long-, a short-, a mini-cucumber (Beith Alpha cucumber) or a midi-cucumber.

"Melon" or "muskmelon" refers herein to plants of the species *Cucumis melo*. Melons or 'muskmelons', *Cucumis melo*, can be classified into: *C. melo cantalupensis*, *C. melo inodorous* and *C. melo reticulatus*. *C. melo cantalupensis* are also referred to as Cantaloupes and are primarily round in shape with prominent ribs and almost no netting. Most have orange, sweet flesh and they are usually very fragrant. In contrast to the European cantaloupe, the North American 'Cantaloupe' is not of this type, but belongs to the true muskmelons. *C. melo inodorous* (or winter melons) can be subdivided into different types, such as Honeydew melon, Piel de Sapo, Sugar melon, Japanese melon, etc. *C. melo reticulatus* is the true muskmelon, with reticulated skin (netted) and includes Galia melons, Sharlyn melons and the North American cantaloupe.

"Cultivated melon" refers to plants of *Cucumis melo* i.e. varieties, breeding lines or cultivars of the species *C. melo*, cultivated by humans and having good agronomic characteristics, especially producing edible and marketable fruits of good size and quality and uniformity; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of a species.

"Average" refers herein to the arithmetic mean.

"In coupling phase" or "in coupling configuration" or "in cis" refers to the genetic condition in which the alleles of two different loci are genetically and physically linked together as a unit on one chromosome and inherit together as a unit. Preferably the loci are in close proximity to one another, reducing the likelihood that they will be separated again by recombination.

A "recombinant chromosome" refers to a chromosome having a new genetic makeup arising through crossing over between homologous chromosomes, e.g. a "recombinant chromosome 6", i.e. a chromosome 6 which is not present in either of the parent plants and arose through a rare crossing-over event between homologous chromosomes of a chromosome 6 pair. Herein, for example, a recombinant tomato chromosome 6 comprising ogc and intense in coupling phase (in cis) is provided, as is a recombinant tomato chromosome 6 comprising ogc and intense and Ol-6 in coupling phase (in cis).

The term "traditional breeding techniques" encompasses herein crossing, selfing, selection, double haploid production, embryo rescue, protoplast fusion, marker assisted selection, mutation breeding etc. as known to the breeder (i.e. methods other than genetic modification/transformation/transgenic methods), by which, for example, a recombinant chromosome 6 or a mutant intense allele can be obtained and/or transferred.

The term "mutation in a gene sequence" refers to an addition of one or more (e.g. at least 1, 2, 3, 4, 5, 10, 20, 50 or more) nucleotides in the gene sequence; or alternatively to a deletion of one or more nucleotides (e.g. at least 1, 2, 3, 4, 5, 10, 20, 40, 80, 100, 150, 200, 300, 400, 500 or more) in the gene sequence; or alternatively a replacement of one or more (e.g. at least 1, 2, 3, 4, 5, 10, 20, 50 or more) nucleotides in the gene sequence. Also combinations of mutations can occur e.g. an addition and a deletion or replacement, or a deletion and a replacement or addition, or even two or more additions, or two or more deletions, or two or more replacements.

Similarly, the term "mutation in the promoter of a gene sequence" refers to an addition of one or more nucleotides in said promoter sequence; or alternatively to a deletion of one or more nucleotides in said promoter sequence; or alternatively a replacement of one or more nucleotides in said promoter sequence.

Mutations in a gene sequence or promoter sequence may be caused by methods known in the art such as TILLING (vide infra).

The term "AGL11-like protein" is defined as the "Agamous Like 11 like" (AGL11-like) gene product, such as the protein encoded by the NCBI accession number XP_004241906 (version XP_004241906.1 GI:460392605) for tomato (Tomato AGL11-like or TAGL11-like protein). In one aspect of the invention "AGL11-like protein" refers to orthologs of the tomato AGL11-like protein, such as AGL11-like protein orthologs in cucumber or melon.

Tomato AGL11-like protein is a MADS box protein. MADS box proteins are known to form dimers with itself or to form heterodimers with other MADS box proteins (Shore et al (1995) Eur. J. Biochemistry vol 229 pp 1-13). In one aspect of the invention "AGL11-like protein" refers to heterodimers comprising one AGL11-like protein or ortholog thereof.

A modified amount, activity or function of AGL11-like protein therefor also refers to a modified (e.g. decreased) amount of heterodimer of an AGL11-like protein or ortholog thereof, with another MADS box protein.

The term ortholog is defined as genes in different species that have evolved through speciation events. It is generally assumed that orthologs have the same biological functions in different species. Identification of orthologs accomplishes two goals: delineating the genealogy of genes to investigate the forces and mechanisms of evolutionary process, and creating groups of genes with the same biological functions (Fang G, et al (2010) Getting Started in Gene Orthology and Functional Analysis. PLoS Comput Biol 6(3): e1000703. doi:10.1371/journal.pcbi.1000703). Orthologs of a specific gene or protein can be identified using sequence alignment or sequence identity of the gene sequence of the protein of interest with gene sequences of other species. Gene alignments or gene sequence identity determinations can be done according to methods known in the art. In one aspect of the invention an ortholog of AGL11-like protein has at least 45% (e.g. at least 48%, 50%, 52%, 54%, 55%, 58%, 60%, 65%, 70%, 75%, 80%, 85%, 90%, 95%, 98%, 99%, or more) amino acid sequence identity with SEQ ID NO: 3.

Orthologs of tomato AGL11-like protein (TAGL11-like protein) in other species can also be identified based on their role in fruit formation, especially in fruit phenotype, texture of locular gel (i.e placenta tissue) or fruit flesh characteristics, especially orthologs of tomato AGL11-like proteins lead to an intense fruit phenotype when the promoter or gene is mutated, so that the fruit produced a reduced amount of functional (wild type) AGL11-like orthologous protein (e.g. due to a mutation in the promoter sequence) or produces a mutant agl11-like orthologous protein having reduced activity or function compared to the wild type AGL11-like protein.

"Stringent hybridisation conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point ($T_m$) for the specific sequences at a defined ionic strength and pH. The $T_m$ is the temperature (under defined ionic strength and pH) at which 50% of the target sequence hybridises to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridisations (Northern blots using a probe of e.g. 100 nt) are for example those which include at least one wash in 0.2×SSC at 63° C. for 20 min, or equivalent conditions. Stringent conditions for DNA-DNA hybridisation (Southern blots using a probe of e.g. 100 nt) are for example those which include at least one wash (usually 2) in 0.2×SSC at a temperature of at least 50° C., usually about 55° C., for 20 min, or equivalent conditions. See also Sambrook et al. (1989) and Sambrook and Russell (2001).

"Sequence identity" and "sequence similarity" can be determined by alignment of two peptide or two nucleotide sequences using global or local alignment algorithms. Sequences may then be referred to as "substantially identical" or "essentially similar" when they are optimally aligned by for example the programs GAP or BESTFIT or the Emboss program "Needle" (using default parameters, see below) share at least a certain minimal percentage of sequence identity (as defined further below). These programs use the Needleman and Wunsch global alignment algorithm to align two sequences over their entire length, maximizing the number of matches and minimises the number of gaps. Generally, the default parameters are used, with a gap creation penalty=10 and gap extension penalty=0.5 (both for nucleotide and protein alignments). For nucleotides the default scoring matrix used is DNAFULL and for proteins the default scoring matrix is Blosum62 (Henikoff & Henikoff, 1992, PNAS 89, 10915-10919). Sequence alignments and scores for percentage sequence identity may for example be determined computer programs, as using such EMBOSS (http://www.ebi.ac.uk/Tools/psa/emboss_needle/). Alternatively sequence similarity or identity may be determined by searching against databases such as FASTA, BLAST, etc., but hits should be retrieved and aligned pairwise to compare sequence identity. Two proteins or two protein domains, or two nucleic acid sequences have "substantial sequence identity" if the percentage sequence identity is at least 75%, 85%, 90%, 95%, 98%, 99% or more (e.g. at least 99.1, 99.2 99.3 99.4, 99.5, 99.6, 99.7, 99.8, 99.9 or more (as determined by Emboss "needle" using default parameters, i.e. gap creation penalty=10, gap extension penalty=0.5, using scoring matrix DNAFULL for nucleic acids an Blosum62 for proteins).

Putative TAGL11-like protein orthologs can be identified in silico, e.g. by identifying nucleic acid or protein sequences in existing nucleic acid or protein database (e.g. GENBANK, SWISSPROT, TrEMBL) and determine sequence identity (vide supra) with the protein of interest or using standard sequence analysis software, such as sequence similarity search tools (BLASTN, BLASTP, BLASTX, TBLAST, FASTA, etc.).

The "promoter of a gene sequence" is defined as a region of DNA that initiates transcription of a particular gene. Promoters are located near the genes they transcribe, on the same strand and upstream on the DNA. Promoters can be about 100-1000 base pairs long. In one aspect the promoter is defined as the region of about 1000 base pairs or more e.g. about 1500 or 2000, upstream of the start codon (i.e. ATG) of the protein encoded by the gene.

A genetic element, an introgression fragment, or a (mutant) gene or allele conferring a trait is said to be "obtainable from" or can be "obtained from" or "derivable from" or can be "derived from" or "as present in" or "as found in" a plant or seed or tissue or cell if it can be transferred from the plant or seed in which it is present into another plant or seed in which it is not present (such as a line or variety) using traditional breeding techniques without resulting in a phenotypic change of the recipient plant apart from the addition of the trait conferred by the genetic element, locus, introgression fragment, gene or allele. The terms are used interchangeably and the genetic element, locus, introgression fragment, gene or allele can thus be transferred into any other genetic background lacking the trait. Not only seeds deposited and comprising the genetic element, locus, introgression fragment, gene or allele can be used, but also progeny/descendants from such seeds which have been selected to retain the genetic element, locus, introgression fragment, gene or allele, can be used and are encompassed herein, such as commercial varieties developed from the deposited seeds or from descendants thereof. Whether a plant (or genomic DNA, cell or tissue of a plant) comprises the same genetic element, locus, introgression fragment, gene or allele as obtainable from the deposited seeds can be determined by the skilled person using one or more techniques known in the art, such as phenotypic assays, whole genome sequencing, molecular marker analysis, trait mapping, chromosome painting, allelism tests and the like.

The term "traditional breeding techniques" encompasses herein crossing, backcrossing, selfing, selection, double haploid production, embryo rescue, protoplast fusion, marker assisted selection, mutation breeding etc. as known to the breeder (i.e. methods other than genetic modification/transformation/transgenic methods), by which, for example, a recombinant chromosome or mutant can be obtained, identified and/or transferred.

"Human induced mutation" or "human induced recombinant" refers to a mutation (e.g. in the AGL11-like ortholog gene or promoter) or recombination event (e.g. recombinant chromosome 6) induced and identified/selected by human intervention, i.e. not occurring in nature.

BRIEF DESCRIPTION OF THE SEQUENCE LISTING

SEQ ID NO: 1 Shows the *Solanum lycopersicum* wild type fully functional tomato AGL 11-like promoter sequence as provided by the International Tomato Annotation Group (ITAG), ITAG Release 2.3 (2011-04-26) official annotations on the SL2.40 genome build by the International Tomato Annotation Group (ITAG). Data is openly and freely available on SGN (solgenomics.net/), SL2.40ch06 36808000 . . . 36817500.

SEQ ID NO: 2 deletion in promoter sequence of wild type TAGL11-like sequence (as given in SEQ ID NO: 1) causing the intense fruit phenotype in tomato.

SEQ ID NO: 3 wild type Tomato AGL11-like protein sequence based upon NCBI Reference Sequence of locus XM_004241858, version XM_004241858.1 GI: 460392604, as given by NCBI on ncbi.nlm.nih.gov/nuccore/XM_004241858.1.

SEQ ID NO: 4 wild type Tomato AGL11-like cDNA based upon NCBI Reference Sequence of locus XM_004241858, version XM_004241858.1 GI: 460392604, as given by NCBI on ncbi.nlm.nih.gov/nuccore/XM_004241858.1.

SEQ ID NO: 5 wild type Tomato AGL11-like genomic DNA without promoter (obtained from the same source as SEQ ID NO: 1).

SEQ ID NO: 6 first AGL11-like ortholog in cucumber protein CU100500 (C1)

SEQ ID NO: 7 $2^{nd}$ AGL11-like ortholog in cucumber protein CU 105950 (C2)

SEQ ID NO: 8 $3^{rd}$ AGL11-like ortholog in cucumber protein AAC08528 (C3)

SEQ ID NO: 9 $4^{th}$ AGL11-like ortholog in cucumber protein CU107465 (C4)

SEQ ID NO: 10 first AGL11-like ortholog in cucumber cDNA (C1).

SEQ ID NO: 11 $2^{nd}$ AGL11-like ortholog in cucumber cDNA (C2).

SEQ ID NO: 12 $3^{rd}$ AGL11-like ortholog in cucumber cDNA (C3).

SEQ ID NO: 13 $4^{th}$ AGL11-like ortholog in cucumber cDNA (C3).

SEQ ID NO: 14 first AGL11-like ortholog in melon protein Mu43977 (M1)

SEQ ID NO: 15 $2^{nd}$ AGL11-like ortholog in melon protein Mu45645 (M2)

SEQ ID NO: 16 $3^{rd}$ AGL11-like ortholog in melon protein Mu50731 (M3)

SEQ ID NO: 17 4$^{th}$ AGL11-like ortholog in melon protein Mu48843 (M4)

SEQ ID NO: 18 first AGL11-like ortholog in melon cDNA (M1).

SEQ ID NO: 19 2$^{nd}$ AGL11-like ortholog in melon cDNA (M2).

SEQ ID NO: 20 intense promoter sequence (SEQ ID NO: 1 without SEQ ID NO: 2)

SEQ ID NO: 21 3$^{rd}$ AGL11-like ortholog in melon cDNA (M3).

SEQ ID NO: 22 4$^{th}$ AGL11-like ortholog in melon cDNA (M4).

SEQ ID NO: 23 first AGL11-like ortholog in cucumber genomic DNA (C1).

SEQ ID NO: 24 2$^{nd}$ AGL11-like ortholog in cucumber genomic DNA (C2).

SEQ ID NO: 25 3$^{rd}$ AGL11-like ortholog in cucumber genomic DNA (C3).

SEQ ID NO: 26 4$^{th}$ AGL11-like ortholog in cucumber genomic DNA (C4).

SEQ ID NO: 27 *Solanum lycopersicum* wild type, fully functional, tomato AGL11-like genomic DNA sequence (i.e. sequence as depicted in FIG. 3), obtained from the same source as SEQ ID NO: 1.

SEQ ID NO: 28 Forward primer to detect intense phenotype in *Solanum lycopersicum*.

SEQ ID NO: 29: Reverse primer to detect intense phenotype in *Solanum lycopersicum*.

SEQ ID NO: 30: consensus protein sequence as shown in FIG. 2.

FIGURE LEGENDS

FIG. 1: Photograph of a cut-open tomato fruit having the intense phenotype (right) and a fruit having the normal fruit phenotype (left).

FIG. 2: Protein Tomato AGL11-like sequence (SEQ ID NO: 3) alignment with AGL11-like orthologs in melon (M1 (SEQ ID NO: 14), M2 (SEQ ID NO: 15), M3 (SEQ ID NO: 16), M4 (SEQ ID NO: 17)) and cucumber (C1 (SEQ ID NO: 6), C2 (SEQ ID NO: 7), C3 (SEQ ID NO: 8), C4 (SEQ ID NO: 9)).

FIG. 3: *Solanum lycopersicum* wild type fully functional genomic DNA of AGL11-like gene+promoter sequence ([SEQ ID NO: 5] and SEQ ID NO: 1, respectively), taken from the International Tomato Annotation Group (ITAG), official annotations on the SL2.40 genome build by the International Tomato Annotation Group (ITAG) (http://solgenomics.net/) Solgenomics web site, SL2.40ch06 36808000 . . . 36817500; Annotation is given between brackets [ ]. The deletion in the promoter causing the intense phenotype in tomato has been indicated (residue 1042 to (not including) 637) upstream of the ATG start codon [SEQ ID NO: 2]. Exon 1-8 (in bold) and Intron 1-8 are indicated. The stop codon (TAG) starts 4 nucleic acids before the end of Exon 8.

Figure 4:
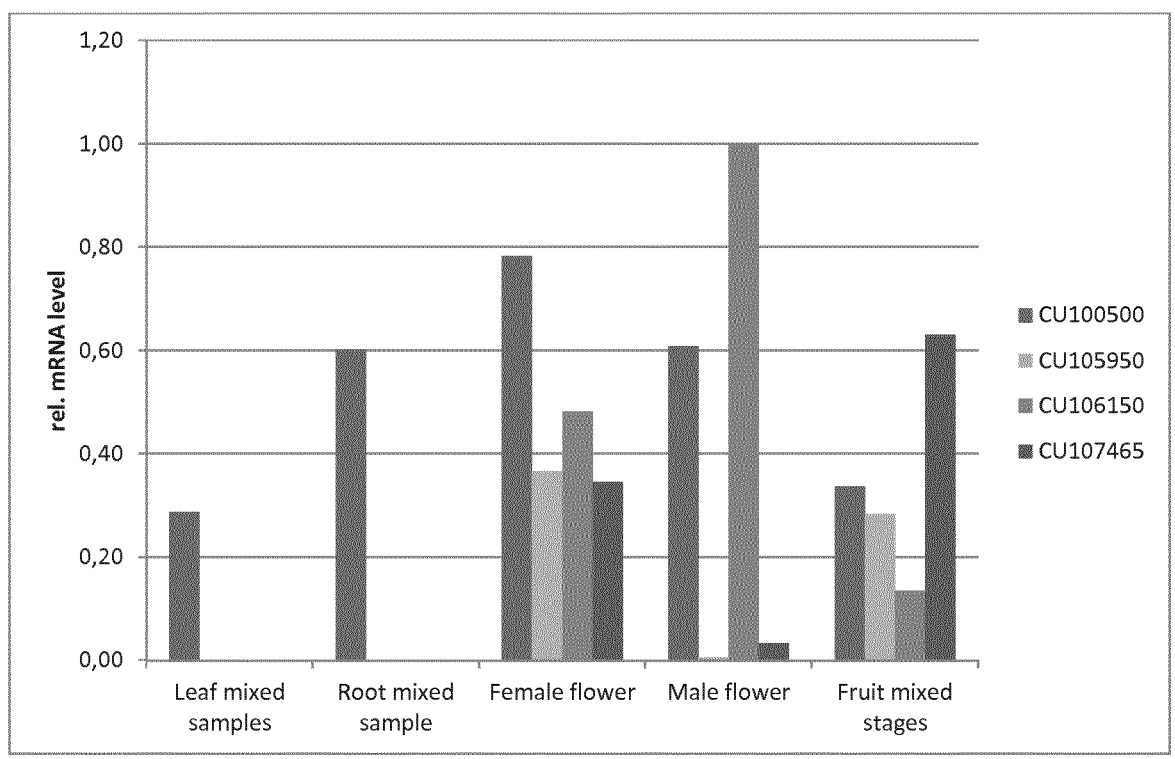

FIG. 4: Relative mRNA level of four AGL11-like orthologs in different samples of cucumber plant

DETAILED DESCRIPTION OF THE INVENTION

The present invention relates to a plant comprising a modified amount, activity or function of AGL11-like protein or AGL11-like protein ortholog, wherein the plant is a member of plant family Cucurbitaceae or of species *Solanum lycopersicum*; characterized in that the plant is not a *Solanum lycopersicum* plant having a deletion from nucleotide 1042 to nucleotide 637 upstream of the ATG start codon of SEQ ID NO: 1 (as indicated in FIG. 3).

In one aspect the invention relates to a plant comprising a modified amount, activity or function of AGL11-like protein or ortholog, wherein the plant is a member of plant family Cucurbitaceae or of species *Solanum lycopersicum*; characterized in that the plant is not a *Solanum lycopersicum* plant having a sequence identical to SEQ ID NO: 2 on chromosome 6.

In one aspect of the invention the plant is a non-transgenic plant, e.g. a plant obtainable by traditional breeding methods.

In another aspect of the invention the plant of the invention is a member of genus *Cucumis* or of species *Solanum lycopersicum*. In yet another aspect the invention relates to the plant of species *Solarium lycopersicum, Cucumis melo*, or *Cucumis sativus*. In yet another aspect the invention relates to a plant of the species *Solanum lycopersicum*. In still another aspect the invention relates to a plant of the family Cucurbitaceae. In another aspect the plant is of the genus *Cucumis*. In still another aspect the plant is of the species *Cucumis melo*. In an even further aspect the plant is of the species *Cucumis sativus*.

In one aspect the plant of the invention is of species *Solarium lycopersicum, Cucumis melo*, or *Cucumis sativus*.

Modifying the amount of AGL11-like protein or AGL11-like protein ortholog in a plant can be an increased amount or a reduced (decreased) amount of (wild type; functional) AGL11-like protein or ortholog when compared to normal plants comprising a normal fruit phenotype. The amount of a protein can be changed by mutation (e.g. additions, substitutions, or deletions of nucleic acids in the promoter sequence of a gene encoding an AGL11-like protein or ortholog. Alternatively, mutations (e.g. additions, substitutions, or deletions) in the coding sequence of a protein may lead to non-functional or reduced-function protein. In one aspect of the invention, the modified amount is an increased amount. In another aspect the modified amount is a decreased amount. In yet a further aspect, the modified amount is an absence of the AGL11-like protein or ortholog.

A modified activity or function of the AGL11-like protein or ortholog can be caused by one or more mutations in the amino acid sequence of the protein (compared to wild type AGL11-like protein or AGL11-like protein ortholog). Such mutations can have a natural cause (spontaneous) or can be induced via methods known in the art such as mutagenesis and identified by e.g. TILLING (vide infra). In one aspect, plants of the invention are tomato, cucumber or melon mutant plants, especially TILLING mutants, which comprise and intense phenotype due to one or more mutations in the promoter or gene sequence of the endogenous AGL11-like protein (or ortholog), said mutation(s) leading to a reduced amount of wild type AGL-like protein (or wild type ortholog) or to a reduced activity or function of the AGL11-like protein (or otholog).

In one aspect the invention relates to a plant of the invention wherein the modified amount, activity or function of AGL11-like protein or ortholog can be determined during fruit formation. In a further aspect the modified amount, activity or function of AGL11-like protein or ortholog in the plant of the invention can be determined during fruit formation in the fruit or flowers of the plant.

In a further aspect fruits of the plant of the invention have an intense phenotype. In another aspect fruits of the plants of the invention have placenta tissue with a similar toughness as fruit flesh of the fruit. In one aspect the toughness of the placenta tissue is at least 50% of the fruit flesh, in another at least 55%, in another at least 60%, in another at least 65%, in another at least 70%, in another at least 75%, in another at least 80%, in another at least 85%, in another at least 90%, in another at least 95%, in another at least 98%.

Fruit tissue toughness can be measured for example using a penetrometer by measuring the force needed to punch a hole of a certain size through/or in the material.

In one aspect the plant of the invention is homozygous for the allele causing the modified amount, activity or function of AGL11-like protein or ortholog. In another embodiment the plant of the invention is heterozygous for the allele causing the modified amount, activity or function of AGL11-like protein or ortholog. Crossing two inbred lines yields an F1 hybrid. Such an F1 hybrid can be homozygous or heterozygous depending on either one or both parents being homozygous for the allele causing the modified amount, activity or function of AGL11-like protein or ortholog.

Commercial vegetable varieties often are hybrids obtained from a crossing of two inbred parental lines. In one aspect the plant of the invention is a F1 hybrid.

In another aspect the modified amount, activity or function of AGL11-like protein or ortholog is due to one or more mutations in the gene sequence of AGL11-like protein or AGL11-like protein ortholog (i.e. the sequence encoding the protein) or in the promoter thereof.

In another aspect the modified amount, activity or function of AGL11-like protein or ortholog is due to one or more mutations in the gene sequence of AGL11-like protein or ortholog (i.e. the sequence encoding the protein), in another aspect it is due to a mutation in the promoter of the gene sequence of AGL11-like protein or ortholog.

In one aspect the invention relates to a plant of the invention wherein the plant is of species *Solanum lycopersicum* and wherein the AGL11-like protein has at least 75% amino acid sequence identity to SEQ ID NO: 3, e.g. at least 80%, or at least 85%, 90%, 94%, 96%, 98%, 99%, or even at least 99.2%, or at least 99.4%, 99.6%, 99.8%, or at least 99.9%. Differences in sequence identity may be caused by one or more amino acid deletions, insertions or replacements compared to SEQ ID NO: 3.

In another aspect the invention relates to a plant of the invention wherein the plant is of species *Solanum lycopersicum* and wherein the cDNA encoding the AGL11-like protein has at least 75% nucleic acid sequence identity to SEQ ID NO: 4, e.g at least 80%, or at least 85%, 90%, 94%, 96%, 98%, 99%, or even at least 99.2%, or at least 99.4%, 99.6%, 99.8%, or at least 99.9% nucleic acid identity.

In another aspect the invention relates to a plant of the invention wherein the plant is of species *Solanum lycopersicum* and wherein the genomic DNA encoding the AGL11-like protein has at least 60% nucleic acid sequence identity to SEQ ID NO: 5, e.g at least 65%, or at least 70%, 75%, 80%, 85%, 90%, 94%, 96%, 98%, 99%, or even at least 99.2%, or at least 99.4%, 99.6%, 99.8%, or at least 99.9% nucleic acid identity.

In a further aspect the invention relates to a plant of the invention wherein the plant is of species *Solanum lycopersicum*, and wherein the modified amount, activity or function of AGL11-like protein is due to one or more mutations in the promoter of the gene sequence of the AGL11-like protein, as depicted in SEQ ID NO: 1, and wherein the mutation is a deletion, insertion or nucleotide replacement. In yet another aspect said mutation is a deletion of at least 1 nucleotide. In yet another aspect said deletion is at least 2, or even at least 3, 5, 10, 20, 30, 40, 50, 80, 100, 150, 200, 250, 300, 350 nucleotides. In still another aspect said deletion is at least 400 nucleotides or even at least 450 or 500 or even the complete promoter as depicted in SEQ ID NO: 1 is missing.

This invention is based on research performed on fruit phenotypes in tomato plants (*Solanum lycopersicum*) and the genetic cause(s) for such phenotypes. As orthologs of proteins in one plant have a similar function in other plants, this invention can be more generally applied in plants, in particular in crop plants that have fruits with gel-like fruit cavities. Examples of such plants are plants of family Cucurbitaceae like those of the genus *cucumis*, like for example *Cucumis sativus* and *Cucumis melo*.

When the modification of the amount of AGL11-like protein in a plant is to be achieved via genetic modification of the AGL11-like gene or via the identification of mutations in the AGL11-like gene, and the gene is not yet known, it must first be identified. This means that orthologs of the tomato AGL11-like protein must be identified and optionally isolated in non-tomato plants.

Various methods are known in the art for the identification of orthologous sequences in other plant species. For example by designing primers based on the tomato AGL11-like gene, based on conserved domains (which are common in MADS box proteins) as determined by multiple nucleotide sequence alignment, and used to PCR amplify the orthologous sequence. Such primers are suitably degenerate primers (e.g. as described in WO2008/092505).

Another method to assess a given sequence as being a AGL11-like ortholog is by identification of the reciprocal best hit. A candidate orthologous AGL11-like sequence of a given plant species identified as the best hit from DNA databases (e.g. from NCBI or TAIR) when searching with tomato AGL11-like protein or nucleotide sequence.

AGL11-like protein is encoded by a single gene in tomato. In the genome of cucumber (*Cucumis sativus*) 4 orthologs have been identified, and in the genome of melon (*Cucumis melo*) also 4 orthologs have been identified. These orthologs were identified by nucleotide and amino acid comparisons with the information that is present in public databases (see examples). The alignment of these orthologous sequences (protein) are shown in FIG. 2. TAGL11-like represents the Tomato AGL11-like protein, M1-M4 represent 4 ortholog sequences in melon (*Cucumis melo*), C1-C4 represent 4 ortholog sequences in cucumber (*Cucumis sativus*). It is noted that the consensus (last line) between the orthologs is largest in the first half of the proteins.

Alternatively, if no DNA sequence is available for the desired plant species, orthologous sequences can be isolated by heterologous hybridization using DNA probes of the AGL11-like gene of *Solanum lycopersicum* or by PCR methods, making use of the conserved domains MADS box proteins in general (AGL11-like protein is a MADS box protein).

In one aspect the invention relates to a plant of the invention (i.e. having an intense fruit phenotype due to an altered, especially reduced, amount activity or function of the endogenous AGL11-like protein ortholog) wherein the plant is a member of plant family Cucurbitaceae, and the AGL11-like protein is an ortholog of the TAGL11-like protein represented by SEQ ID NO: 3 (i.e. the AGL11-like protein of tomato). In a further aspect the invention relates to a plant of the invention wherein the plant is a member of plant family Cucurbitaceae, and the AGL11-like protein is an ortholog of the TAGL11-like protein represented by SEQ ID NO: 3, wherein the ortholog comprises at least 40% amino acid sequence identity to SEQ ID NO: 3, e.g. at least 45%, 48%, 50%, 52%, 55%, or at least 60%, 65%, 70%, 75%, 80%, 85%, or even at least 90%, or at least 95%, or at least 99% amino acid identity to SEQ ID NO: 3 (using a pairwise alignment and the program Needle).

In a further aspect the invention relates to a plant of the invention (i.e. having an intense fruit phenotype due to an altered, especially reduced, amount activity or function of the endogenous AGL11-like protein ortholog) wherein the plant is a member of species *Cucumis sativus*, and the AGL11-like protein is an ortholog of the TAGL11-like protein represented by SEQ ID NO: 3, wherein the ortholog comprises at least 40% amino acid sequence identity to SEQ ID NO: 3, e.g. at least 45%, 48%, 50%, 52%, 55%, or at least 60%, 65%, 70%, 75%, 80%, 85%, or even at least 90%, or at least 95%, or at least 99% amino acid identity. In one aspect the ortholog is a *Cucumis sativus* ortholog comprising at least least 40% amino acid sequence identity to SEQ ID NO: 6, 7, 8 or 9, e.g. at least 45%, 48%, 50%, 52%, 55%, or at least 60%, 65%, 70%, 75%, 80%, 85%, or even at least 90%, or at least 95%, or at least 99% amino acid identity.

In a further aspect the invention relates to a plant of the invention (i.e. having an intense fruit phenotype due to an altered, especially reduced, amount activity or function of the endogenous AGL11-like protein ortholog) wherein the plant is a member of species *Cucumis melo*, and the AGL11-like protein is an ortholog of the TAGL11-like protein represented by SEQ ID NO: 3, and has at least 40% amino acid sequence identity to SEQ ID NO: 3, e.g. at least 45%, 48%, 50%, 52, 55%, or at least 60%, 65%, 70%, 75%, 80%, 85%, or even at least 90%, or at least 95%, or at least 99% amino acid identity. In one aspect the ortholog is a *Cucumis melo* ortholog comprising at least least 40% amino acid sequence identity to SEQ ID NO: 14, 15, 16 or 17, e.g. at least 45%, 48%, 50%, 52%, 55%, or at least 60%, 65%, 70%, 75%, 80%, 85%, or even at least 90%, or at least 95%, or at least 99% amino acid identity.

In another aspect the invention relates to a plant of the invention (i.e. having an intense fruit phenotype due to an altered, especially reduced, amount activity or function of the endogenous AGL11-like protein ortholog) wherein the plant is of species *Cucumis sativus* and wherein the AGL11-like protein has at least 75% amino acid sequence identity to SEQ ID NO: 6, or SEQ ID NO: 7, or SEQ ID NO: 8, or SEQ ID NO: 9, e.g. at least 80%, or at least 85%, 90%, 94%, 96%, 98%, 99%, or even at least 99.2%, or at least 99.4%, 99.6%, 99.8%, or at least 99.9% amino acid identity.

In another aspect the invention relates to a plant of the invention (i.e. having an intense fruit phenotype due to an altered, especially reduced, amount activity or function of the endogenous AGL11-like protein ortholog) wherein the plant is of species *Cucumis sativus* and wherein the AGL11-like protein has at least 75% amino acid sequence identity to SEQ ID NO: 6, e.g. at least 80%, or at least 85%, 90%, 94%, 96%, 98%, 99%, or even at least 99.2%, or at least 99.4%, 99.6%, 99.8%, or at least 99.9%. Differences in sequence identity may be caused by one or more amino acid deletions, insertions or replacements compared to SEQ ID NO: 6.

In another aspect the invention relates to a plant of the invention (i.e. having an intense fruit phenotype due to an altered, especially reduced, amount activity or function of the endogenous AGL11-like protein ortholog) wherein the plant is of species *Cucumis sativus* and wherein the AGL11-like protein has at least 75% amino acid sequence identity to SEQ ID NO: 7, e.g. at least 80%, or at least 85%, 90%, 94%, 96%, 98%, 99%, or even at least 99.2%, or at least 99.4%, 99.6%, 99.8%, or at least 99.9%. Differences in sequence identity may be caused by one or more amino acid deletions, insertions or replacements compared to SEQ ID NO: 7.

In another aspect the invention relates to a plant of the invention (i.e. having an intense fruit phenotype due to an altered, especially reduced, amount activity or function of the endogenous AGL11-like protein ortholog) wherein the plant is of species *Cucumis sativus* and wherein the AGL11-like protein has at least 75% amino acid sequence identity to SEQ ID NO: 8, e.g. at least 80%, or at least 85%, 90%, 94%, 96%, 98%, 99%, or even at least 99.2%, or at least 99.4%, 99.6%, 99.8%, or at least 99.9%. Differences in sequence identity may be caused by one or more amino acid deletions, insertions or replacements compared to SEQ ID NO: 8.

In another aspect the invention relates to a plant of the invention (i.e. having an intense fruit phenotype due to an altered, especially reduced, amount activity or function of the endogenous AGL11-like protein ortholog) wherein the plant is of species *Cucumis sativus* and wherein the AGL11-like protein has at least 75% amino acid sequence identity to SEQ ID NO: 9, e.g. at least 80%, or at least 85%, 90%, 94%, 96%, 98%, 99%, or even at least 99.2%, or at least 99.4%, 99.6%, 99.8%, or at least 99.9%. Differences in sequence identity may be caused by one or more amino acid deletions, insertions or replacements compared to SEQ ID NO: 9.

In one aspect the invention relates to a plant of the invention (i.e. having an intense fruit phenotype due to an altered, especially reduced, amount activity or function of the endogenous AGL11-like protein ortholog) wherein the plant is of species *Cucumis sativus*, and wherein the modified amount, activity or function of AGL11-like protein is due to one or more mutations in the promoter or in the gene sequence of the gene encoding the AGL11-like protein as depicted in SEQ ID NO: 6, 7, 8, or 9 or encoding any one of the cucumber AGL11-like orthologs above. In one aspect the one or more mutations in the gene sequence lead to a protein comprising one or more amino acid insertions, deletions or replacements compared to the protein of SEQ ID NO: 6, 7, 8 or 9 or compared to a AGL11-like orthologous protein comprising at least 75%, 85%, 90%, 94%, 96%, 98%, 99%, or even at least 99.2%, or at least 99.4%, 99.6%, 99.8%, or at least 99.9% sequence identity to SEQ ID NO: 6, 7, 8 or 9.

In a further aspect the invention relates to a plant of the invention (i.e. having an intense fruit phenotype due to an altered, especially reduced, amount activity or function of the endogenous AGL11-like protein ortholog) wherein the plant is of species *Cucumis sativus*, and wherein the modified amount, activity or function of AGL11-like protein is due to one or more mutations in the promoter or in the gene sequence of the gene encoding the AGL11-like protein, as depicted in SEQ ID NO: 6; in another aspect the mutation is a deletion, insertion or nucleotide replacement. In yet another aspect said mutation is a deletion of at least 1 nucleotide. In yet another aspect said deletion is at least 2, or even at least 3, 5, 10, 20, 30, 40, 50, 80, 100, 150, 200, 250, 300, 350 nucleotides. In still another aspect said deletion is at least 400 nucleotides or even at least 450 or 500 nucleotides.

In a further aspect the invention relates to a plant of the invention (i.e. having an intense fruit phenotype due to an altered, especially reduced, amount activity or function of the endogenous AGL11-like protein ortholog) wherein the plant is of species *Cucumis sativus*, and wherein the modified amount, activity or function of AGL11-like protein is due to one or more mutations in the promoter or in the gene sequence of the gene encoding the AGL11-like protein, as depicted in SEQ ID NO: 7; in another aspect the mutation is a deletion, insertion or nucleotide replacement. In yet another aspect said mutation is a deletion of at least 1 nucleotide. In yet another aspect said deletion is at least 2, or even at least 3, 5, 10, 20, 30, 40, 50, 80, 100, 150, 200, 250, 300, 350 nucleotides. In still another aspect said deletion is at least 400 nucleotides or even at least 450 or 500 nucleotides.

In a further aspect the invention relates to a plant of the invention (i.e. having an intense fruit phenotype due to an altered, especially reduced, amount activity or function of the endogenous AGL11-like protein ortholog) wherein the plant is of species *Cucumis sativus*, and wherein the modified amount, activity or function of AGL11-like protein is due to one or more mutations in the promoter or in the gene sequence of the gene encoding the AGL11-like protein, as depicted in SEQ ID NO: 8; in another aspect the mutation is a deletion, insertion or nucleotide replacement. In yet another aspect said mutation is a deletion of at least 1 nucleotide. In yet another aspect said deletion is at least 2, or even at least 3, 5, 10, 20, 30, 40, 50, 80, 100, 150, 200, 250, 300, 350 nucleotides. In still another aspect said deletion is at least 400 nucleotides or even at least 450 or 500 nucleotides.

In a further aspect the invention relates to a plant of the invention (i.e. having an intense fruit phenotype due to an altered, especially reduced, amount activity or function of the endogenous AGL11-like protein ortholog) wherein the plant is of species *Cucumis sativus*, and wherein the modified amount, activity or function of AGL11-like protein is due to one or more mutations in the promoter or in the gene sequence of the gene encoding the AGL11-like protein, as depicted in SEQ ID NO: 9; in another aspect the mutation is a deletion, insertion or nucleotide replacement. In yet another aspect said mutation is a deletion of at least 1 nucleotide. In yet another aspect said deletion is at least 2, or even at least 3, 5, 10, 20, 30, 40, 50, 80, 100, 150, 200, 250, 300, 350 nucleotides. In still another aspect said deletion is at least 400 nucleotides or even at least 450 or 500 nucleotides.

In another aspect the invention relates to a plant of the invention (i.e. having an intense fruit phenotype due to an altered, especially reduced, amount activity or function of the endogenous AGL11-like protein ortholog) wherein the plant is of species *Cucumis sativus* and wherein the cDNA encoding the AGL11-like protein has at least 75% nucleic acid sequence identity to SEQ ID NO: 10, e.g at least 80%, or at least 85%, 90%, 94%, 96%, 98%, 99%, or even at least 99.2%, or at least 99.4%, 99.6%, 99.8%, or at least 99.9% nucleic acid identity.

In yet another aspect the invention relates to a plant of the invention (i.e. having an intense fruit phenotype due to an altered, especially reduced, amount activity or function of the endogenous AGL11-like protein ortholog) wherein the plant is of the species *Cucumis sativus*, and wherein the modified amount, activity or function of AGL11-like protein is due to one or more mutations in the promoter or in the gene sequence encoding the AGL11-like protein wherein the gene sequence encodes a cDNA, said cDNA has at least 75% nucleic acid sequence identity to SEQ ID NO: 10, e.g at least 80%, or at least 85%, 90%, 94%, 96%, 98%, 99%, or even at least 99.2%, or at least 99.4%, 99.6%, 99.8%, or at least 99.9% nucleic acid identity.

In another aspect the invention relates to a plant of the invention (i.e. having an intense fruit phenotype due to an altered, especially reduced, amount activity or function of the endogenous AGL11-like protein ortholog) wherein the plant is of species *Cucumis sativus* and wherein the cDNA encoding the AGL11-like protein has at least 75% nucleic acid sequence identity to SEQ ID NO: 11, e.g at least 80%, or at least 85%, 90%, 94%, 96%, 98%, 99%, or even at least 99.2%, or at least 99.4%, 99.6%, 99.8%, or at least 99.9% nucleic acid identity.

In yet another aspect the invention relates to a plant of the invention (i.e. having an intense fruit phenotype due to an altered, especially reduced, amount activity or function of the endogenous AGL11-like protein ortholog) wherein the plant is of the species *Cucumis sativus*, and wherein the modified amount, activity or function of AGL11-like protein is due to one or more mutations in the promoter or in the gene sequence encoding the AGL11-like protein wherein the gene sequence encodes a cDNA, said cDNA has at least 75% nucleic acid sequence identity to SEQ ID NO: 11, e.g at least 80%, or at least 85%, 90%, 94%, 96%, 98%, 99%, or even at least 99.2%, or at least 99.4%, 99.6%, 99.8%, or at least 99.9% nucleic acid identity.

In another aspect the invention relates to a plant of the invention (i.e. having an intense fruit phenotype due to an altered, especially reduced, amount activity or function of the endogenous AGL11-like protein ortholog) wherein the plant is of species *Cucumis sativus* and wherein the cDNA encoding the AGL11-like protein has at least 75% nucleic acid sequence identity to SEQ ID NO: 12, e.g at least 80%, or at least 85%, 90%, 94%, 96%, 98%, 99%, or even at least 99.2%, or at least 99.4%, 99.6%, 99.8%, or at least 99.9% nucleic acid identity.

In yet another aspect the invention relates to a plant of the invention (i.e. having an intense fruit phenotype due to an altered, especially reduced, amount activity or function of the endogenous AGL11-like protein ortholog) wherein the plant is of the species *Cucumis sativus*, and wherein the modified amount, activity or function of AGL11-like protein is due to one or more mutations in the promoter or in the gene sequence encoding the AGL11-like protein wherein the gene sequence encodes a cDNA, said cDNA has at least 75% nucleic acid sequence identity to SEQ ID NO: 12, e.g at least 80%, or at least 85%, 90%, 94%, 96%, 98%, 99%, or even at least 99.2%, or at least 99.4%, 99.6%, 99.8%, or at least 99.9% nucleic acid identity.

In another aspect the invention relates to a plant of the invention (i.e. having an intense fruit phenotype due to an altered, especially reduced, amount activity or function of the endogenous AGL11-like protein ortholog) wherein the plant is of species *Cucumis sativus* and wherein the cDNA encoding the AGL11-like protein has at least 75% nucleic acid sequence identity to SEQ ID NO: 13, e.g at least 80%, or at least 85%, 90%, 94%, 96%, 98%, 99%, or even at least 99.2%, or at least 99.4%, 99.6%, 99.8%, or at least 99.9% nucleic acid identity.

In yet another aspect the invention relates to a plant of the invention (i.e. having an intense fruit phenotype due to an altered, especially reduced, amount activity or function of the endogenous AGL11-like protein ortholog) wherein the plant is of the species *Cucumis sativus*, and wherein the modified amount, activity or function of AGL11-like protein is due to one or more mutations in the promoter or in the gene sequence encoding the AGL11-like protein wherein the gene sequence encodes a cDNA, said cDNA has at least 75% nucleic acid sequence identity to SEQ ID NO: 13, e.g at least 80%, or at least 85%, 90%, 94%, 96%, 98%, 99%, or even at least 99.2%, or at least 99.4%, 99.6%, 99.8%, or at least 99.9% nucleic acid identity.

In another aspect the invention relates to a plant of the invention (i.e. having an intense fruit phenotype due to an altered, especially reduced, amount activity or function of the endogenous AGL11-like protein ortholog) wherein the plant is of species *Cucumis sativus* and wherein the genomic DNA encoding the AGL11-like protein has at least 65% nucleic acid sequence identity to SEQ ID NO: 23, e.g at least 70%, 75% or 80%, or at least 85%, 90%, 94%, 96%, 98%, 99%, or even at least 99.2%, or at least 99.4%, 99.6%, 99.8%, or at least 99.9% nucleic acid identity.

In another aspect the invention relates to a plant of the invention (i.e. having an intense fruit phenotype due to an altered, especially reduced, amount activity or function of the endogenous AGL11-like protein ortholog) wherein the plant is of species *Cucumis sativus* and wherein the genomic DNA encoding the AGL11-like protein has at least 65% nucleic acid sequence identity to SEQ ID NO: 24, e.g at least 70%, 75% or 80%, or at least 85%, 90%, 94%, 96%, 98%, 99%, or even at least 99.2%, or at least 99.4%, 99.6%, 99.8%, or at least 99.9% nucleic acid identity.

In another aspect the invention relates to a plant of the invention (i.e. having an intense fruit phenotype due to an altered, especially reduced, amount activity or function of the endogenous AGL11-like protein ortholog) wherein the plant is of species *Cucumis sativus* and wherein the genomic DNA encoding the AGL11-like protein has at least 65% nucleic acid sequence identity to SEQ ID NO: 25, e.g at least 70%, 75% or 80%, or at least 85%, 90%, 94%, 96%, 98%, 99%, or even at least 99.2%, or at least 99.4%, 99.6%, 99.8%, or at least 99.9% nucleic acid identity.

In another aspect the invention relates to a plant of the invention (i.e. having an intense fruit phenotype due to an altered, especially reduced, amount activity or function of the endogenous AGL11-like protein ortholog) wherein the plant is of species *Cucumis sativus* and wherein the genomic DNA encoding the AGL11-like protein has at least 65% nucleic acid sequence identity to SEQ ID NO: 26, e.g at least 70%, 75% or 80%, or at least 85%, 90%, 94%, 96%, 98%, 99%, or even at least 99.2%, or at least 99.4%, 99.6%, 99.8%, or at least 99.9% nucleic acid identity.

In another aspect the invention relates to a plant of the invention (i.e. having an intense fruit phenotype due to an altered, especially reduced, amount activity or function of the endogenous AGL11-like protein ortholog) wherein the plant is of species *Cucumis melo* and wherein the AGL11-like protein has at least 75% amino acid sequence identity to SEQ ID NO: 14, or SEQ ID NO: 15, or SEQ ID NO: 16, or SEQ ID NO: 17, e.g. at least 80%, or at least 85%, 90%, 94%, 96%, 98%, 99%, or even at least 99.2%, or at least 99.4%, 99.6%, 99.8%, or at least 99.9% amino acid identity or encoding any one of the cucumber AGL11-like orthologs above. In one aspect the one or more mutations in the gene sequence lead to a protein comprising one or more amino acid insertions, deletions or replacements compared to the protein of SEQ ID NO: 14, 15, 16 or 17 or compared to a AGL11-like orthologous protein comprising at least 75%, 85%, 90%, 94%, 96%, 98%, 99%, or even at least 99.2%, or at least 99.4%, 99.6%, 99.8%, or at least 99.9% sequence identity to SEQ ID NO: 14, 15, 16 or 17.

In another aspect the invention relates to a plant of the invention (i.e. having an intense fruit phenotype due to an altered, especially reduced, amount activity or function of the endogenous AGL11-like protein ortholog) wherein the plant is of species *Cucumis melo* and wherein the AGL11-like protein has at least 75% amino acid sequence identity to SEQ ID NO: 14, e.g. at least 80%, or at least 85%, 90%, 94%, 96%, 98%, 99%, or even at least 99.2%, or at least 99.4%, 99.6%, 99.8%, or at least 99.9%. Differences in sequence identity may be caused by one or more amino acid deletions, insertions or replacements compared to SEQ ID NO: 14.

In another aspect the invention relates to a plant of the invention (i.e. having an intense fruit phenotype due to an altered, especially reduced, amount activity or function of the endogenous AGL11-like protein ortholog) wherein the plant is of species *Cucumis melo* and wherein the AGL11-like protein has at least 75% amino acid sequence identity to SEQ ID NO: 15, e.g. at least 80%, or at least 85%, 90%, 94%, 96%, 98%, 99%, or even at least 99.2%, or at least 99.4%, 99.6%, 99.8%, or at least 99.9%.

Differences in sequence identity may be caused by one or more amino acid deletions, insertions or replacements compared to SEQ ID NO: 15.

In another aspect the invention relates to a plant of the invention (i.e. having an intense fruit phenotype due to an altered, especially reduced, amount activity or function of the endogenous AGL11-like protein ortholog) wherein the plant is of species *Cucumis melo* and wherein the AGL11-like protein has at least 75% amino acid sequence identity to SEQ ID NO: 16, e.g. at least 80%, or at least 85%, 90%, 94%, 96%, 98%, 99%, or even at least 99.2%, or at least 99.4%, 99.6%, 99.8%, or at least 99.9%. Differences in sequence identity may be caused by one or more amino acid deletions, insertions or replacements compared to SEQ ID NO: 16.

In another aspect the invention relates to a plant of the invention (i.e. having an intense fruit phenotype due to an altered, especially reduced, amount activity or function of the endogenous AGL11-like protein ortholog) wherein the plant is of species *Cucumis melo* and wherein the AGL11-like protein has at least 75% amino acid sequence identity to SEQ ID NO: 17, e.g. at least 80%, or at least 85%, 90%, 94%, 96%, 98%, 99%, or even at least 99.2%, or at least 99.4%, 99.6%, 99.8%, or at least 99.9%. Differences in sequence identity may be caused by one or more amino acid deletions, insertions or replacements compared to SEQ ID NO: 17.

In one aspect the invention relates to a plant of the invention (i.e. having an intense fruit phenotype due to an altered, especially reduced, amount activity or function of the endogenous AGL11-like protein ortholog) wherein the plant is of species *Cucumis melo*, and wherein the modified amount, activity or function of AGL11-like protein is due to one or more mutations in the promoter or the gene sequence of the gene encoding the AGL11-like protein, as depicted in SEQ ID NO: 14, 15, 16, or 17.

In a further aspect the invention relates to a plant of the invention (i.e. having an intense fruit phenotype due to an altered, especially reduced, amount activity or function of the endogenous AGL11-like protein ortholog) wherein the plant is of species *Cucumis melo*, and wherein the modified amount, activity or function of AGL11-like protein is due to one or more mutations in the promoter or the gene sequence of the gene encoding the AGL11-like protein, as depicted in SEQ ID NO: 14; in another aspect the mutation is a deletion, insertion or nucleotide replacement. In yet another aspect said mutation is a deletion of at least 1 nucleotide. In yet another aspect said deletion is at least 2, or even at least 3, 5, 10, 20, 30, 40, 50, 80, 100, 150, 200, 250, 300, 350 nucleotides. In still another aspect said deletion is at least 400 nucleotides or even at least 450 or 500 nucleotides.

In a further aspect the invention relates to a plant of the invention (i.e. having an intense fruit phenotype due to an altered, especially reduced, amount activity or function of the endogenous AGL11-like protein ortholog) wherein the plant is of species *Cucumis melo*, and wherein the modified amount, activity or function of AGL11-like protein is due to one or more mutations in the promoter or the gene sequence encoding the gene of the AGL11-like protein, as depicted in SEQ ID NO: 15; in another aspect the mutation is a deletion, insertion or nucleotide replacement. In yet another aspect said mutation is a deletion of at least 1 nucleotide. In yet another aspect said deletion is at least 2, or even at least 3, 5, 10, 20, 30, 40, 50, 80, 100, 150, 200, 250, 300, 350 nucleotides. In still another aspect said deletion is at least 400 nucleotides or even at least 450 or 500 nucleotides.

In a further aspect the invention relates to a plant of the invention (i.e. having an intense fruit phenotype due to an altered, especially reduced, amount activity or function of the endogenous AGL11-like protein ortholog) wherein the plant is of species *Cucumis melo*, and wherein the modified amount, activity or function of AGL11-like protein is due to one or more mutations in the promoter or the gene sequence of the gene encoding the AGL11-like protein, as depicted in SEQ ID NO: 16; in another aspect the mutation is a deletion, insertion or nucleotide replacement. In yet another aspect said mutation is a deletion of at least 1 nucleotide. In yet another aspect said deletion is at least 2, or even at least 3, 5, 10, 20, 30, 40, 50, 80, 100, 150, 200, 250, 300, 350 nucleotides. In still another aspect said deletion is at least 400 nucleotides or even at least 450 or 500 nucleotides.

In a further aspect the invention relates to a plant of the invention (i.e. having an intense fruit phenotype due to an altered, especially reduced, amount activity or function of the endogenous AGL11-like protein ortholog) wherein the plant is of species *Cucumis melo*, and wherein the modified amount, activity or function of AGL11-like protein is due to one or more mutations in the promoter or the gene sequence of the gene encoding the AGL11-like protein, as depicted in SEQ ID NO: 17; in another aspect the mutation is a deletion, insertion or nucleotide replacement. In yet another aspect said mutation is a deletion of at least 1 nucleotide. In yet another aspect said deletion is at least 2, or even at least 3, 5, 10, 20, 30, 40, 50, 80, 100, 150, 200, 250, 300, 350 nucleotides. In still another aspect said deletion is at least 400 nucleotides or even at least 450 or 500 nucleotides.

In another aspect the invention relates to a plant of the invention (i.e. having an intense fruit phenotype due to an altered, especially reduced, amount activity or function of the endogenous AGL11-like protein ortholog) wherein the plant is of species *Cucumis melo* and wherein the cDNA encoding the AGL11-like protein has at least 75% nucleic acid sequence identity to SEQ ID NO: 18, e.g at least 80%, or at least 85%, 90%, 94%, 96%, 98%, 99%, or even at least 99.2%, or at least 99.4%, 99.6%, 99.8%, or at least 99.9% nucleic acid identity.

In yet another aspect the invention relates to a plant of the invention (i.e. having an intense fruit phenotype due to an altered, especially reduced, amount activity or function of the endogenous AGL11-like protein ortholog) wherein the plant is of the species *Cucumis melo*, and wherein the modified amount, activity or function of AGL11-like protein is due to one or more mutations in the promoter or the gene sequence encoding the AGL11-like protein wherein the gene sequence encodes a cDNA, said cDNA has at least 75% nucleic acid sequence identity to SEQ ID NO: 18, e.g at least 80%, or at least 85%, 90%, 94%, 96%, 98%, 99%, or even at least 99.2%, or at least 99.4%, 99.6%, 99.8%, or at least 99.9% nucleic acid identity.

In another aspect the invention relates to a plant of the invention (i.e. having an intense fruit phenotype due to an altered, especially reduced, amount activity or function of the endogenous AGL11-like protein ortholog) wherein the plant is of species *Cucumis melo* and wherein the cDNA encoding the AGL11-like protein has at least 75% nucleic acid sequence identity to SEQ ID NO: 19, e.g at least 80%, or at least 85%, 90%, 94%, 96%, 98%, 99%, or even at least 99.2%, or at least 99.4%, 99.6%, 99.8%, or at least 99.9% nucleic acid identity.

In yet another aspect the invention relates to a plant of the invention (i.e. having an intense fruit phenotype due to an altered, especially reduced, amount activity or function of the endogenous AGL11-like protein ortholog) wherein the plant is of the species *Cucumis melo*, and wherein the modified amount, activity or function of AGL11-like protein is due to one or more mutations in the promoter or the gene sequence encoding the AGL11-like protein wherein the gene sequence encodes a cDNA, said cDNA has at least 75% nucleic acid sequence identity to SEQ ID NO: 19, e.g at least 80%, or at least 85%, 90%, 94%, 96%, 98%, 99%, or even at least 99.2%, or at least 99.4%, 99.6%, 99.8%, or at least 99.9% nucleic acid identity.

In another aspect the invention relates to a plant of the invention (i.e. having an intense fruit phenotype due to an altered, especially reduced, amount activity or function of the endogenous AGL11-like protein ortholog) wherein the plant is of species *Cucumis melo* and wherein the cDNA encoding the AGL11-like protein has at least 75% nucleic acid sequence identity to SEQ ID NO: 21, e.g at least 80%, or at least 85%, 90%, 94%, 96%, 98%, 99%, or even at least 99.2%, or at least 99.4%, 99.6%, 99.8%, or at least 99.9% nucleic acid identity.

In yet another aspect the invention relates to a plant of the invention (i.e. having an intense fruit phenotype due to an altered, especially reduced, amount activity or function of the endogenous AGL11-like protein ortholog) wherein the plant is of the species *Cucumis melo*, and wherein the modified amount, activity or function of AGL11-like protein is due to one or more mutations in the promoter or the gene sequence encoding the AGL11-like protein wherein the gene sequence encodes a cDNA, said cDNA has at least 75% nucleic acid sequence identity to SEQ ID NO: 21, e.g at least 80%, or at least 85%, 90%, 94%, 96%, 98%, 99%, or even at least 99.2%, or at least 99.4%, 99.6%, 99.8%, or at least 99.9% nucleic acid identity.

In another aspect the invention relates to a plant of the invention (i.e. having an intense fruit phenotype due to an altered, especially reduced, amount activity or function of the endogenous AGL11-like protein ortholog) wherein the plant is of species *Cucumis melo* and wherein the cDNA encoding the AGL11-like protein has at least 75% nucleic acid sequence identity to SEQ ID NO: 22, e.g at least 80%, or at least 85%, 90%, 94%, 96%, 98%, 99%, or even at least 99.2%, or at least 99.4%, 99.6%, 99.8%, or at least 99.9% nucleic acid identity.

In yet another aspect the invention relates to a plant of the invention (i.e. having an intense fruit phenotype due to an altered, especially reduced, amount activity or function of the endogenous AGL11-like protein ortholog) wherein the plant is of the species *Cucumis melo*, and wherein the modified amount, activity or function of AGL11-like protein is due to one or more mutations in the promoter or the gene sequence encoding the AGL11-like protein wherein the gene sequence encodes a cDNA, said cDNA has at least 75% nucleic acid sequence identity to SEQ ID NO: 22, e.g at least 80%, or at least 85%, 90%, 94%, 96%, 98%, 99%, or even at least 99.2%, or at least 99.4%, 99.6%, 99.8%, or at least 99.9% nucleic acid identity.

In one aspect, the one or more mutations in the AGL11-like ortholog gene and/or promoter are human induced mutations. In a further aspect the gene, protein and/or promoter is isolated, i.e. is no longer in the natural environment from which it is isolated. In still another aspect the invention relates to seed from which a plant of the invention can be grown.

In one aspect the invention relates to a plant cell, tissue or plant part of the plant of the invention; in one embodiment the plant part is a seed. In another aspect the invention relates to a plant cell of the plant of the invention. In yet another aspect the invention relates to a non-propagating cell of a plant of the invention.

In another aspect the invention relates to a plant cell, tissue or plant part of a seed from which a plant of the invention can be grown. In yet another aspect the invention relates to a non-propagating part of a seed from which a plant of the invention can be grown.

In one aspect the invention relates to a fruit from a plant of the invention. In another aspect the invention relates to a part of a fruit from a plant of the invention. In still another aspect the fruit from the plant of the invention has essentially no gel in the seed cavities. In yet another aspect the fruit from the plant of the invention has an intense fruit phenotype.

The inventors of the current application surprisingly found that plants of species *Solanum lycopersicum* having a deletion in the promoter of the Tomato AGL11-like gene sequence produced intense phenotype tomato fruits. This now allows for screening for mutant AGL11-like protein or cDNA sequences or promoter sequences thereof. SEQ ID NO: 1 can be used as a marker to identify plants with a normal fruit phenotype.

SEQ ID NO: 2 and 20 can be used as a marker to identify tomato plants with an intense phenotype. When used as a marker, the complete sequence of SEQ ID NO: 2 or 20 can be used, or a part of the sequence. When a part of the sequence is used, the part must be long enough to prevent false positives when screening for occurrence of the sequence, the part should for example be at least 5 consecutive nucleic acids long, e.g. at least 6, 7, 8, 9, 10, 11, 12, 13, 14, 15, 16, 20, 25, 30, 40, or 50 consecutive nucleic acids long. In one embodiment the sequence is at least 15 nucleic acids long. False positives can be prevented by verifying if the marker sequence occurs in tomato plants having a normal fruit phenotype.

In one aspect the invention relates to the use of SEQ ID NO: 1 or SEQ ID NO: 2 or SEQ ID NO: 20 or parts thereof as a marker for the identification of the intense phenotype in *Solanum lycopersicum*. In another aspect the invention relates to SEQ ID NO: 1 or parts thereof as a marker for the identification of the intense phenotype in *Solanum lycopersicum*. In another aspect the invention relates to SEQ ID NO: 2 or parts thereof as a marker for the identification of the intense phenotype in *Solanum lycopersicum*. In another aspect the invention relates to SEQ ID NO: 20 or parts thereof as a marker for the identification of the intense phenotype in *Solanum lycopersicum*. When using parts of SEQ ID NO:20 as a marker, especially those parts that do not occur as a consecutive sequence part in SEQ ID NO: 1 are of interest as they can be used to identify plants with intense fruit phenotype; e.g. parts that comprise both the A located 637 nucleotides before ATG start codon, and the A located 1043 nucleotides before the ATG start codon in FIG. 3, can be used as a markers.

In a further aspect the invention relates to a process to identify *Solanum lycopersicum* plants having an intense fruit phenotype, said process comprising the use of SEQ ID NO: 1, 2, or 20 or parts thereof.

In still a further aspect the invention relates to a method to identify *Solanum lycopersicum* plants having an normal fruit phenotype, said method comprising the use of SEQ ID NO: 2, or parts thereof. In this method the presence of SEQ ID NO: 2 is established to confirm normal fruit phenotype.

In still another aspect the invention relates to a method of producing *Solanum lycopersicum* plants comprising step a) selecting a tomato plant using SEQ ID NO: 2 or parts thereof; or SEQ ID NO:
20 or parts thereof.

In another aspect the invention relates to a method for producing *Solanum lycopersicum* plants comprising an intense fruit phenotype comprising steps:
a. selecting a tomato plant using SEQ ID NO: 2 or parts thereof; or SEQ ID NO: 20 or parts thereof;
b. crossing said tomato plant with a second tomato plant; said second tomato plant optionally being selected using SEQ ID NO: 2 or parts thereof; or SEQ ID NO: 20 or parts thereof; and
c. optionally selecting progeny plants using SEQ ID NO: 2 or parts thereof; or SEQ ID NO: 20 or parts thereof.

As indicated above, the intense fruit phenotype in *Solanum lycopersicum* is caused by a mutation on chromosome 6. Chromosome 6 is known to have many loci of relevance to tomato breeders (e.g. PCT/EP2013/055044). Making plants with combinations of traits, the genes of which lying on one chromosome is a challenging task for plant breeders. Especially when no markers for the traits of interest are present, the breeder needs to grow full plants and determine if the desired phenotype is present in the plant. The current invention allows for a rapid screening of plants with an intense fruit phenotype already on young plants or seedling stage. This is especially useful when different loci need to be combined on chromosome 6.

The recessive allelic mutation old-gold-crimson (ogc) has a phenotype of deep red fruits that lack β-carotene and tawny orange flowers. The locus ogc previously was found to be on chromosome 6 of the tomato linkage map (Ronen et al, PNAS 2000, vol 97 pp 11102-11107).

Tomato powdery mildew caused by *Oidium neolycopersici* is a globally important disease of tomato (*Lycopersicon esculentum*). Bai et al described an integrated genetic map showing that all the dominant resistance genes (Ol-1, Ol-3, Ol-4, Ol-5, and Ol-6) are located on tomato chromosome 6 (Bai et al 2005 Molecular Plant-Microbe Interactions vol 18, pp 354-362).

In another aspect the invention relates to a method for producing *Solanum lycopersicum* plants comprising an intense fruit phenotype and having the ogc phenotype comprising steps:
a. providing a tomato plant comprising at least one recombinant chromosome 6 having the intense allele and the ogc allele as found in seeds deposited under accession number NCIMB 42161 or a recombinant chromosome 6 obtained (or derived) therefrom;
b. crossing said tomato plant with a second tomato plant; and
c. optionally selecting progeny plants.
In yet another aspect the invention relates to a plant obtainable by this method.

In another aspect the invention relates to a method for producing *Solanum lycopersicum* plants comprising an intense fruit phenotype and having the ogc phenotype and resistance to powdery mildew comprising steps:
a. providing a tomato plant comprising at least one recombinant chromosome 6 having the intense allele, the ogc allele and Ol-6 allele as found in seeds deposited under accession number NCIMB 42162 or a recombinant chromosome 6 obtained (or derived) therefrom;
b. crossing said tomato plant with a second tomato plant; and
c. optionally selecting progeny plants.

In yet another aspect the invention relates to a plant obtainable by this method.

In another aspect the invention relates to a method for producing *Solanum lycopersicum* plants comprising an intense fruit phenotype and having the ogc phenotype comprising steps:
a. providing a tomato plant comprising at least one recombinant chromosome 6 having the intense allele and the ogc allele as found in seeds deposited under accession number NCIMB 42161 or NCIMB 42162 or a recombinant chromosome 6 obtained (or derived) from either of these two deposited lines;
b. crossing said tomato plant with a second tomato plant; and
c. optionally selecting progeny plants.

In yet another aspect the invention relates to a plant obtainable by this method.

In still another aspect the invention relates to a cultivated plant of the species *Solanum lycopersicum* comprising an intense fruit phenotype and ogc phenotype.

In yet another aspect the invention relates to a cultivated plant of the species *Solanum lycopersicum* comprising an intense fruit phenotype, ogc phenotype and powdery mildew resistance.

In one aspect the invention relates to a tomato plant obtainable by crossing a plant of the invention e.g. as deposited under accession number NCIMB 42161 or NCIMB 42162 with another tomato plant.

In one aspect the invention relates to a *Solanum lycopersicum* plant comprising a recombinant chromosome 6 comprising SEQ ID NO: 20 and allele conferring ogc and/or powdery mildew resistance. In another aspect the invention relates to a *Solanum lycopersicum* plant comprising a recombinant chromosome 6 comprising SEQ ID NO: 20 and allele conferring ogc and/or an Ol-6 allele conferring resistance against powdery mildew.

In another aspect the invention relates to a method of producing plants comprising:
a. providing a plant according to the invention;
b. crossing and/or selfing said plant with another plant;
c. collect seed of the crossing or selfing;
d. optionally selecting progeny plants.

In yet another aspect this method is a method to produce *Solanum lycopersicum* plants and at least one of the plants of step a or b is comprises the recombinant chromosome 6 as found in seeds deposited under NCIMB 42161 or NCIMB 42162 or a recombinant chromosome 6 obtained (or derived) therefrom. In still another aspect the invention relates to seeds or plants obtained by using this method.

In one aspect of the invention the recombinant chromosome (e.g. chromosome 6 in *Solanum lycopersicum* or a chromosome comprising the AGL11-like ortholog sequence) is a human induced recombinant chromosome.

Fruits harvested from a plant of the invention are also an embodiment. Such fruits thus have an intense phenotype. In one aspect such fruits are tomato fruits comprising a recombinant chromosome 6 according to the invention. The tomato fruits may be of any color (yellow, pink, red, orange, white, purple, black, multicolored, striped, etc.), shape (round, oblong, elongated, pear, etc.) and size (cherry, micro, mini, beefsteak, grape, slicing or globe, plum, pear, etc.). The fruits may be bi-loculate or multi-loculate types. The fruits may be suitable for fresh markets or processing. As the fruits have an intense phenotype, they are particularly suited for sandwiches and salads. Also included are food- or feed products comprising fruits or parts of fruits according to the invention, such as diced fruits, sliced fruits, chopped, fruits, dried fruits, processed fruits (tomato paste, puree, soups, juice, sauces, ketchup, etc.), canned fruits, etc.

In one embodiment the invention relates to a method of identifying a mutant of AGL11-like protein or orthologs thereof comprising the steps of:
i. taking a sample from a plant of the invention (e.g. a *Solarium lycopersicum* or Cucurbiteae plant;
ii. determine the gene sequence of the AGL11-like protein or ortholog thereof; and or the promoter of said gene sequence;
iii. optionally compare the sequence of step b) with a reference sequence. Such reference sequence for *Solanum lycopersicum* can be a sequence as represented by SEQ ID NO: 1, 2, 4, 5, 20, or parts thereof; for *Cucumis sativus* can be a sequence as represented by SEQ ID NO: 10, 11, 12, 13, or parts thereof; for *Cucumis melo* can be a sequence as represented by SEQ ID NO: 18, 19, 21, 22, or parts thereof. In another embodiment, such reference sequence can be selected from the group consisting of SEQ ID NO: 2, 5, 20, 10, 11, 12, 13 18, 19, 21, and 22; or parts thereof. In yet another embodiment, the method comprises a further step iv) of determine if the fruits of the plant of step i) have an intense fruit phenotype.

Accessions of wild tomato relatives, such as accessions obtainable from the TGRC (Tomato Genetic Resource Center) or other seed collections, can be screened for powdery mildew resistance using phenotypic and/or Ol-6 markers assays, and/or Ol-6 ortholog marker assays. These wild accessions can also be screened for ogc phenotype using phenotypic assays. Accessions of interest (having resistance and/or ogc phenotype) can be crossed with a *Solanum lycopersicum* plant comprising an intense allele in heterozygous or homozygous form. The F2 generation (or further generation, such as the F3 or a backcross generation) can then be screened for recombinant plants having the combination of intense fruit phenotype and ogc phenotype and optionally powdery mildew resistance. This combination will only be found if the *Solarium lycopersicum* chromosome 6 (comprising the intense allele) has recombined with the chromosome 6 comprising the ogc and/or Ol-6 allele.

In one embodiment a tomato plant is provided which comprises two homologous recombinant chromosomes 6, each with the intense and ogc allele; or in another embodiment each with the intense, ogc and Ol-6 allele. In one embodiment the two homologous recombinant chromosomes 6 are identical, whereby the introgression fragments are of the same size and origin and comprise the same intense and ogc allele and optionally the same Ol-6 resistance conferring allele. A tomato plant with such identical chromosomes can be generated by selfing and selecting homozygous progeny plants. In another embodiment the two homologous recombinant chromosomes may be different, e.g. one may comprise a shorter introgression fragment than the other.

In an embodiment the plants of the invention are F1 hybrids, produced by crossing two parent plants, P1 and P2 each being homozygous for chromosomes 6.

Tomato plants having the intense phenotype and the ogc phenotype can be generated by crossing a tomato plant (*Solanum lycopersicum*) comprising the intense allele or, preferably, comprising the intense phenotype (i.e. homozygous for the intense allele); with a plant comprising ogc phenotype (i.e. comprising ogc allele on chromosome 6) and selecting recombinant plants in the progeny generations which have both the intense and ogc phenotype. Plants with both the intense and ogc phenotype can be crossed with a plant comprising powdery mildew resistance (i.e. comprising Ol-6 allele on chromosome 6, preferably in homozygous form); and selecting recombinant plants in the progeny generations which have both the intense and ogc phenotype and are powdery mildew resistant.

Plants having the intense phenotype are commercially available, e.g. varieties sold by Nunhems B.V. under the trade name Intense™. The phenotype is easily recognized and selected for by allowing mature tomato fruits to develop, cutting these in half and visually determining whether the phenotype is "intense" or "normal", i.e. essentially without gel in the seed cavities or with gel in the seed cavities of the fruit, as seen e.g. in FIG. 1 (the right fruit has the "intense phenotype" and left fruit has a "normal phenotype", i.e. a non-intense phenotype). Alternatively, plants with intense fruit phenotype can be selected using (part of) SEQ ID NO: 2 or 20. It is noted that the development of air-cavities ("puffy" fruit) can also develop in intense fruits. Puffy-ness is a problem caused by factors affecting fruit set (such as temperature). Yet, the intense fruit will be equally easy be distinguishable from the normal fruit phenotype, as no locular gel is present. "Essentially no gel" or "essentially without gel" in the seed cavities means in one aspect that the tomato fruits comprise on average seed cavities with at least 98% fleshy tissue and at most 2% gel, more preferably at least 99% fleshy tissue and at most 1% locular gel, most preferably 100% fleshy tissue and no locular gel.

Plants with powdery mildew resistance conferred by the Ol-6 allele are commercially available e.g. variety Foose sold by Syngenta. The phenotype is easily recognized and selected for using the Ol-6 resistance test as described herein. Alternatively, molecular markers can be generated for this allele to identify the allele in young plants.

Plants comprising ogc phenotype are commercially available. Alternatively, plants comprising ogc phenotype can be wild relatives of tomato, or preferably *Solanum lycopersicum* plants comprising an introgression fragment on chromosome 6 from such a wild relative of tomato.

Thus, after a cross has been made between a tomato plant having an intense phenotype and a tomato plant having a ogc phenotype conferred by an introgession fragment on chromosome 6, a large number of progeny needs to be screened in order to identify the very rare recombinant plant, having both the intense phenotype and the ogc phenotype. It is understood that appropriate control plants are preferably included in any such test (field or greenhouse), such as *S. lycopersicum* plants having an intense fruit phenotype, plants having a normal fruit phenotype (e.g. cv Moneymaker), plants with ogc phenotype and 'normal" plants (such as cv Moneymaker).

It is known in the art that to observe a recessive trait phenotype, like ogc or intense, one must generate a F2 population in order to be able to observe the phenotype, as two copies of the recessive allele need to be present in the plant of interest.

Progeny plants can, for example, be of the F2, F3, F4, BC1, BC2, BC1S1, BC1S2, etc. generations. As mentioned above, the intense phenotype is screened by visual assessment of the mature fruits or using SEQ ID NO: 1, 2 or 20 or parts thereof.

Once a progeny plant has been identified which comprises both the intense fruit phenotype and ogc phenotype, this plant is selected for further analysis and use, for example to generate tomato plants comprising intense fruit phenotype and ogc phenotype and powdery mildew resistance. A tomato plant having the intense phenotype and ogc phenotype can only arise through a rare chromosome cross-over event of homologous chromosomes 6, in between the intense locus and the ogc locus. Without such a rare recombination event, plants have either an intense phenotype, but have non-ogc phenotype (normal skin), or have a normal fruit phenotype and have ogc phenotype.

A combination of 3 different traits, all with alleles on tomato chromosome 6, e.g. intense, ogc, and Ol-6, can be made by first generating a plant with an intense and ogc phenotype after crossing this plant with another plant having the Ol-6 allele of interest the progeny of this cross can be screened for the desired combination of 3 traits. Alternatively, one can start by making the combination of intense with Ol-6 and add ogc afterwards, or first make the an Ol-6 and ogc phenotype combination after which this can be crossed with another plant having the intense phenotype.

"About 25% of plants" and "about 50% of plants" is well understood by the skilled person having knowledge of genetics and heredity as referring to Mendelian segregation of a certain characteristic. In a population of 1000 plants segregating for a certain characteristic in a 1:2:1 ratio, i.e. about 25%:about 50%:about 25% of plants, it is understood that it is not necessary that exactly 250, 500 and 250 plants have the described phenotypes or genotype, but that statistically about 25%, 50% and 25% are of the mentioned phenotypes or genotypes.

In one embodiment marker analysis involves extracting DNA from plant tissue of a plant comprising an intense fruit phenotype, using said DNA as template in a PCR reaction with primer pairs suitable to show the deletion of SEQ ID NO:2 in the wild type tomato promoter sequence (of SEQ ID NO: 1), restriction of the amplified DNA with a restriction enzyme, separating the digested DNA fragments on an agarose gel and visualizing the digested fragments under UV light (as known in the art, e.g. as described by Verlaan et al. 2011, Plant Journal 68: 1093-1103). One or more of these markers can thus be used to determine whether the tomato plant comprises the deletion in the promoter sequence of TAGL11-like allele, in order to confirm the presence of the introgression fragment in recombinant plants and optionally the size of the introgression fragment. Obviously, markers can be developed using methods known in the art.

The markers can also be used to transfer a recombinant chromosome 6 (from e.g. a plant having an intense and ogc phenotype and optionally powdery mildew resistance) into progeny plants, i.e. to select progeny plants for the presence/retention of the recombinant chromosome 6. The markers, or alternative markers, can thus be easily used in breeding, in order to select plants having a recombinant chromosome 6 according to the invention. However, as already mentioned, phenotypic selection of the phenotype and resistance profile of interest can equally or additionally be used.

In one embodiment the plant of the invention is a transgenic plant comprising a modified amount, activity or function of AGL11-like protein, wherein the plant is a member of plant family Cucurbitaceae or of species *Solanum lycopersicum*. In another embodiment the transgenic plant is characterized in that the plant is not a *Solanum lycopersicum* plant having a deletion from nucleotide 1042 to nucleotide 637 of SEQ ID NO: 1, counting the A of the ATG start codon as nucleotide I (see FIG. 3).

In a further embodiment, seeds and containers comprising seeds from which plants according to the invention can be grown are provided.

Also plants grown from said seeds and having an intense fruit phenotype are provided. The plants may be determinate or indeterminate or semi-determinate. The intense phenotype according to the invention can easily be introduced into any plant of the same species by crossing and phenotypic and/or marker selection. The intense phenotype can thus be combined with other genes and genomes of *S. lycopersicum* or Cucurbitaea. For example, other disease or insect resistance genes, genes for fruit quality characteristics, fruit size, plant or fruit uniformity, plant size, flowering characteristics, fruit shape, taste, stress tolerance, fruit texture, fruit lycopene, beta-carotene or vitamin content, total soluble solids content (brix), long shelf life, etc.

In one embodiment the plant of the invention is a cultivated tomato of the species *S. lycopersicum*, i.e. a line or variety yielding high yields, such as fruit of at least 40 or 50 g average fresh weight or more, e.g. at least about 80 g, 90 g, 100 g, 120 g, 150 g, 200 g, 250 g, 300 g, or even up to 600 g (beef tomato types). However, also small types, such as cherry or cocktail tomato are encompassed (having e.g. fruit weights of 30 g or less, such as 25 g, 15 g, 12 g or less). The fruits may be Roma type, cluster type, round, etc. It may be a processing type tomato or a fresh market type. Also both open pollinated and hybrids are encompassed herein. In one embodiment the tomato plant is an F1 hybrid plant, grown from an F1 hybrid seed. In another embodiment the tomato plant is an inbred parent line, suitable as a parent in F1 hybrid seed production. In one embodiment the tomato plant comprises only one recombinant chromosome 6 according to the invention, while in another embodiment the tomato plant comprises two recombinant chromosomes 6 (which may be identical chromosomes or different). The tomato plant may also be a double haploid plant (DH), produced from a cell- or tissue culture of a plant according to the invention, whereby the DH plant comprises two identical recombinant chromosomes 6 of the invention.

Also vegetatively propagated plants are encompassed herein, for example plants produced from cuttings of a tomato (or melon or cucumber) plant of the invention. Tomato plants are easily vegetatively propagated by taking cuttings, allowing these to develop roots and growing a whole plant. The vegetatively propagated plant is genetically identical to the plant part (cutting) which was used to start with.

In a further aspect a method of introducing a desired trait into a plant of the invention is provided, said method comprising: (a) crossing a plant of the invention with another tomato plant that comprises one or more desired traits, to produce F1 progeny plants; (b) optionally selfing the F1 progeny plants one or more times to produce an F2, or F3, or further generation progeny plants; (c)

selecting from said progeny plants those plants that have the intense fruit phenotype and the desired trait; (d) optionally, backcrossing the selected progeny plants with the parent plant of a) to produce backcross progeny plants; (e) optionally, selecting for backcross progeny plants that have the intense phenotype and the desired trait; (f) optionally, repeating steps (d) and (e) one, two or more times in succession to produce selected third or higher backcross progeny plants; (g)

optionally, selfing selected backcross progeny in order to identify homozygous plants comprising the intense phenotype and the desired trait; (h) optionally, crossing at least one of said backcross progeny or selfed plants with another parent plant to generate a hybrid variety with the desired trait and an intense phenotype. The desired trait may be any trait, but is in one embodiment a trait not located the same chromosome as the intense allele (i.e. chromosome 6 in tomato). The desired trait may be a trait conferring any of the characteristics mentioned further above, such as high brix, disease or insect resistance, fruit shape, color, plant size, flowering characteristics, herbicide resistance, etc. The desired trait may also be a transgenic trait, conferred by a transgene, such as a transgene encoding a *Bacillus thuringiensis* endotoxin or part thereof, a transgene conferring herbicide resistance (against e.g. glufosinate, glyphosate, imidazolinone, triazine, sulfonylurea), etc.

A tomato plant comprising a recombinant chromosome 6 obtainable from seed deposited under Accession number NCIMB 42161 or NCIMB 42612 is also encompassed herein as is the recombinant chromosome 6 as such and its use in generating tomato plants having intense fruit phenotype.

Also provided is a tomato plant, or part thereof, a representative sample of seeds of which having been deposited under Accession Number NCIMB 42162 or NCIMB 42162.

Also provided is a tomato seed, a representative sample of seeds having been deposited under Accession Number NCIMB 42161 or NCIMB 42612 and a plant, or a part thereof, produced by growing the seed. In another aspect a progeny plant of tomato variety deposited under Accession Number NCIMB 42161 or NCIMB 42162 is provided, obtained by further breeding with said variety, wherein said progeny plant has essentially all physiological and morphological characteristics of the tomato variety (of which seeds have been deposited under NCIMB 42161 or NCIMB 42612) when grown under the same environmental conditions.

In yet a further embodiment a transgenic plant (or plant seed, plant cell, plant part) is provided comprising a modified amount, activity or function of AGL11-like protein, wherein the plant is a member of plant family Cucurbitaceae or of species *Solanum lycopersicum*; characterized in that the plant is not a *Solanum lycopersicum* plant having a deletion from nucleotide 1042 to nucleotide 637 upstream of the ATG start codon of SEQ ID NO: 1 (see FIG. 3).

TILLING (Targeting Induced Local Lesions IN Genomes) is a general reverse genetics technique that uses traditional chemical mutagenesis methods to create libraries of mutagenized individuals that are later subjected to high throughput screens for the discovery of mutations. TILLING combines chemical mutagenesis with mutation screens of pooled PCR products, resulting in the isolation of missense and non-sense mutant alleles of the targeted genes. Thus, TILLING uses traditional chemical mutagenesis (e.g. EMS or MNU mutagenesis) or other mutagenesis methods (e.g. radiation such as UV) followed by high-throughput screening for mutations in specific target genes, such as AGL11-like according to the invention. S1 nucleases, such as CEL1 or ENDO1, are used to cleave heteroduplexes of mutant and wild type target DNA and detection of cleavage products using e.g. electrophoresis such as a LI-COR gel analyzer system, see e.g. Henikoff et al. Plant Physiology 2004, 135: 630-636. TILLING has been applied in many plant species, such as tomato. (see http://tilling.ucdavis.edu/index.php/Tomato_Tilling), rice (Till et al. 2007, BMC Plant Biol 7: 19), Arabidopsis (Till et al. 2006, Methods Mol Biol 323: 127-35), -Brassica, maize (Till et al. 2004, BMC Plant Biol 4: 12), etc. Also EcoTILLING, whereby mutants in natural populations are detected, has been widely used, see Till et al. 2006 (Nat Protoc 1: 2465-77) and Comai et al. 2004 (Plant J 37: 778-86).

In one embodiment of the invention (cDNA or genomic) nucleic acid sequences encoding such mutant AGL11-like proteins comprise one or more non-sense and/or missense mutations, e.g. transitions (replacement of purine with another purine (A↔G) or pyrimidine with another pyrimidine (C↔T)) or transversions (replacement of purine with pyrimidine, or vice versa (C/T↔A/G). In one embodiment the non-sense and/or missense mutation(s) is/are in the nucleotide sequence encoding any of the Myb12 exons, or an essentially similar domain of a variant AGL11-like protein, i.e. in a domain comprising at least 80%, 90%, 95%, 98%, 99% amino acid sequence identity to amino acids of SEQ ID NO: 3 or at least 80%, 90%, 95%, 98%, 99% amino acid sequence identity to amino acids of SEQ ID NO: 6 or at least 80%, 90%, 95%, 98%, 99% amino acid sequence identity to amino acids of SEQ ID NO: 7 or at least 80%, 90%, 95%, 98%, 99% amino acid sequence identity to amino acids of SEQ ID NO: 8 or at least 80%, 90%, 95%, 98%, 99% amino acid sequence identity to amino acids of SEQ ID NO: 8 or at least 80%, 90%, 95%, 98%, 99% amino acid sequence identity to amino acids of SEQ ID NO: 14 or at least 80%, 90%, 95%, 98%, 99% amino acid sequence identity to amino acids of SEQ ID NO: 15 or at least 80%, 90%, 95%, 98%, 99% amino acid sequence identity to amino acids of SEQ ID NO: 16 or at least 80%, 90%, 95%, 98%, 99% amino acid sequence identity to amino acids of SEQ ID NO: 3 or at least 80%, 90%, 95%, 98%, 99% amino acid sequence identity to amino acids of SEQ ID NO: 17.

In one embodiment an agl11-like nucleotide sequence comprising one or more non-sense and/or missense mutations in one of the exon-encoding sequence are provided, as well as a plant comprising such a mutant allele resulting in intense fruit phenotype.

In a specific embodiment of the invention plants and plant parts (fruits, seeds, etc.) comprising a mutant loss-of-function or reduced-function agl11-like allele according to the invention are provided.

Also provided are nucleic acid sequences (genomic DNA, cDNA, RNA) encoding loss-of-function agl11-like protein or reduced-function agl11-like proteins. Due to the degeneracy of the genetic code various nucleic acid sequences may encode the same amino acid sequence.

It is understood that when sequences are depicted as DNA sequences while RNA is referred to, the actual base sequence of the RNA molecule is identical with the difference that thymine (T) is replace by uracil (U). When referring herein to nucleotide sequences (e.g DNA or RNA) italics are used, e.g. myb12 allele, while when referring to proteins, no italics are used, e.g. myb12 protein. Mutants are in small letters (e.g agl11-like allele or agl11-like protein), while wild type/functional forms start with a capital letter (Agl11-like allele or Agl11-like protein).

Also provided are nucleic acid sequences (genomic DNA, cDNA, RNA) encoding mutant agl11-like proteins, i.e. loss-of-function agl11-like protein or reduced function agl11-like proteins, as described above, and plants and plant parts comprising such mutant sequences. For example, agl11-like nucleic acid sequences comprising one or more non-sense and/or missense mutations in the wild type Agl11-like coding sequence, rendering the encoded protein having a loss-of-function or reduced function in vivo. Also sequences with other mutations are provided, such as splice-site mutants, i.e. mutations in the genomic agl11-like sequence leading to aberrant splicing of the pre-mRNA, and/or frame-shift mutations, and/or insertions (e.g. transposon insertions) and/or deletions of one or more nucleic acids.

Also included are variants and fragments of agl11-like nucleic acid sequences, such as nucleic acid sequences hybridizing to AGL11-like nucleic acid sequences, e.g. to SEQ ID NO: 4, 10, 11, 12, 13, 18, 19, 21, or 22 under stringent hybridization conditions as defined. Variants of AGL11-like nucleic acid sequences also include nucleic acid sequences which have a sequence identity to SEQ ID NO: 4, 10, 11, 12, 13, 18, 19, 21, or 22 of at least 50% or more, preferably at least 55%, 60%, 70%, 80%, 85%, 90%, 95%, 98%, 99% or more (as determined by Emboss "needle" using default parameters, i.e. gap creation penalty=10, gap extension penalty=0.5, scoring matrix nwsgapdna).

It is clear that many methods can be used to identify, synthesise or isolate variants or fragments of agl11-like nucleic acid sequences, such as nucleic acid hybridization, PCR technology, in silico analysis and nucleic acid synthesis, and the like. Variants of SEQ ID NO: 4, 10, 11, 12, 13, 18, 19, 21, or 22, may either encode wild type, functional Agl11-like proteins, or they may encode loss-of-function agl11-like protein or reduced-function mutant alleles of any of these, as for example generated e.g. by mutagenesis and/or identified by methods such as TILLING or EcoTILLING, or other methods.

A plant of the invention can be used in a conventional plant breeding scheme to produce more plants with the same characteristics or to introduce the mutated agl11-like allele into other plant lines or varieties of the same or related plant species.

In another embodiment, the plant comprising the mutant agl11-like allele (e.g. tomato) is crossed with another plant of the same species or of a closely related species, to generate a hybrid plant (or hybrid seed) comprising the mutant agl11-like allele. Such a hybrid plant is also an embodiment of the invention.

Also a method for transferring traits from a plant of the invention to another plant is provided, comprising providing a plant of the invention, crossing said plant with another plant and obtaining the seeds of said cross. Optionally plants obtained from these seeds may be further selfed and/or crossed and progeny selected comprising the desired trait.

As mentioned, it is understood that other mutagenesis and/or selection methods may equally be used to generate mutant plants according to the invention. Seeds may for example be radiated or chemically treated to generate mutant populations. Also direct gene sequencing of agl11-like may be used to screen mutagenized plant populations for mutant alleles. For example KeyPoint screening is a sequence based method which can be used to identify plants comprising mutant myb12 alleles (Rigola et al. PloS One, March 2009, Vol 4(3):e4761).

Thus, non-transgenic mutant plant comprising a modified amount, activity or function of AGL11-like protein, wherein the plant is a member of plant family Cucurbitaceae or of species *Solanum lycopersicum*; characterized in that the plant is not a *Solanum lycopersicum* plant having a deletion from nucleotide 1042 to nucleotide 637 upstream of the ATG start codon of SEQ ID NO: 1 (See also FIG. 3) are provided. These mutants may be generated by mutagenesis methods, such as TILLING or variants thereof, or they may be identified by EcoTILLING or by any other method. Agl11-like alleles encoding loss-of-function Agl11-like protein or reduced-functional Agl11-like protein may be isolated and sequenced or may be transferred to other plants by traditional breeding methods.

An aspect of the invention is a method of producing a plant of the invention comprising the steps of:
a. obtaining plant material, preferably seeds, of a plant of the invention;
b. treating said plant material with a mutagen to create mutagenized plant material, e.g. mutagenized seeds;
c. grow plants from the mutated seed or part of step b.

Said mutagenized plant material, e.g. the mutagenized seeds or progeny thereof obtained by selfing, may be analysed to identify a plants producing a modified amount, activity or function of AGL11-like protein. The method may further comprise analyzing the fruit flesh of the selected plant or progeny of the plant and selecting a plant of which the fruits have intense fruit phenotype. In this method, the plant material of step a) is preferably selected from the group consisting of seeds, pollen, plant cells, or plant tissue of a tomato or Cucurbiteae plant line or cultivar. Plant seeds being more preferred. In another aspect, the mutagen used in this method is ethyl methanesulfonate. In step b) and step c) the mutagenized plant material is preferably a mutant population, such as a TILLING population. Optionally the method may comprise a further step d. to determine the gene sequence encoding an AGL11-like protein or the promoter sequence of said gene. Said step d. may be followed by step e. of comparing the determined sequence obtained in step d. with a reference sequence such as for *Solanum lycopersicum* as represented by SEQ ID NO: 1, 2, 4, 5, 20, or parts thereof; for *Cucumis sativus* as represented by SEQ ID NO: 10, 11, 12, 13, or parts thereof; for *Cucumis melo* as represented by SEQ ID NO: 18, 19, 21, 22, or parts thereof. In another embodiment, such reference sequence can be selected from the group consisting of SEQ ID NO: 2, 5, 20, 10, 11, 12, 13 18, 19, 21, and 22; or parts thereof. In yet another embodiment, the method comprises a further step f) to determine if the fruits of the plant of step c) have an intense fruit phenotype (optional step f) may be included with or without steps d) or [d) and e)].

Thus, in one aspect a method for producing a plant comprising a modified amount, activity or function of AGL11-like protein is provided comprising the steps of:
a. providing a tomato TILLING population,
b. screening said TILLING population for mutants in the agl11-like gene, and
c. selecting from the mutant plants of b) those plants (or progeny of those plants) of which the fruits have intense fruit phenotype.

Mutant plants (M1) are preferably selfed one or more times to generate for example M2 populations or preferably M3 or M4 populations for phenotyping in step c). In M2 populations the mutant allele is present in a ratio of 1 (homozygous for mutant allele): 2 (heterozygous for mutant allele): 1 (homozygous for wild type allele).

In yet a further aspect the invention relates to a method for producing a hybrid plant, said method comprising: i) obtaining a first plant of the invention or from a seed from which a plant of the invention can be grown; and ii) crossing said first plant with a second plant to obtain hybrid seeds wherein said hybrid plant comprises a modified amount, activity or function of AGL11-like protein, wherein the plant is a member of plant family Cucurbitaceae or of species *Solanum lycopersicum*.

Plants and plant parts (e.g. fruits, cells, etc.) of the invention can be homozygous or heterozygous for the mutant allele.

Other putative AGL11-like genes/proteins can be identified in silica, e.g. by identifying nucleic acid or protein sequences in existing nucleic acid or protein database (e.g. GENBANK, SWISSPROT, TrEMBL) and using standard sequence analysis software, such as sequence similarity search tools (BLASTN, BLASTP, BLASTX, TBLAST, FASTA, etc.).

Seed Deposits

A representative sample of seeds of two tomato variety comprising a recombinant chromosome 6 were deposited by Nunhems B. V. on Sep. 10, 2013 at the NCIMB Ltd. (Ferguson Building, Craibstone Estate, Bucksburn Aberdeen, Scotland AB21 9YA, UK) according to the Budapest Treaty, under the Expert Solution (EPC 2000, Rule 32(1)). Seeds were given the following deposit numbers:

NCIMB 42161: *Solanum lycopersicum* with intense and ogc phenotype

NCIMB 42162: *Solanum lycopersicum* with intense and ogc phenotype and Ol-6 resistance.

The Applicant requests that samples of the biological material and any material derived therefrom be only released to a designated Expert in accordance with Rule 32(1) EPC or related legislation of countries or treaties having similar rules and regulation, until the mention of the grant of the patent, or for 20 years from the date of filing if the application is refused, withdrawn or deemed to be withdrawn.

Access to the deposit will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

EXAMPLES

Analysis of ogc Fruit Phenotype

The "ogc phenotype" or "ogc fruit phenotype" is the phenotype conferred by the presence of two recessive *Solanum lycopersicum* ogc alleles in the genome. Its presence was determined visually by analysing ripe tomato fruits by cutting the ripe tomato fruit into two halves and determining the tomato flesh colour; comparing the colour to a normal fruit type like e.g. Heinz or Moneymaker. Ogc phenotype has deep red flesh colour (red towards purple red) while a normal tomato has a less red flesh colour (red towards yellow-red). Pericarp of a normal tomato sometimes even has a white or green-white colour.

Fruit flesh was exposed for measurement by cutting the proximal end of the tomato transversely with a sharp knife, such that only the pericarp and the top of locular partitions were visible. The gelatinous placental tissue was not measured. Two measures were made on opposite sides of the exposed fleshy surface.

Analysis of Intense Fruit Phenotype

The intense fruit phenotype was determined visually in mature fruits by cutting these open. The seed cavities of the cross-section were compared to the seed cavities of the cross-section of normal fruits of control plants.

As standard reference commercial hybrid Nun 3155 was used (intense but not ogc).

Genetic Mapping of Causal Intense Mutation

Rough genetic mapping: Because degree of polymorphism in cultivar crosses is limiting, genetic mapping was executed in a *S. lycopersicum* (intense phenotype)×*S. pimpinellifolium* F2 population. Twelve intense phenotyped F2's were genotyped on the Illumina 6032 tomato SNP array (Illumina Custom Select Genotyping Array, as is known in the art) which resulted in a map interval of ~15 cM interval on tomato chromosome 6.

Fine mapping: Two thousand (2000) F2 individuals from the same cross were screened with "intense" flanking markers, based upon the Illumina rough genetic mapping. Recombinant F2 plants were phenotyped and recombinant plants for which the phenotype was not clear were propagated to F3 and subsequently F3 families were phenotyped. Additional SNPs were developed by "in silico SNP mining" in the intense genetic interval by comparing the Heinz 1706 reference genome sequence with a public Whole Genome re-Sequencing (WGre-S) of a *S. pimpinellifolium* accession. The intense interval was reduced to a 90 kbp physical interval.

Identification of a candidate causal by re-seqeunce the physical interval: The genomes of a homozygous intense line and the wild type cultivar Savantas were re-sequenced 15× Illumina hiseq sequencing (also WGre-S). The sequence reads were mapped against the Heinz 1706 public genome sequence and the 90 kb physical interval of the lines was mined for sequence variation. A 405 bp deletion in the Intense line was identified in the promoter of the TAGL11-like gene in tomato. As this gene is expressed in phase II of tomato fruit development, a mutation in this gene or its promoter makes sense in relation to the intense phenotype. The 405 bp deletion sequence is shown in SEQ ID NO: 2 which corresponds to nucleotides 1042 to nucleotide 637 upstream of the ATG start codon of SEQ ID NO: 1.

Genetic validation of the candidate causal mutation: A SCAR marker was developed on the 405 bp deletion of the TAGL11-like gene:

```
Forward primer:     TTGACTTCTGAAAGTGTTAGGC
Reverse primer:     ATTGCTATTTTCCGGCGAAC.
```

This SCAR marker showed full association with the intense phenotype on a panel consisting of about 200 different lines. In one aspect the invention relates to the use of this Forward or Reverse primer. In another aspect the invention relates to a method for identifying tomato plants with intense phenotype using this Forward or Reverse primer.

Orthologs in Melon and Cucumber

Input Data

Thirty-nine *Arabidopsis*, twenty-seven *Solanum lycopersicum*, twenty-two Petunia x hybrida, six *Antirrhinum majus*, and three *Nicotiana tabacum* MIKC-type MADS-box genes were downloaded from the public domain. The input sets were combined to one with a total of 97 sequences, consisting of complete gene sequences (intron and exons regions) and mRNA sequences (exons regions only). This dataset was used as input for the identification of TAGL11-like homologs in melon (*Cucumis melo*) and cucumber (*Cucumis sativus*). A pipeline was developed for that, which is explained in the next section.

Pipeline

A pipeline ('GenFamGenomeScan') was developed for the automation of several steps in this study. The pipeline consists of python scripts written for this project, in-house (Nunhems) developed scripts, and open source software, which is all executable on the command line of a Linux server. The scripting was done in a software development environment, Eclipse [Eclipse for PHP developers], and most of the python scripts interact with a MySQL database, designed in Microsoft Visio Professional 2007, and set up in Toad for MySQL [version 5.0]. WinSCP [Windows Secure CoPy] was used for the safe copying of files from the local computer to the external Linux server, and vice versa. The MySQL database allowed for storing and retrieving relevant data in a relational way. The database was designed so it was dynamic, and data redundancy was avoided as much as possible, while there is still the ability to retrieve all necessary information of a specific project. The database basically consisted of three tables. In one table information about the predicted gene models (potential homologs) was stored: name, genomic location, number of introns, and gene product. In the other two the information about the basic local alignment searches was stored (BLAST results) [S. F. Altschul et al (1990) *Journal of Molecular Biology* 215(3). 403-410].

First, the MIKC-type MADS-box input data from literature searches, was used to identify homologous sequences in the melon and cucumber genomes. The tblastx algorithm of the blastall program [Altschul et al, vide supra], which compares the sequences at amino acid level, was used. Another used parameter was a cut-off value for non-significant e-values greater than 0.1. The resulting BLAST results in XML format were parsed and written to a tab-delimited file by a Nunhems in-house developed python script called, 'blastXMLparse.py'.

For every input query sequence the best three hits were retrieved and a python script ('SearchAnnotations.py') checked if there was a FGENESH [A. A. Salamov A A, et al (2000). Genome Research 10(4): 516-522] predicted gene model in every hit region. FGENESH gene predictions are stored in a GFF3 file [Stein L (2013). Generic Feature Format Version 3. Retrieved from: http://gmod.org/wiki/GFF3], which was loaded into the Generic Genome Browser (GGB), an open-source web-based application to browse annotated genomic DNA [Stein L D et al (2002), The generic genome browser: a building block for a model organism system database. *Genome Research* 12(10):1599-1610].

The python program then stored all uniquely found genes together with the corresponding BLAST results in the MySQL database. FGENESH is a gene-prediction algorithm that makes use of Hidden Markov Models (HMM) and it is based on the recognition of sequence patterns of different types of exons, promoter sequences and polyadenylation signals. Basically, it uses a set of known sequences to predict new genes. For melon and cucumber, a training file for *Medicago truncatula* genomic DNA, was used.

Ab initio gene predictions, based on training data, are obviously not always 100% accurate. Another way of identifying protein-coding regions, introns, and even alternative splicing, is by using experimental sequence data. This gene validation step helped us to confirm a gene was predicted right (true positive), to notice possibly wrong predicted genes (false positive), or wrong gene structures. This gene validation step was performed manually in GGB [Stein et al, vide supra], by looking at mapped melon and cucumber unigenes, coming from ICUGI [International Cucurbit Genomics Initiative (at icugi.org/cgi-bin/ICuGI/index.cgi].

Conserved Motif and Functional Domain Analysis

Besides annotations on DNA level it was essential to make comparisons at protein level, and to find conserved motifs and functional domains. Predicted protein sequences by FGENESH were written to a fasta file with 'SearchAnnotations.py'.

For the identification of conserved motifs, we used the CLCBio Main Workbench (6.0). After importing the protein sequences into the workbench, an automated PFAM [Finn R D et al (2010). The Pfam Protein Families Database. *Nucleic Acids Research* 38:211-222] functional domain scan was done. This was a first step in identifying potential MADS-box proteins, which should contain a MADS-box and a K-box domain [Leseberg C H et all (2008). Interaction study of MADS-domain proteins in tomato. Journal of Experimental Botany 59(8):2253-2265; Hileman L C et all (2006). Molecular and Phylogenetic Analyses of the MADS-Box Gene Family in Tomato. Molecular Biology and Evolution 23 (11):2245-2258; Parenicova L et all (2003). Molecular and Phylogenetic Analyses of the Complete MADS-Box Transcription Factor Family in Arabidopsis: New Openings to the MADS World. The Plant Cell, 15:1538-1551].

Phylogenetics

Phylogenetic analyses were performed within CLC Bio Main Workbench as well. Multiple alignments were done with Clustal [Chenna R, Sugawara H, Koike T, Lopez R, Gibson T J, Higgins D G, Thompson J D (2003). Multiple Sequence Alignment with the Clustal series of programs. *Nucleic Acids Research* 31:3497-3500] using default parameters. Besides a whole protein alignment, an alignment of only the MADS-box domain was done, because this is a well conserved domain and it should give the true evolutionary distance between different MADS-box proteins. The phylogenetic trees were constructed using neighbor-joining (NJ) [Saitou N, Nei M (1987). The neighbor-joining method: a new method for reconstructing phylogenetic trees. *Molecular Biology and Evolution* 4(4):406-425] with bootstrap analysis (100 replicates).

Using this method, 4 (four) orthologs for the tomato AGL11-like protein in melon and cucumber were identified:

| Melon ortholog nr | ICUCI nr | Cucumber ortholog nr | ICUCI nr |
|---|---|---|---|
| M1 | Mu43977 | C1 | Cu100500 |
| M2 | Mu45645 | C2 | Cu105950 |
| M3 | Mu50731 | C3 | AAC08528 * |
| M4 | Mu48843 | C4 | Cu107465 |

* also referred to as Cu106150

The protein, cDNA and gene sequence of each of these is given in the sequence listing.

The sequence identity of these orthologs towards tomato AGL11-like (TAGL11-like) protein sequence and each other is given in the table below:

|  | TAGL11-like | C1 | C2 | C3 | C4 | M1 | M2 | M3 | M4 |
|---|---|---|---|---|---|---|---|---|---|
| TAGL11-like | 100% | 53% | 67% | 50% | 49% | 53% | 66% | 54% | 51% |
| C1 |  | 100% | 56% | 53% | 54% | 99.6% | 56% | 57% | 55% |
| C2 |  |  | 100% | 56% | 53% | 56% | 97% | 62% | 53% |
| C3 |  |  |  | 100% | 57% | 53% | 54% | 90% | 57% |
| C4 |  |  |  |  | 100% | 54% | 52% | 62% | 92% |
| M1 |  |  |  |  |  | 100% | 56% | 57% | 55% |
| M2 |  |  |  |  |  |  | 100% | 60% | 53% |
| M3 |  |  |  |  |  |  |  | 100% | 61% |
| M4 |  |  |  |  |  |  |  |  | 100% |

The sequence identity reveals that each ortholog in cucumber has a closely related ortholog in melon: C1-M1; C2-M2; C3-M3; C4-M4; with a sequence identity of more than 90% (e.g. more than 92%, more than 97% or even more than 99%). This was confirmed the phylogenetic tree data which showed only a small distance between each of the members of ortholog pairs C1-M1; C2-M2; C3-M3; and C4-M4.

The relative amount of mRNA of the four orthologs in cucumber (C1-C4) was determined using methods known in the art. The amount was determined in 5 samples: a mixed leaf sample, a mixed root sample, female flower, male flower and mixed fruit stages sample. All four orthologs had a positive relative mRNA level score in the mixed fruit stage sample, indicating that proteins of C1-C4 are being produced in the cucumber fruit. C4 being most active.

Population Development of *Solanum lycopersicum* Plants with Intense+ogc Phenotype Individuals of an inbred *L. esculentum* line (i.e. *Solarium lycopersicum* line) comprising two copies of the gene conferring the intense phenotypic trait (i.e. homozygous for intense), were crossed with a *L. esculentum* line carrying at homozygous level the gene ogc, conferring darker internal colour and lacking the mutant intense allele. Both parents were selected as carrying a similar fruit shape (round) and for the indeterminate plant habit which made it easier to select progenies suitable to be grown in greenhouse.

The F1 population was backcrossed into the recurrent parent (the line carrying intense). BC1 and BC2 were performed, ensuring the presence of ogc gene as well as the homozygosity of indeterminate habit (lack of sp mutant gene). One hundred and fifty (150) individuals of the population BC2F1 were sowed in a nursery and then transplanted into a breeding greenhouse. Plants were planted according to the local area growing conditions. Cycle was a typical spring cycle, with transplant at the end of winter and harvest in the first part of summer. Alternated spring growing season in Italy was alternated with one autumn season in Spain to have two full cycles/year. Fifteen (15) BC2F1 individuals were selected carrying both intense and ogc gene (scored by the use of molecular markers and selected by phenotyping).

The BC2F2 progenies were checked for intense fruit phenotype and for ogc presence, using molecular marker analysis and phenotype observation. Once the 2 genes were scored as fixed and homozygous, only phenotypic selection was performed, looking for the progenies more suitable to be used in future crossing blocks and as suitable source of the 2 genes for further populations.

Association of phenotype and confirmation with molecular marker analysis (Markers for ogc-phenotype are known in the art; Markers for intense-phenotype have been described above) showed that in the BC3F2 population individuals segregated in coupling for ogc and intense. One of these (ogc/ogc, i/i) was selected and submitted to NCIMB under number NCIMB 42161.

Population Development of *Solanum lycopersicum* Plants with Intense+ogc+Ol-6 Phenotype Individuals of an inbred *L. esculentum* line comprising two copies of the gene conferring the intense phenotypic trait and of the ogc gene (i.e. homozygous for intense+ogc), were crossed with a *L. esculentum* line (lacking the mutant intense allele) carrying at homozygous level the gene Ol-6, conferring resistance to Powdery Mildew *Oidium neolycopersici*. Both parents were selected as carrying indeterminate plant habit, making the final product more suitable to be grown in greenhouse.

The F1 population was grown and F2 population produced.

F2 population was screened through molecular markers to find out individuals carrying the combination of all the three genes. One hundred and twenty (120) individuals of the population F2 were tested in the nursery and 2 individuals were found to carry the recombination of intense+ogc+Ol-6 in homozygous form. One of these was selected and submitted under accession number NCIMB 42162.

---

The invention claimed is:

1. A cultivated *Solanum lycopersicum* plant comprising a reduced amount, activity or function of AGL11-like protein, or plant cell, tissue or plant part thereof, wherein the AGL11-like protein has at least 95% amino acid sequence identity to SEQ ID NO: 3, wherein said plant produces fruits having an intense phenotype and having an average fresh weight of at least about 120 g.

2. The plant according to claim 1, wherein the plant produces fruits having an average fresh weight of at least about 150 g, 200 g, 250 g, 300 g or even up to 600 g.

3. The plant according to claim 1, wherein the plant produces fruits having a round type.

4. The plant according to claim 1, wherein the plant has a mutation in the promotor sequence of the AGL11-like gene sequence.

5. The plant according to claim 4, wherein the plant has a deletion from nucleotide 1042 to nucleotide 637 upstream of the ATG start codon following SEQ ID NO: 1.

6. The plant according to claim 1, wherein the plant comprises the intense allele as found in seeds deposited under accession number NCIMB 42161 or NCIMB 42162.

7. The plant according to claim 1, wherein the reduced amount, activity or function of AGL11-like protein can be determined during fruit formation.

8. The plant according to claim 1, wherein the plant further comprises an allele conferring the ogc fruit phenotype.

9. The plant according to claim 8, wherein the plant comprises the ogc allele as found in seeds deposited under accession number NCIMB 42161 or NCIMB 42162.

10. The plant according to claim 1, wherein the plant further comprises an allele conferring an Oidium resistance phenotype.

11. The plant according to claim 8, wherein the plant comprises the Ol-6 allele as found in seeds deposited under accession number NCIMB 42162.

12. The plant according to claim 1, wherein said plant is an F1 hybrid.

13. Seed from which the plant according to claim 1 can be grown.

14. A plant cell, tissue or plant part of the plant according to claim 1, wherein the plant cell, tissue or plant part comprises a reduced amount, activity or function of AGL11-like protein, wherein the AGL11-like protein has at least 95% amino acid sequence identity to SEQ ID NO: 3.

15. A tomato fruit harvested from the plant according to claim 1.

16. The fruit according to claim 15, wherein said fruit is sliced.

17. A food or feed product comprising the fruit of claim 15.

* * * * *

SEQUENCE LISTING

<160> NUMBER OF SEQ ID NOS: 30

<210> SEQ ID NO 1
<211> LENGTH: 1950
<212> TYPE: DNA
<213> ORGANISM: Lycopersicon esculentum

<400> SEQUENCE: 1

```
tgttgaatga tggaatgaaa tacaaactta caaaattttt attattttct actttcagaa      60
atcattnttt ttattttta tttttacaag aaaagccatt ctttattgtt aaattatctt     120
ccttttttga aaaaaaagat attgaccaat ttaacattaa aattacagaa aaacacaatc     180
atgttgcgat aatagaattg cataattctg tcttaattaa gtataaatca gctgactgaa     240
ttctatgtgg aactcaacaa atcaaccta actttcattt caacgtgcgg tttcacaaaa     300
ccctaaaaaa gttaaatctt cactttatct atcaattgac actccataac ggatttagaa     360
ttttaattcc atgagttaag catttctaga tgtttagtat tgagtcaatt atatgtttga     420
agttataatt catgtaactt tgcctatgaa tttatgcttc atcagaagtt atgatttcaa     480
ttaaacttgt atccttccct atagatatga tatgaattta tatcatcgag ttaaattact     540
tcaagtttga cggaaatatt attcttaaat ttcaaacaag ttgatattga ttatatgaat     600
ttttaccatg aattcagaag tagaattaat atctatgttt ttcttaatta aacaaaatta     660
gagcccgttt gaataggttt agtagtcggt caaacctact tttaaatcaa ttttttgactt     720 ctgaaagtgt taggcaaata taaaaagtaa ctaaaataag ttacgaagtg tctgacaaag     780
taaaaaatga ctcaaaacaa ataaaaaatg atttaaaata agtcaaaaac caaagtagaa     840 tccctatta ctttttattt tttgacttaa aagtcatttc attttgattt tttatttta     900 atttaaaagc tatttttta agccaatcca gacggtctct taatatacag gtcaaacctc     960
attaaataaa atttaaatat ttgaaagaaa agtttgagag atttaaaca gcacaagggg    1020 catattagtc aagaagaaac aaaaataaca cgctttgcaa taattggtga aatttttagtc   1080 tgcaataaac aatcccataa catcacgtct ggtttatatc tggaaaaaag ccatttgaat   1140
gtcattttct tggccagcca tctctattat ctctcttcac tttaattttg agtgatactt    1200
tcttcgtcca tccgactcaa cacacatctt ttaagaaata ataaattcga agagtaattt    1260
tattatatat catcagtcac ccctattggt aacacgtcat ctaaatatta aaaagtaaat    1320
aaaatggtaa aacatctctt gtgttttca aattgaataa ttatttttag tatagtaaac    1380
aagtaaaaat agtcgtagct agggataaag ttagggtaag tagggatata atataaaaag   1440
aaagaaaagc atataagtat tatgttttt cttcattgat cagtgtacaa ataagaagtc    1500
tttggaagtt gtgtgagttt tcagaaagcc tttgaagttc gccggaaaat agcaatattt    1560
tcaattcaag ccaatcaggt ctattacgtt gatattttac atagcatcaa attttagaaa   1620
```

-continued

```
gaaaaaaata tatgaaaaaa cttaaatttc ccattcttcc atgcattttt taaatttttt    1680 ttttttttgca gattctgaaa tgtttctctc tgtgttcatt atgacaaaat taatttgtgt   1740
ttcgtgtgga actaagtcaa gctttagatc tatctgcaaa ttacataggt tatagaaata   1800
tgaaagattt cattttata tctatcaagc gcgtgcattt tttttttctt ttaatctttc    1860
acttatttga aagggaaggg tgcttactat ctgagtaacc tcctcttgtc acggaaattt   1920
tggttgatca ataaaagatc tccttgaaac                                    1950
```

<210> SEQ ID NO 2
<211> LENGTH: 405
<212> TYPE: DNA
<213> ORGANISM: Lycopersicon esculentum

<400> SEQUENCE: 2

```
gctattttt taagccaatc cagacggtct cttaatatac aggtcaaacc tcattaaata     60
aaatttaaat atttgaaaga aaagtttgag agattttaaa cagcacaagg ggcatattag   120
tcaagaagaa acaaaaataa cacgctttgc aataattggt gaaattttag tctgcaataa   180
acaatcccat aacatcacgt ctggtttata tctggaaaaa agccatttga atgtcatttt   240
cttggccagc catctctatt atctctcttc acttttaattt tgagtgatac tttcttcgtc   300
catccgactc aacacacatc ttttaagaaa taataaattc gaagagtaat tttattatat   360
atcatcagtc acccctattg gtaacacgtc atctaaatat taaaa                   405
```

<210> SEQ ID NO 3
<211> LENGTH: 237
<212> TYPE: PRT
<213> ORGANISM: Lycopersicon esculentum

<400> SEQUENCE: 3

```
Met Met Ile Leu Cys Met Gly Arg Gly Lys Ile Glu Ile Lys Arg Ile
1               5                   10                  15

Glu Asn Asn Thr Asn Arg Gln Val Thr Phe Cys Lys Arg Arg Asn Gly
            20                  25                  30

Leu Leu Lys Lys Ala Tyr Glu Leu Ser Val Leu Cys Glu Ala Glu Ile
        35                  40                  45

Ala Leu Ile Val Phe Ser Thr Arg Gly Arg Val Tyr Glu Tyr Ser Asn
    50                  55                  60

Asn Asn Ile Lys Ala Thr Ile Glu Arg Tyr Lys Lys Ala Thr Ala Glu
65                  70                  75                  80

Thr Ser Asn Ala Cys Thr Thr Gln Glu Leu Asn Ala Gln Phe Tyr Gln
                85                  90                  95

Gln Glu Ser Lys Lys Leu Arg Gln Gln Ile Gln Met Met Gln Asn Ser
            100                 105                 110

Asn Arg His Leu Val Gly Glu Gly Leu Ser Cys Leu Asn Val Arg Glu
        115                 120                 125

Leu Lys Gln Leu Glu Asn Arg Leu Glu Arg Gly Ile Ser Arg Ile Arg
    130                 135                 140

Ser Lys Lys His Glu Met Ile Leu Ala Glu Thr Glu Asn Leu Gln Lys
145                 150                 155                 160

Arg Glu Ile Leu Leu Glu Gln Glu Asn Ala Phe Leu Arg Ser Lys Ile
                165                 170                 175

Ala Glu Asn Glu Arg Leu Gln Glu Leu Ser Met Met Pro Ala Ala Gly
            180                 185                 190

Gly Gln Asp Tyr Ser Ala Ile Gln Gln Tyr Leu Ala Arg Asn Met Leu
```

```
              195                 200                 205
Gln Leu Asn Met Met Glu Gly Gln Gly Val Ser Ser Tyr Asp Pro Leu
            210                 215                 220

Pro Pro Pro His His Asp Lys Lys Ser Leu Glu Leu Gln
225                 230                 235
```

<210> SEQ ID NO 4
<211> LENGTH: 714
<212> TYPE: DNA
<213> ORGANISM: Lycopersicon esculentum

<400> SEQUENCE: 4

| | | | | | |
|---|---|---|---|---|---|
| atgatgatct | tgtgtatggg | aagaggaaag | atagagataa | agaggataga | gaacaacaca | 60 |
| aacaggcagg | ttacattttg | caagagaaga | aatggattgt | tgaagaaagc | ctatgaactc | 120 |
| tctgttctat | gtgaagctga | gattgctctt | attgttttct | ccacacgtgg | acgcgtctat | 180 |
| gaatactcta | caacaacat | taaggcaact | attgaacgat | acaagaaggc | aactgctgaa | 240 |
| acctctaatg | cttgcaccac | tcaagagctc | aatgctcagt | tttatcaaca | agaatcaaaa | 300 |
| aagctgcgcc | aacagataca | aatgatgcag | aattcaaaca | ggcatctggt | tggtgaagga | 360 |
| ttaagttgtt | tgaacgtaag | agagctgaag | cagttggaaa | atagacttga | acgaggcatc | 420 |
| agcagaatca | gatcaaaaaa | gcatgagatg | atactggctg | aaactgagaa | tttgcagaag | 480 |
| agggaaattc | tactggaaca | ggagaatgca | ttccttagat | caaagatagc | agaaaatgag | 540 |
| aggcttcagg | aactaagcat | gatgccagca | gcaggaggac | aagattacag | tgcaatacag | 600 |
| caatatttag | caagaaatat | gcttcaactt | aatatgatgg | aaggccaagg | agtctcttcc | 660 |
| tatgatccat | tgcctcctcc | tcatcatgac | aagaagtccc | ttgaacttca | gtag | 714 |

<210> SEQ ID NO 5
<211> LENGTH: 5919
<212> TYPE: DNA
<213> ORGANISM: Lycopersicon esculentum

<400> SEQUENCE: 5

| | | | | | |
|---|---|---|---|---|---|
| atgatgatct | tgtgtgtaag | ttatgtttac | acaagatttt | ttttaatttg | tgtgtatctt | 60 |
| ttcttgcata | tcatgaggag | aaaaaaaagg | aattggaaaa | acatttgtac | tactttttta | 120 |
| ttatatttgg | aggtagcttc | tcccaagaaa | ataaaaattt | aattcttcaa | atactaatta | 180 |
| atttggatga | ttatgtgagt | tattattgct | taaattcttg | tattggatgg | ttgtttttt | 240 |
| tttagtgata | gagagatttt | agaatcattt | ctcaaatctc | ttgttttaaa | tttcttcttt | 300 |
| gtttaatctc | tttgaatact | tagttctaca | catgcacgac | ttttaatatg | aggtgtttta | 360 |
| gagatacata | taacaatttt | accagtcgtt | tttaataata | ctactttttt | tttttaaaaa | 420 |
| aaaaaagaca | gtctaatttg | gagcaattct | ccaagaaaga | actagtttaa | aacattgatt | 480 |
| ttgtattata | aatttatttt | acttcatcat | caaacatgga | gttacttctg | cttcatcttt | 540 |
| cgtttatta | gttagaccta | actacctctt | caatttctac | tgaatggaag | aaaaaaaatg | 600 |
| atataagtta | ttgcttagat | tcttgtattg | aaagcgtttt | cataaattta | atcgaaactt | 660 |
| taaaattttt | tatagaagat | gaattgaaga | atcaattttt | ggatttcttt | ttggagtata | 720 |
| agcgaaattt | atccgaaaaa | ctgatttggg | caaattttg | gagttagatt | tttttttg | 780 |
| aagatggtaa | attttcaaga | aaagaaaaga | aaaaacaaa | tctcatgaag | aaacggtatt | 840 |
| ttaattttt | tagaaaaaat | ctatgatcga | accagagcta | attagttcat | agatttcttg | 900 |
| ttctagattt | ctactaattt | ttctcttgtt | atagaatgag | atatgtccga | tttattcatt | 960 |

```
actctcaaaa ttaaaacata ggtattaatt aattaaatat aaatgtgtta tattctcttt    1020
tatgtggtta atacagatgg gaagaggaaa gatagagata aagaggatag agaacaacac    1080
aaacaggcag gttacatttt gcaagagaag aaatggattg ttgaagaaag cctatgaact    1140
ctctgttcta tgtgaagctg agattgctct tattgttttc tccacacgtg gacgcgtcta    1200
tgaatactct aacaacaagt aatttcttat ttatctctca tatagttaaa tttgttcaat    1260
tagacgatca tatatatcgt tatataacat ataatatatg gacataatat ggcatttcat    1320
tagcatctac ttctttcttg atatcataat cattcgctta tctcttgatg tttgaaatct    1380
gaataatcat tttgttagtg cataaaataa ttgagctgta agaaagcata tatgaataca    1440
ctgttcctca aaatttatag tagttgtttg attcacacac aaatgacaga atcggaggtg    1500
gaggatactt acaatcaact cttctcgtct ttaattgtgt ttgagttata tgtaaaaaat    1560
attatcataa aaggatttac atataataat ctagataaat aatactatga aaggtttgag    1620
gatagataac ataatcaata tagaatgtta tttgtgaaac ttattgtcct tactttcact    1680
agaaaattag tctattttc  tcaattttaa gaaatttgtt ttttttttg  aaaaaaaat     1740 tattctaaaa ttttggctaa ccaaaatgga gaagataaaa aaaaaaagt  aaaatagaaa    1800 atattttccc ccatatcgaa aatatcctat atatccaaca ccgtacctaa gtcacaaaag    1860
atcaataaga aaagtgatct tgagcctaac tttatcttcg aaggtttgct tatgaggtaa    1920
aaattataat aagaaaagtg atttgaggca taattaactc tacttcaaaa cttagttcat    1980
gaggtaaaaa ctatccaaaa tcatatagga agacacatcg gtcattaacc atcaatatga    2040
gatactaata ttttcgtac  aattagtcct gtcaactaaa gcgtgaacaa tataatataa    2100
agatccaacg tcaaaataag ttaagaaatg agatgaatat aaatttacta tctcttaatc    2160
acaattaaaa aaggaaggc  attctcaggt gatatcgaat aatagtacac tagtgtttta    2220
ggagatgttc acacatatag tttaacttag ttgaatctct acccaatcct cgagccctct    2280
gtcgaagctt agttaataat tcaatctcaa ttgctagttc atgagaatga gatctgccaa    2340
aagttaaacc atcttagaag attaataatt gccactttgt tttgaatttt gaataacaca    2400
aatttttctt ttaaaaaaaa aaaaatatta ataaaaaaaa tttgccacat ccatcaccag    2460
cctgtgaaat aattaaagtg aaatgaaata tcctctcgcg ataaactttt acatgagatg    2520
atttatactt caatataatt atagtataat agtaccaaag ctataggtat aagtcttgag    2580
tttgaatcgt acagtaacta actcatcatc atcaattaaa aacgaatttt tcacgtgctt    2640
ggccgtacat attctctctc taacttcttt aaattcttaa ataagatggt ttatgcactt    2700
caaacaacta tgataattac cttgaaagat ccatgtgtga gtatatatat atatatatat    2760
gcaagaaaag tgaatgagtg acaaataata tttattggtt ttatacatga aaagtgtca    2820 aggacactcc agattaataa gtactaaaag aagtatatat tgagaagtcc catcatgagt    2880
gacttgtgac tattgtgttc tgctgttatg agggcctttt tgtttcctct tgtagcttat    2940
gcattataaa gttctcctgc tttggtttgt atctattcta gttctagtca atatatgttc    3000
tctctttcac ttttatgtct acatatatta attaattaaa aaagtacttc tcccatatat    3060
aaggtctccc tattgcatgc atatggaata ttaaaaaaaa ataaaaaaag tacatattat    3120
tatcacccta aaatgtaaaa aagatatgat tccaaagata gtgcaacata aaaggagaga    3180
agagaaatct tcaaaaatta catcatcaca aattagattt tcttatcaat gttttttttt    3240
ttaatctgca ctctgatgag taaatcattc tcttgctttt agttgtttcc attgctagct    3300
```

```
tttggtttca ttgaacatga tcttttatg caacacaaag tactacctat ctttgtacta      3360
atttatattg cattgtttga atttcaaaag agtcagttta aatagtaaga ccgaatacaa      3420
acatataaaa agtgttttat aataaaattt acatatttaa aaattagata aaaaatatga      3480
taagtcgtaa taattaactt tgtggataga atggctcat taaaggttta atgcaatggc       3540 ttgtttttaat tgaccacctg aaaatatata ttataaaaaa atattcttat tagacacttc     3600
ccgtttaaat ttagaaaatg acttttgggc atgtgtgttc tcaagtacct tgactactta     3660
aaatatgtat caccttattt ttaattatat acattagcct cgaatattta ttgtttataa     3720
agtatatgat aaaactttttg gtatacacag cattaaggca actattgaac gatcaagaa     3780 ggcaactgct gaaacctcta atgcttgcac cactcaagag ctcaatgctc aggtaattag     3840
ttaagcaaaa tcatttaact ttttgatgct aaacaataaa aattcatcat taattctatt    3900
tcgggatgga ttataaaaaa aaaacaaatt attagctata tgacaaaata ttgttttggc     3960
tgtcatgtat gtagttttat caacaagaat caaaaaagct gcgccaacag atacaaatga    4020
tgcagaattc aaacaggtaa caccataatt aattcaataa attaaatttg ggatgaattt     4080
taaaactaat tcgattatat gcacaaaata ttttatatat tccacgtgta ggcatctggt     4140
tggtgaagga ttaagttgtt tgaacgtaag agagctgaag cagttggaaa atagacttga     4200
acgaggcatc agcagaatca gatcaaaaaa ggtatatttg taatggttgg attactaaaa     4260
tattgttgta agtgcatact attgcattgt ttggagttgt aaaccaaaca cattttttcct   4320 tagaagttac tcgcgcttttg aaattacgcg ttatgataaa attatttcat aaaaatatga   4380
ctcggaaagt ttgtttcaag ccatttggat ctgctcacat atagtacaag gccctaaatg     4440
agtaatagga aaccttgcac ttttttttttt gataagtgtc atatagagaa aggaaacaaa    4500
aactttgata ttattttttgt ttggtaatta atgaattat aagaaaacaa atgaattaat     4560
tgaaacttga taagagttag acaacattga ttatgatcca ttttttagtc catcgtgatc    4620
caacttgtga cagataatcg atatacgatc cgttcattta ttaacttaac tcactttaat    4680
tttgatctgt ccatctgaca acattacatg tagtgaaaat gtcagcctaa gtagcaaaat    4740 ttttatgtt gattatacaa atcctcataa cagtagcttt gatgtttgtt atgtggttga    4800
acagcatgag atgatactgg ctgaaactga gaatttgcag aagagggtaa taattttattg   4860 aaaaattgtt tttatccttt ttatgttttta ggttcagact aaatataatt atgctttggc   4920
atattttata atctttcaac ttgctgtttt aataggaaat tctactggaa caggagaatg    4980
cattccttag atcaaaggta cttaattagt agcacacatt tctttttaaat tggttactta   5040 gaaaagaat acattttaat atttatagat agacattaac atcgataatc acttaatctt     5100
gttagtatat ttttttagac ccttgaacta tggtctattc cacttaagca acggaacacg    5160
ataaagtgtt cctaattata agaaacttct ggtttaactt tttgacagat gtttgcgcgt    5220
gttcttaatt atatattagg tattaactaa tcacaaaata tgtcatttca ttttaattat    5280
tcacatcgac ctcaattaaa acatgcatgc ttaagacttt gttacttatt gaggctaatg    5340
catgtaatct aagcaagcga tgacactttt taagcgatca ccttctccat gtaattgact    5400
cttagaatat tccgaaaagt tattaaagtg ccaaatagaa acactttatc atatgtttag    5460
gcgctcaatt agaataaaac aagcaaaagt tgtttaaat gaaactgacg tacactttaa    5520
tccccaaaaa ttgcaaattt tcatttagtt actttattat tagtacttta ttttttaaaag  5580 agaatccggg aggggattat aaggtggaaa acaaaactct taccaataag gtgagagtta    5640
agataacgaa ccatctggct agctacgtac taagattccc attttagttat tttctctcat   5700
```

```
ggagattaat gaaaatatta ttgctttcag atagcagaaa atgagaggct tcaggaacta    5760
agcatgatgc cagcagcagg aggacaagat tacagtgcaa tacagcaata tttagcaaga    5820
aatatgcttc aacttaatat gatggaaggc caaggagtct cttcctatga tccattgcct    5880
cctcctcatc atgacaagaa gtcccttgaa cttcagtag                           5919
```

<210> SEQ ID NO 6
<211> LENGTH: 236
<212> TYPE: PRT
<213> ORGANISM: Cucumis sativus

<400> SEQUENCE: 6

```
Met Gly Arg Gly Lys Ile Glu Ile Lys Arg Ile Glu Asn Thr Thr Asn
1               5                   10                  15

Arg Gln Val Thr Phe Cys Lys Arg Arg Asn Gly Leu Leu Lys Lys Ala
            20                  25                  30

Tyr Glu Leu Ser Val Leu Cys Asp Ala Glu Val Ala Leu Ile Val Phe
        35                  40                  45

Ser Thr Arg Gly Arg Leu Tyr Glu Tyr Ala Asn Asn Ser Val Arg Gly
    50                  55                  60

Thr Ile Glu Arg Tyr Lys Lys Ala Phe Ala Asp Ser Ser Asn Ser Gly
65                  70                  75                  80

Leu Ser Val Ala Glu Ala Asn Val Gln Phe Tyr Gln Gln Glu Ala Thr
                85                  90                  95

Lys Leu Lys Arg Gln Ile Arg Glu Ile Gln Asn Ser Asn Arg His Ile
            100                 105                 110

Leu Gly Glu Ala Leu Ser Ser Leu Pro Leu Lys Glu Leu Lys Ser Leu
        115                 120                 125

Glu Gly Arg Leu Glu Arg Gly Ile Ser Lys Val Arg Ala Lys Lys Asn
    130                 135                 140

Glu Thr Leu Phe Ala Glu Met Glu Phe Met Gln Lys Arg Glu Met Glu
145                 150                 155                 160

Leu Gln Ser His Asn Asn Tyr Leu Arg Ala Gln Ile Ala Glu His Glu
                165                 170                 175

Arg Ile Gln Gln Gln Gln Gln Gln Gln Thr Asn Met Met Gln
            180                 185                 190

Arg Ala Thr Tyr Glu Ser Val Gly Gly Gln Tyr Asp Asp Glu Asn Arg
        195                 200                 205

Ser Thr Tyr Gly Ala Val Gly Ala Leu Met Asp Ser Asp Ser His Tyr
    210                 215                 220

Ala Pro Gln Asp His Leu Thr Ala Leu Gln Leu Val
225                 230                 235
```

<210> SEQ ID NO 7
<211> LENGTH: 225
<212> TYPE: PRT
<213> ORGANISM: Cucumis sativus

<400> SEQUENCE: 7

```
Met Gly Arg Gly Lys Ile Glu Ile Lys Arg Ile Glu Asn Thr Thr Asn
1               5                   10                  15

Arg Gln Val Thr Phe Cys Lys Arg Arg Asn Gly Leu Leu Lys Lys Ala
            20                  25                  30

Tyr Glu Leu Ser Val Leu Cys Asp Ala Glu Val Ala Leu Ile Val Phe
        35                  40                  45
```

```
Ser Ser Arg Gly Arg Leu Tyr Glu Tyr Ser Asn Asn Ser Ile Lys Thr
    50                  55                  60
Thr Ile Glu Arg Tyr Lys Lys Ala Cys Ser Asp Ser Ser Ala Thr Ser
 65                  70                  75                  80
Ser Val Thr Glu Leu Asn Thr Gln Tyr Tyr Gln Gln Glu Ser Ala Lys
                85                  90                  95
Leu Arg Gln Gln Ile Gln Met Leu Gln Asn Ser Asn Arg His Leu Met
            100                 105                 110
Gly Asp Ser Leu Ser Ala Leu Thr Val Lys Glu Leu Lys Gln Leu Glu
            115                 120                 125
Asn Arg Leu Glu Arg Gly Ile Thr Arg Ile Arg Ser Lys Lys His Glu
    130                 135                 140
Met Leu Leu Ala Glu Ile Glu Tyr Leu Gln Lys Arg Glu Ile Glu Leu
145                 150                 155                 160
Glu Asn Glu Asn Val Cys Ile Arg Thr Lys Ile Ala Glu Val Glu Arg
                165                 170                 175
Val Gln Gln Ala Asn Met Val Ser Gly Gln Glu Leu Asn Ala Ile Gln
            180                 185                 190
Ala Leu Ala Asn Ser Arg Asn Phe Phe Ser Pro Asn Ile Met Glu Pro
    195                 200                 205
Ala Gly Pro Val Ser Tyr Ser His Gln Asp Lys Lys Met Leu His Leu
210                 215                 220
Gly
225

<210> SEQ ID NO 8
<211> LENGTH: 262
<212> TYPE: PRT
<213> ORGANISM: Cucumis sativus

<400> SEQUENCE: 8

Met Ser Lys His Tyr Gln Ser Pro Leu Thr Arg Met Ile Lys Glu Glu
  1               5                  10                  15
Gly Lys Gly Lys Leu Gln Ile Lys Gly Met Phe Gln Asn Gln Glu Glu
                20                  25                  30
Lys Met Ser Asp Ser Pro Gln Arg Lys Met Gly Arg Gly Lys Ile Glu
            35                  40                  45
Ile Lys Arg Ile Glu Asn Thr Thr Asn Arg Gln Val Thr Phe Cys Lys
    50                  55                  60
Arg Arg Asn Gly Leu Leu Lys Lys Ala Tyr Glu Leu Ser Val Leu Cys
 65                  70                  75                  80
Asp Ala Glu Val Ala Leu Ile Val Phe Ser Ser Arg Gly Arg Leu Tyr
                85                  90                  95
Glu Tyr Ala Asn Asn Ser Val Lys Ala Thr Ile Asp Arg Tyr Lys Lys
            100                 105                 110
Ala Ser Ser Asp Ser Ser Asn Thr Gly Ser Thr Ser Glu Ala Asn Thr
            115                 120                 125
Gln Phe Tyr Gln Gln Glu Ala Ala Lys Leu Arg Val Gln Ile Gly Asn
    130                 135                 140
Leu Gln Asn Ser Asn Arg Asn Met Leu Gly Glu Ser Leu Ser Ser Leu
145                 150                 155                 160
Thr Ala Lys Asp Leu Lys Gly Leu Glu Thr Lys Leu Glu Lys Gly Ile
                165                 170                 175
Ser Arg Ile Arg Ser Lys Lys Asn Glu Leu Leu Phe Ala Glu Ile Glu
            180                 185                 190
```

Tyr Met Arg Lys Arg Glu Ile Asp Leu His Asn Asn Asn Gln Met Leu
            195                 200                 205

Arg Ala Lys Ile Ala Glu Ser Glu Arg Asn Val Asn Met Met Gly Gly
    210                 215                 220

Glu Phe Glu Leu Met Gln Ser His Pro Tyr Asp Pro Arg Asp Phe Phe
225                 230                 235                 240

Gln Val Asn Gly Leu Gln His Asn His Gln Tyr Pro Arg Gln Asp Asn
            245                 250                 255

Met Ala Leu Gln Leu Val
            260

<210> SEQ ID NO 9
<211> LENGTH: 262
<212> TYPE: PRT
<213> ORGANISM: Cucumis sativus

<400> SEQUENCE: 9

Met Phe Cys Arg Lys Arg Lys Lys Met Ser Cys Tyr Glu Glu Glu Asp
1               5                   10                  15

Glu Glu Ser Gly Val Val Gly Leu Arg Arg Ser Ser Ser Ser Ser Arg
            20                  25                  30

Thr Gly Arg Gly Lys Ile Glu Ile Lys Arg Ile Glu Asn Thr Thr Asn
        35                  40                  45

Arg Gln Val Thr Phe Cys Lys Arg Arg Asn Gly Leu Leu Lys Lys Ala
    50                  55                  60

Tyr Glu Leu Ser Val Leu Cys Asp Ala Glu Val Ala Leu Ile Val Phe
65                  70                  75                  80

Ser Ser Arg Gly Arg Leu Tyr Glu Tyr Ala Asn Asn Ser Val Arg Ala
                85                  90                  95

Thr Ile Ser Arg Tyr Lys Lys Ala Tyr Ser Asp Pro Ser Thr Ala Met
            100                 105                 110

Thr Val Ser Glu Ala Asn Thr Gln Phe Tyr Gln Gln Glu Ser Ala Lys
        115                 120                 125

Leu Arg Ala Gln Ile Gly Asn Leu Gln Asn Leu Asn Arg His Leu Leu
    130                 135                 140

Gly Glu Ser Ile Ser Ser Leu Ser Val Lys Asp Leu Lys Ser Leu Glu
145                 150                 155                 160

Val Lys Leu Glu Lys Gly Ile Ser Arg Ile Arg Ser Arg Lys Asn Glu
                165                 170                 175

Leu Leu Phe Ser Glu Ile Glu Tyr Met Gln Lys Arg Glu Ile Glu Leu
            180                 185                 190

His Thr Asn Asn Gln Leu Ile Arg Ala Lys Ile Ala Glu Thr Glu Arg
        195                 200                 205

Ser Gln Gln Asn Thr Asn Ala Ser Asn Asn Gly Ile Ala Thr Arg
    210                 215                 220

Arg Gly Glu Glu Gly Ser Met Gly Thr Asn Leu Glu Asp Asn Asn His
225                 230                 235                 240

His Gln Tyr Asp Ser Thr Asn Tyr Phe Asp Pro His Asn His Pro
                245                 250                 255

Ile Ser Leu Gln Leu Val
            260

<210> SEQ ID NO 10
<211> LENGTH: 711
<212> TYPE: DNA

<213> ORGANISM: Cucumis sativus

<400> SEQUENCE: 10

| | | | | | |
|---|---|---|---|---|---|
| atgggaagag | gtaagattga | aataaaaaga | attgaaaata | ctacaaatcg | tcaagtcacc | 60 |
| ttttgcaaga | gaagaaatgg | attgcttaaa | aaagcttatg | agctgtctgt | tctttgtgat | 120 |
| gctgaagttg | ctctcatcgt | cttctctact | cgtggtcgtc | tctacgaata | cgcaaataat | 180 |
| agtgttagag | gaacgattga | gaggtacaag | aaagcatttg | ctgattcttc | caattccgga | 240 |
| ttatcagttg | ccgaagctaa | tgtacagttt | taccaacaag | aagccaccaa | gttgaagaga | 300 |
| cagattaggg | aaattcagaa | ctcaaacagg | catatcctgg | gagaagcact | cagctcattg | 360 |
| ccattaaaag | agctcaaaag | tcttgagggc | agattggaga | gaggtatcag | caaagttagg | 420 |
| gctaaaaaga | acgaaacctt | gtttgcagaa | atggaattca | tgcaaaaaag | ggaaatggaa | 480 |
| cttcagagcc | acaataacta | tctgagagca | cagattgcag | aacacgaaag | aatacaacag | 540 |
| cagcagcagc | aacaacagca | aacgaacatg | atgcaaaggg | caacatatga | gagtgtggga | 600 |
| gggcaatatg | atgatgagaa | tagaagtact | tatggggctg | taggggcgct | tatggattca | 660 |
| gacagccatt | atgctcctca | agaccatctc | actgcccttc | agcttgttta | a | 711 |

<210> SEQ ID NO 11
<211> LENGTH: 678
<212> TYPE: DNA
<213> ORGANISM: Cucumis sativus

<400> SEQUENCE: 11

| | | | | | |
|---|---|---|---|---|---|
| atggggagag | gaaagataga | gataaagaga | atagagaaca | caacaaatag | acaagttaca | 60 |
| ttctgtaaga | gaagaaatgg | acttttgaaa | aaagcttatg | aactctctgt | tctttgtgat | 120 |
| gctgaagttg | ctctcattgt | cttctccagc | cgtggccgtc | tctatgaata | ctccaataac | 180 |
| agcatcaaaa | caactattga | gaggtacaag | aaggcttgtt | ctgatagctc | agctactagc | 240 |
| tctgtcactg | aactaaatac | tcaatattat | cagcaagaat | cggctaaact | gcgtcaacag | 300 |
| atacaaatgc | ttcagaattc | caacaggcac | ttgatggggg | actccttgag | tgctcttact | 360 |
| gtcaaagaac | tcaagcagct | tgaaaatagg | cttgaaagag | gcatcactag | aatcagatca | 420 |
| aagaagcacg | aaatgttgct | agcagaaatt | gagtaccttc | agaaaaggga | gattgagctg | 480 |
| gagaacgaaa | atgtgtgtat | tagaaccaag | atagcagaag | tagagagggt | tcaacaagca | 540 |
| aacatggtat | ctggacaaga | actgaatgca | atacaagcat | tggctaactc | tcgcaatttc | 600 |
| ttctctccca | atatcatgga | acctgctgga | cctgtttctt | actctcatca | agacaagaaa | 660 |
| atgcttcatc | ttgggtga | | | | | 678 |

<210> SEQ ID NO 12
<211> LENGTH: 789
<212> TYPE: DNA
<213> ORGANISM: Cucumis sativus

<400> SEQUENCE: 12

| | | | | | |
|---|---|---|---|---|---|
| atgtccaagc | attatcagtc | accactcaca | agaatgatta | ggaagaagg | aaagggtaag | 60 |
| ttgcaaataa | aggggatgtt | ccagaatcaa | gaagagaaga | tgtcagactc | gcctcagagg | 120 |
| aagatgggaa | gaggaaagat | tgagattaag | aggattgaaa | atacaacaaa | tcgtcaagtc | 180 |
| actttctgta | agaagaagaa | atgggttgct | taaaaaagctt | atgaactttc | tgttctttgt | 240 |
| gatgctgaag | ttgctctcat | cgtttttctca | agccgtggcc | gcctctatga | atatgctaac | 300 |
| aacagtgtga | aggcaacaat | tgatagatat | aagaaagcat | cctcagattc | ctccaacact | 360 |

```
ggatctactt ctgaagctaa cactcagttt tatcaacaag aagctgccaa actccgagtt    420
cagattggta acttacagaa ctcaaacagg aacatgctag gcgagtctct aagttctctg    480
actgcaaaag atctgaaagg cctggagacc aaacttgaga aggaattag tagaattagg    540 tccaaaaaga atgaactcct gtttgctgag attgagtata tgcgaaaaag ggaaattgat    600
ttgcacaaca acaatcagat gcttcgggca agatagctg agagtgaaag aaatgtgaac    660
atgatgggag gagaatttga gctgatgcaa tctcatccgt acgatccaag agacttcttc    720
caagtgaacg gcttacagca taatcatcaa tatccacgcc aagacaacat ggctcttcaa    780
ttagtataa                                                          789

<210> SEQ ID NO 13
<211> LENGTH: 789
<212> TYPE: DNA
<213> ORGANISM: Cucumis sativus

<400> SEQUENCE: 13
atgttttgca ggaaaagaaa aaaatgagt tgttatgagg aagaagatga agaatcagga     60
gtagtaggat taagaagatc atcatcatca tcaagaacag gaagaggaaa gattgaaata    120
aagagaattg aaaatacaac aaatcgtcaa gttactttct gtaaacgaag aaatggtttg    180
cttaagaaag cttatgaact ctctgtcctt tgtgatgctg aggttgctct tatcgtcttc    240
tcctcccgtg gtcgtctcta tgaatacgct aacaacagtg ttagggctac gatttcgagg    300
tacaaaaagg catattcgga tccctccacc gccatgaccg tttcagaagc caatactcag    360
ttctaccagc aagaatctgc caaattacga gctcaaatcg gaaatttgca aaacctaaac    420
aggcatttgt tgggggaatc catcagttcg ttatcagtta aagatttgaa agcctagag    480 gtgaaattgg agaaaggaat tagccgaatt cgatccagaa agaatgagct tctgttttcg    540
gagattgaat acatgcaaaa aagggaaatt gaactgcaca ctaacaacca gctgatacgt    600
gcaaagatag ccgagacaga gagaagccaa caaaacacaa atgcaagtaa taacaatgga    660
atagcaacaa gaagaggaga ggaaggatca atgggtacaa atttagagga caacaatcat    720
catcaatatg actcaacaaa ctactttgat ccccatcata atcaccctat ctctcttcaa    780
cttgtgtaa                                                          789

<210> SEQ ID NO 14
<211> LENGTH: 236
<212> TYPE: PRT
<213> ORGANISM: Cucumis melo

<400> SEQUENCE: 14

Met Gly Arg Gly Lys Ile Glu Ile Lys Arg Ile Glu Asn Thr Thr Asn
1               5                   10                  15

Arg Gln Val Thr Phe Cys Lys Arg Arg Asn Gly Leu Leu Lys Lys Ala
            20                  25                  30

Tyr Glu Leu Ser Val Leu Cys Asp Ala Glu Val Ala Leu Ile Val Phe
        35                  40                  45

Ser Thr Arg Gly Arg Leu Tyr Glu Tyr Ala Asn Asn Ser Val Arg Gly
    50                  55                  60

Thr Ile Glu Arg Tyr Lys Lys Ala Phe Ala Asp Ser Ser Asn Ser Gly
65                  70                  75                  80

Leu Ser Val Ala Glu Ala Asn Val Gln Phe Tyr Gln Gln Glu Ala Thr
                85                  90                  95
```

```
Lys Leu Lys Arg Gln Ile Arg Glu Ile Gln Asn Ser Asn Arg His Ile
                100                 105                 110

Leu Gly Glu Ala Leu Ser Ser Leu Pro Leu Lys Glu Leu Lys Ser Leu
            115                 120                 125

Glu Gly Arg Leu Glu Arg Gly Ile Ser Lys Val Arg Ala Lys Lys Asn
        130                 135                 140

Glu Thr Leu Phe Ala Glu Met Glu Phe Met Gln Lys Arg Glu Val Glu
145                 150                 155                 160

Leu Gln Ser His Asn Asn Tyr Leu Arg Ala Gln Ile Ala Glu His Glu
                165                 170                 175

Arg Ile Gln Gln Gln Gln Gln Gln Gln Gln Thr Asn Met Met Gln
            180                 185                 190

Arg Ala Thr Tyr Glu Ser Val Gly Gly Gln Tyr Asp Asp Glu Asn Arg
        195                 200                 205

Ser Thr Tyr Gly Ala Val Gly Ala Leu Met Asp Ser Asp Ser His Tyr
210                 215                 220

Ala Pro Gln Asp His Leu Thr Ala Leu Gln Leu Val
225                 230                 235

<210> SEQ ID NO 15
<211> LENGTH: 230
<212> TYPE: PRT
<213> ORGANISM: Cucumis melo

<400> SEQUENCE: 15

Met Gly Arg Gly Lys Ile Glu Ile Lys Arg Ile Glu Asn Thr Thr Asn
1               5                   10                  15

Arg Gln Val Thr Phe Cys Lys Arg Arg Asn Gly Leu Leu Lys Lys Ala
            20                  25                  30

Tyr Glu Leu Ser Val Leu Cys Asp Ala Glu Val Ala Leu Ile Val Phe
        35                  40                  45

Ser Ser Arg Gly Arg Leu Tyr Glu Tyr Ser Asn Asn Ser Ile Lys Thr
    50                  55                  60

Thr Ile Glu Arg Tyr Lys Lys Ala Cys Ser Asp Ser Ser Ala Thr Ser
65                  70                  75                  80

Ser Val Thr Glu Leu Asn Thr Gln Tyr Tyr Gln Gln Glu Ser Ala Lys
                85                  90                  95

Leu Arg Gln Gln Ile Gln Met Leu Gln Asn Ser Asn Ser Asn Leu Val
            100                 105                 110

Arg His Leu Met Gly Asp Ser Leu Ser Ala Leu Thr Val Lys Glu Leu
        115                 120                 125

Lys Gln Leu Glu Asn Arg Leu Glu Arg Gly Ile Thr Arg Ile Arg Ser
    130                 135                 140

Lys Lys His Glu Met Leu Leu Ala Glu Ile Glu Tyr Leu Gln Lys Arg
145                 150                 155                 160

Glu Ile Glu Leu Glu Asn Glu Asn Val Cys Ile Arg Thr Lys Ile Ala
                165                 170                 175

Glu Val Glu Arg Val Gln Gln Ala Asn Met Ala Val Ser Gly Gln Glu
            180                 185                 190

Leu Asn Ala Ile Gln Ala Leu Ala Asn Ser Arg Asn Phe Phe Ser Pro
        195                 200                 205

Asn Ile Met Glu Thr Ala Gly Pro Val Ser Phe Ser His Gln Asp Lys
    210                 215                 220

Lys Met Leu His Leu Gly
225                 230
```

<210> SEQ ID NO 16
<211> LENGTH: 237
<212> TYPE: PRT
<213> ORGANISM: Cucumis melo

<400> SEQUENCE: 16

Met Phe Gln Asn Gln Glu Lys Met Ser Asp Ser Pro Gln Arg Lys
1               5                   10                  15

Met Gly Arg Gly Lys Ile Glu Ile Lys Arg Ile Glu Asn Thr Thr Asn
            20                  25                  30

Arg Gln Val Thr Phe Cys Lys Arg Asn Gly Leu Leu Lys Lys Ala
            35                  40                  45

Tyr Glu Leu Ser Val Leu Cys Asp Ala Glu Val Ala Leu Ile Val Phe
50                  55                  60

Ser Ser Arg Gly Arg Leu Tyr Glu Tyr Ala Asn Asn Ser Val Lys Ala
65                  70                  75                  80

Thr Ile Asp Arg Tyr Lys Lys Ala Ser Ser Asp Ser Ser Asn Thr Gly
                85                  90                  95

Ser Thr Ser Glu Ala Asn Thr Gln Phe Tyr Gln Gln Glu Ala Ala Lys
            100                 105                 110

Leu Arg Val Gln Ile Gly Asn Leu Gln Asn Ser Asn Arg Asn Met Leu
            115                 120                 125

Gly Glu Ser Leu Ser Ser Leu Thr Ala Lys Asp Leu Lys Gly Leu Glu
130                 135                 140

Thr Lys Leu Glu Lys Gly Ile Ser Arg Ile Arg Ser Lys Lys Asn Glu
145                 150                 155                 160

Leu Leu Phe Ala Glu Ile Glu Tyr Met Arg Arg Arg Glu Ile Asp Leu
                165                 170                 175

His Asn Asn Asn Gln Met Leu Arg Ala Lys Ile Ala Glu Ser Glu Arg
            180                 185                 190

Asn Val Asn Met Met Gly Gly Glu Phe Glu Leu Met Gln Ser His Pro
            195                 200                 205

Tyr Asp Pro Arg Asp Phe Phe Gln Val Asn Gly Leu Gln His Asn His
210                 215                 220

Gln Tyr Pro Arg Gln Asp Asn Met Ala Leu Gln Leu Val
225                 230                 235

<210> SEQ ID NO 17
<211> LENGTH: 256
<212> TYPE: PRT
<213> ORGANISM: Cucumis melo

<400> SEQUENCE: 17

Met Ser Cys Tyr Glu Glu Glu Asp Glu Glu Ser Gly Val Val Gly Leu
1               5                   10                  15

Arg Lys Ser Ser Ser Ser Ser Arg Thr Gly Arg Gly Lys Ile Glu Ile
            20                  25                  30

Lys Arg Ile Glu Asn Thr Thr Asn Arg Gln Val Thr Phe Cys Lys Arg
            35                  40                  45

Arg Asn Gly Leu Leu Lys Lys Ala Tyr Glu Leu Ser Val Leu Cys Asp
            50                  55                  60

Ala Glu Val Ala Leu Ile Val Phe Ser Ser Arg Gly Arg Leu Tyr Glu
65                  70                  75                  80

Tyr Ala Asn Asn Ser Val Arg Ala Thr Ile Ser Arg Tyr Lys Lys Ala
                85                  90                  95

```
Tyr Ser Asp Pro Ser Thr Ala Met Ser Val Ser Glu Ala Asn Thr Gln
            100                 105                 110

Phe Tyr Gln Gln Glu Ser Ala Lys Leu Arg Ala Gln Ile Gly Asn Leu
        115                 120                 125

Arg Asn Leu Asn Arg His Leu Leu Gly Glu Ser Ile Ser Ser Leu Ser
    130                 135                 140

Val Lys Asp Leu Lys Ser Leu Glu Val Lys Leu Glu Lys Gly Leu Ser
145                 150                 155                 160

Arg Ile Arg Ser Arg Lys Asn Glu Leu Leu Phe Ser Glu Ile Glu Tyr
                165                 170                 175

Met Gln Lys Arg Glu Ile Glu Leu His Thr Asn Asn Gln Leu Ile Arg
            180                 185                 190

Ala Lys Ile Ala Glu Thr Glu Arg Ser Gln Gln Asn Arg Asn Ala Ser
        195                 200                 205

Asn Asn Gly Ile Ala Ala Thr Gly Gly Arg Gly Asp Glu Gly Ser Met
    210                 215                 220

Ala Thr Asn Leu Glu Val Asn Asn His His His Gln Tyr Asp Ser Thr
225                 230                 235                 240

Asn Tyr Phe Asp Pro His His Asn His Pro Ile Ser Leu Gln Leu Val
                245                 250                 255

<210> SEQ ID NO 18
<211> LENGTH: 711
<212> TYPE: DNA
<213> ORGANISM: Cucumis melo

<400> SEQUENCE: 18
atgggaagag gtaagattga aataaaaaga attgaaaata ctacaaatcg tcaagtcacc      60
ttttgcaaga gaagaaatgg attgcttaaa aaagcttatg aattgtctgt tctttgtgat     120
gctgaagttg ctctcatcgt cttctctact cgtggtcgtc tctatgaata cgcaaataat     180
agtgttagag aacgattga gagatacaag aaagcatttc tgattcttc caattccgga      240 ttatcagttg ccgaagctaa tgtacagttt taccaacaag aagccaccaa gttgaagaga     300
cagattaggg aaattcagaa ctcaaacagg catattctgg gagaagcact cagctcattg     360
ccattaaaag agctcaaaag tcttgagggc agattggaga gaggtatcag caaagtcagg     420
gctaaaaaga cgaaaccctt gttcgcggaa atggaattca tgcaaaaaag ggaagtggaa     480
cttcagagcc acaacaacta tctgagagca cagattgcag aacacgagag aatacaacag     540
cagcagcagc agcaacagca acgaacatg atgcaaaggg caacatatga gagcgttgga     600
gggcaatatg atgatgagaa tagaagtact tacggggctg taggggcgct tatggattca     660
gacagccatt atgctcctca agaccatctt actgcccttc agcttgtttaa              711

<210> SEQ ID NO 19
<211> LENGTH: 693
<212> TYPE: DNA
<213> ORGANISM: Cucumis melo

<400> SEQUENCE: 19
atggggagag gaaagataga gataaagaga atagagaaca caacaaatag acaagtgaca      60
ttctgtaaga gaagaaatgg acttttgaaa aaagcttatg aactctctgt tctttgtgat     120
gctgaagttg ctctcattgt cttctccagc cgtggccgtc tctatgaata ctccaataac     180
agcatcaaaa caactattga gaggtacaag aaggcttgtt ctgatagctc agccactagc     240
```

```
tctgtcactg aattaaacac tcaatattat cagcaagaat cggctaaact gcgtcaacag    300
atacaaatgc ttcagaattc aacagcaat cttgttaggc acttgatggg ggactccttg     360
agtgctctta ctgtcaaaga actcaagcag cttgaaaata ggcttgaaag aggcatcact    420
agaatcagat caaagaagca tgaaatgttg ctagcagaaa ttgagtacct tcagaaaagg    480
gagattgagc tggagaatga aatgtgtgt attagaacca agatagcgga agtagagagg     540
gttcaacaag caaacatggc cgtatctgga caagaactga atgcaattca agcattggct    600
aattctcgca atttcttctc tcccaatatc atggaaactg ctggacctgt ttctttctct    660
catcaagaca agaagatgct tcatcttggg tga                                 693

<210> SEQ ID NO 20
<211> LENGTH: 1545
<212> TYPE: DNA
<213> ORGANISM: Lycopersicon esculentum

<400> SEQUENCE: 20
tgttgaatga tggaatgaaa tacaaactta caaaatttt attattttct actttcagaa     60 atcattttt ttattttta tttttacaag aaaagccatt ctttattgtt aaattatctt     120
ccttttttga aaaaaagat attgaccaat ttaacattaa aattacagaa aaacacaatc    180
atgttgcgat aatagaattg cataattctg tcttaattaa gtataaatca gctgactgaa    240
ttctatgtgg aactcaacaa atcaacccta actttcattt caacgtgcgg tttcacaaaa    300
ccctaaaaaa gttaaatctt cactttatct atcaattgac actccataac ggatttagaa    360
ttttaattcc atgagttaag catttctaga tgtttagtat tgagtcaatt atatgtttga    420
agttataatt catgtaactt tgcctatgaa tttatgcttc atcagaagtt atgatttcaa    480
ttaaacttgt atccttccct atagatatga tatgaattta tatcatcgag ttaaattact    540
tcaagtttga cggaaatatt attcttaaat ttcaaacaag ttgatattga ttatatgaat    600
ttttaccatg aattcagaag tagaattaat atctatgttt tcttaattaa acaaaatta    660 gagcccgttt gaataggttt agtagtcggt caaacctact tttaaatcaa ttttttgactt    720 ctgaaagtgt taggcaaata taaaaagtaa ctaaataag ttacgaagtg tctgacaaag      780
taaaaaatga ctcaaaacaa ataaaaatg atttaaaata agtcaaaaac caaaagtaga      840
tcccctatta cttttttattt tttgacttaa aagtcatttc atttgatttt ttattttta     900 atttaaaaag taaataaaat ggtaaaacat ctcttgtgtt tttcaaattg ataattatt    960 tttagtatag taaacaagta aaaatagtcg tagctaggga taaagttagg gtaagtaggg   1020
atataatata aaagaaaga aaagcatata agtattatgt ttttcttca ttgatcagtg    1080 tacaaataag aagtctttgg aagttgtgtg agttttcaga aagcctttga agttcgccgg    1140
aaaatagcaa tattttcaat tcaagccaat caggtctatt acgttgatat tttacatagc    1200
atcaaatttt agaagaaaa aatatatga aaaaacttaa atttcccatt cttccatgca    1260 tttttttaaat tttttttttt ttgcagattc tgaaatgttt ctctctgtgt tcattatgac   1320
aaaattaatt tgtgtttcgt gtggaactaa gtcaagcttt agatctatct gcaaattaca   1380
taggttatag aaatatgaaa gatttcattt ttatatctat caagcgcgtg cattttttt     1440 ttcttttaat ctttcactta tttgaaaggg aagggtgctt actatctgag taacctcctc   1500
ttgtcacgga aattttggtt gatcaataaa agatctcctt gaaac                    1545

<210> SEQ ID NO 21
<211> LENGTH: 714
```

```
<212> TYPE: DNA
<213> ORGANISM: Cucumis melo

<400> SEQUENCE: 21
atgttccaga atcaagaaga aagatgtca gactcgcctc agaggaagat gggaagagga      60
aagattgaga ttaagaggat tgaaaataca acaaatcgtc aagtcacttt ctgtaagaga     120
aggaatgggt tgcttaaaaa agcttatgaa ctttctgttc tttgtgatgc tgaagttgct     180
ctcatcgttt tctcaagccg tggccgcctc tatgaatatg ctaacaacag tgtgaaggca     240
acaattgata gatataagaa ggcatcctca gattcctcca cactggatc tacttctgaa      300 gctaacactc agtttatca acaagaagct gccaaactcc gagttcagat tggtaactta      360
cagaactcaa acaggaatat gctaggcgag tctctaagtt ctctgactgc caaagatctg     420
aaaggcctgg agaccaaact tgagaaagga attagcagaa ttaggtccaa aaagaatgaa     480
ctcctgtttg ctgaaatcga gtatatgcgg agaagggaaa ttgatttgca caacaacaat    540
cagatgcttc gagcaaagat agctgagagt gaaagaaatg tgaacatgat gggaggagaa    600
tttgagctga tgcaatctca tccgtacgat ccaagagact tcttccaagt gaacggctta    660
caacataatc atcaatatcc acgccaagac aacatggctc ttcaattagt ataa          714

<210> SEQ ID NO 22
<211> LENGTH: 771
<212> TYPE: DNA
<213> ORGANISM: Cucumis melo

<400> SEQUENCE: 22
atgagttgtt atgaggaaga agatgaagaa tcaggagtag taggactaag aaaatcatca     60
tcatcatcaa gaacaggaag aggaaagatt gaaataaaga aatagaaaa tacaacaaat     120 cgtcaagtta ctttctgtaa acgaagaaat ggtttgctta agaaagctta tgaactctct    180 gtccttgtg atgctgaggt tgctcttatc gtcttctcct cccgtggtcg tctctatgaa      240
tatgctaaca acagtgttag ggctacgatt tcgaggtaca aaaaggcata ttcggatccc     300
tccaccgcca tgtccgtttc agaagccaat actcagttct accagcaaga atcagccaaa    360
ttaagagctc aaatcggaaa tttgcgaaac cttaacaggc atttgttggg ggaatccatt    420
agttcgttat ccgttaaaga tttgaaaagc ctagaggtca aattggagaa aggacttagc    480
cgaattcgat ccagaaagaa tgagcttctg ttttcggaga ttgaatacat gcaaaaacgg    540
gaaattgaac tgcacactaa caaccagctg atacgagcaa agatagcaga gacagagaga    600
agccaacaaa acagaaatgc aagtaataat ggaatagcag caacaggagg aagaggagat    660
gaaggatcaa tggctacaaa tttagaggtc aataatcatc atcatcaata tgactcaaca    720
aactactttg atccccatca taatcaccct atatctctcc aacttgtgta a             771

<210> SEQ ID NO 23
<211> LENGTH: 11900
<212> TYPE: DNA
<213> ORGANISM: Cucumis sativus

<400> SEQUENCE: 23
ctaaagatag agttgataag cactttctaa aaatttgaag actcaaagta gctcacaaat     60
taaggtagta tgaaaaaggc ttccattttc aaatcttgat ggctattaaa agtaactttg    120
tcaaagtcca attgtaacta atgcttttaa tcaattattc aacataaaac tagttttgta    180
acaagaagct aattaattag aaagataaaa taaaatatg taaaatgaat tttttatttt     240
```

| | |
|---|---|
| cataaacaat ataaaaaggt tgaattgagt atatagataa tgaagtagtt gaaagtttgg | 300 |
| ggatgaaaca aagttggtaa aaaagaaata tattaccaaa ataggattta aatgtgtatg | 360 |
| gaaatgcaag tttgttaata aaaataataa attttacttt cttgttttgt agatatatat | 420 |
| ctatacaaag acatattttg aagcaacttt ctatggatac ttgacctta ttatcaatta | 480 |
| tgggttcttt cttggacac ccatcaaaac ctcattcttc tatataacaa aatgggtaga | 540 |
| gtggcaactc tctttttgg atattaattt catattctaa attctatttc aaagtagttt | 600 |
| atagctaaaa tacaaggtcc taagctcaac ccactcaaat tcaaaaaagg gatattatta | 660 |
| cacatcaaat tttcttctct tttttctct ctttcttttg tgtacaactt gctcaattgg | 720 |
| tctctcatac tcacattcca aatgaatata cagtgtcatc cattgttttc accccaaaaa | 780 |
| aaattccttt caactttatt ttcattcact agcttatgct tttttatca atcgaaaatt | 840 |
| taacatgttg ttagagtaga tatgttcgtt actcgttggt gttctacata tttcaagcca | 900 |
| caaataagat aaagtatttt ttttaacaat aaataagaga taaagagatc ataaggtcca | 960 |
| tcattagact atttcaacta agtaaggga agctcaaagt aagaggttaa gaggattcct | 1020 |
| ttctcttact ttgagcttct ctatttgaaa tgtcttgatg catctaccga tgtcttatgc | 1080 |
| tctagtatct tgttaaaaaa acgtaagagg atgcatgtta tatgacgt ctcatcatgt | 1140 |
| taaactttg aatcaatcaa tggttgtgac taaaaacact tcattaacta tgtatgaatc | 1200 |
| taaattcact catttcaatt gtttgctatt acaaattcgg tacggagttt tcccaaaacc | 1260 |
| gacccattca cactcctaat tattaaactc cataattaat ttgaaatatt ctaaaaatt | 1320 |
| gtatgagcct tcatcttgaa aatagtgaag caatcctcct atgagaccat acccaataaa | 1380 |
| gctaacaaat tttccacaca catatatata tacacacaga taatagataa aattacattt | 1440 |
| cttttaaaaa aaggaaaatg aaaaagatgg ggtttcaatg tataaacaga aggtcttatt | 1500 |
| ccaaccaatt ttttggggtc acttttgag agaacctttt atggggaacc catttcttaa | 1560 |
| ctttttccca taccatgaag aaatggatgt ggctaatggg actttgaaag tgaaccctaa | 1620 |
| aacattatat atctctcaat ttaattttt tatttaattt tttttttataa cttctttaca | 1680 |
| ttattgctct ttccttctaa ttagatcatt aattcattga ttaaccctct ttaatttcac | 1740 |
| accaagaaaa tagtaatatg gaagatcaat tttcaattta cttttctact ttaaatactc | 1800 |
| ttccctctaa acctaacccc acacatagct tcttcttctt ccacttctct tcactaaaat | 1860 |
| ctaatcttcc cttttttttt tcttctttta cttcatctca ccaaaggttt gttaattttt | 1920 |
| cttcataccc catcttcaaa gtttgaaact ttacatcagt tttttttata gatctactga | 1980 |
| taaaaatcaa aaccaatctt ttagtgtttt tttttttaa tttattttt gttggggat | 2040 |
| tattaattta gatttcaacc acggagttcc caaatcaaag tggagaagga tctgcctctt | 2100 |
| cccaaaaaaa aatgggaaga ggtaagattg aaataaaaag aattgaaaat actacaaatc | 2160 |
| gtcaagtcac cttttgcaag agaagaaatg gattgcttaa aaaagcttat gagctgtctg | 2220 |
| ttctttgtga tgctgaagtt gctctcatcg tcttctctac tcgtggtcgt ctctacgaat | 2280 |
| acgcaaataa taggtaattt cttcttcttc ctccttctct atttcattat ctatcgccat | 2340 |
| aaattttcat ttccttcaaa aaagcacaat ttttacaac cattttttt attttatttt | 2400 |
| tttaaaattg agaggattga ttaattgaaa attaattgat ggggtaattt aattattttc | 2460 |
| catttgttt cttaaatttt gaaattattt tcctacaatt ctgagctacc tgttatacaa | 2520 |
| gatctatgat ttaatgaatg actatgaagt ggagtcgttg gctaaaactt aaagcttagg | 2580 |
| gttttaccaa ggaatttcat tcttctttta agatttttt tttaaaaaaa tcttttaggg | 2640 |

```
ttttgttttg ttatttgtta tttgtttgtt tttaatttta atttttaattt ttgggtacaa      2700 atgtcatcca tttataagtt cgtcagccta agctgtcttt tgacagaaga tgatggtgtc      2760
atcgacttga tttatttcca tttttgaccc tttcttccat tacttttaat gttggtactc      2820
aactgacctt ggaaaaatta taaattttg caaaggggtt ggttagatat tgttcgactt       2880
taactgggtt ttttttctaa agaaaagaaa attttgatta tctatgtttt acattaatct      2940
ctttctttaa gggtgattta gtaaattatg ctcatattac gtgtgaaaat ttgaatataa      3000
tctccaagaa aaagaaaagt gaagttatga ttcagttttg gagaagagtt tctgatgaaa      3060
ttgatttgga atcaaactct tcgagttata attttgttta ttctatgttt ggtttcttgt      3120
tctggataaa catattactt ttttgaaata taaattttaa gtgattttc atgaaacctt       3180 tggcgtaata taccatattt tgtggtttat taattgaaca acttttttc ttttttttt        3240 ttcttttga taattgtctt atgtttggtt tcaattttag aagtttagta gatattttct       3300
tttcatattt actatgttat gaaaagaca ttgaatcatt taattgaaat actaaaacta       3360
aattaaagac gtaatttcca taatttgttt acaaatattt tattattatt ataatcttaa      3420
taaaccaaag tttaaaatag ttctatccaa ttggtggtag aatttagttt tattataggt      3480
tggtttattt aagttaattg gttaaaacat gtatatcctc ctaactttta aattaagaac      3540
attgaatata ccaaaaaata tcataaataa aaacattaaa attataactc tctaccattt      3600
gtgcaattct aatttgtaca agtgatcagt aatactatat ggcacagaaa tgataaaagt      3660
attagaaaac aaagttaaga tttttgtgtta acaacttatt acataattag attgattgaa     3720
taatggtaat ttattagtaa aatttttgtg ggttgtacaa taaataaatg aagaatggta      3780
gtgtaccata atgataatat aatatttgca aaaatgaaga agggtgtgac cctcttaact      3840
ttaatttgta gcataaaaat agaaaagtt gataaaatag cttcctattg ctaaaaaaat       3900
gttcatattt catcactttc aaacccttc ttctctttag tcaactcaga agtgatattt       3960
cattaatcaa atccgacaac caaatattgt attgccacca ttattctaat tcatcatttt      4020
tatttttatt tttatttat gttttgaga tgggatggga tgagtaaaag agaaagtggg        4080
gggaaatttg aaattttcaa tttgaaataa tatttttga ttttaggatt atgaaagtga       4140
aaggggaaaa tgagtgtatt ttcatttct ttttgcaatt ggaagagaga atcatttcta       4200
tttctatgaa actttgatcc tttcccttct ctttacgcta aattaggcct tttaaaaaa       4260 ttgggttttg aaacccacaa gaaccttacc atatacttcg atactggaaa atagactttg      4320
agtttctcaa atgtaaaatc tagattttga aagtattgaa gttagcaaa tgttttgtgt       4380 gcttggtctt aataatagtt acataataat gtcaaatatt aaaaaattta tattctttat      4440
cagtaacttc cctcttataa atttaaatcg tttagaaaaa tctacccact acattacaat      4500
agcctcactt aataattctt tctcctagtt aaaccacatt cttttaatat agattattga      4560
acctcctaac acttttgaat gaataatgtt cataccaact actattaaac taagttcact      4620
ttagcaaaca taaactagac ttgaagaaac caaatgcatg cactaaacga ttgatttgga      4680 gaaatacaa atgaacgagg aagaagtgta gggttgagag tgatatttga aaccacaaaa       4740
atgaaatgat taaaaaaag atgttgtaat gtgatttgaa gtatttaaaa aggatttgtt       4800
ggaaaggcat attattgaaa aggagaagag gaagagagaa atgaggattt aggtttaggg      4860
ctaagtatta tatccaatga acaaagggaa aatgaggagt atgttaatag aaagatttta     4920
agaaaatagt atgtatattt atgtggtaat aatggatgaa attctgtggg attttctgac      4980
```

```
tcccaatcag cctcgacgaa actaaggtat cacacgccac cactcacttt cttggaatcc   5040
ataaacccTt tttttTccct tctaaatcca ttggttctta ggtatgtttc tctttctttt   5100
catataatat ttgtatgaac aaatcaaaat tatcatttaa ctatctactt ccacattata   5160
attggatata tactaagagt aatatatttt gaattgtact gatcatctgt ttaaatacgt   5220
tataaattgg atacttgtga aaagtgaaag gttgtgaatg gattgattgt gttttaaaat   5280
gagtaaaaaa aatgacagtg ttagaggaac gattgagagg tacaagaaag catttgctga   5340
ttcttccaat tccggattat cagttgccga agctaatgta caggtaattc atttcttatt   5400
ttcctttcat acacacacac atatatgtac acttttTcTT TtccttttTt tggctcctta   5460
ggatccattc ataaacactt ttaatatgat taatcaactg tctatacaaa tgtatggaat   5520
ctattctcct gcttacctca aagcatacta ctacattcta taatgcattg ctttgggcag   5580
tcccaacgcc atgaccatct tcatcatatt tccatctttc tcacgctaag aaattcaaag   5640
gaacaaaact tatgagaaaa atgtgaaacc acaaccaaat aaatttagca tccgttttgg   5700
aatgacttaa gaaaaaaatg ttttctaaaa aatgcatttt tatttaaaca tattTttTcta   5760
aaaactcctt gaaagaaaaa tgcatgtgtg tttgacaact ttTTTTTtcaa aagtgttttt   5820
aggtaaaaat ttgtttgatt tgtaatagag taaaagattt atatatatat atatatagaa   5880
tttgtcagtg gatattttga tagaagggac aacgatcatt gaggatgttg gtttgaggtg   5940
gtctgggaca gttaccgtaa aatgataatc aaaggttggc aaccgtggtc agtggaagtc   6000
aaacgatgac aattatcaca aaaaaaaaat agttgttggc agttagtcaa taacagtcct   6060
agaaaactga ttgacaaaag ttgatcgcta acagttacca tagaacaatc gacaaaaata   6120
agtcaatggt aaaaaaaatg acagatgaaa gttgatagcc aacgaaaaac ggtgaaagaa   6180
aatttggcta acgacataca gggatggttg tcaaaggttg gttggtgaag atagttgaag   6240
atattggtct gattgtttca tacaaattag ggagattaac cattaagcac acaaaatcta   6300
ttttactaaa agttggttTT atgtgtttat cctaacccag gttatTttat aaatTtattt   6360
tttcaaaatt tattttaggt ggttgccaaa cacatagtct tttctccaaa acaattttTT   6420
tttttaatTt aataacttga aaatgcaatc gagacacacc tttattgtgc acagtagaga   6480
tggtcatcgc attagggctt cgatacacat ggtcaatgtg atagagcatt cttgcataag   6540
cataaattta aatttcatac atttgtaaaa ggtcggtcat ttaatcataa aggcaccttt   6600
gaatgagtta tccgtttaaa aatttctata tatggctttt gaaaattatt atgattttTc   6660
ttacaattct tttatgatcg tttcatcttg ttgtttaaga aatacttaca tgtagtttga   6720
taattatttg gttTTtcgtt tttagttTTt gaaccttgta cttgtttcac atcaaatcgt   6780
taaaaatgat ttccatcatt ctctatcata cctatctcgt gtgttttcca tctctctact   6840
acaaaataaa aaaatggaaa actatttttt ttaattactt aaataaaatt tgtgagatga   6900
agaggtgcaa aagcattgag acataaaatg cacccaagtt atTTTagatc ttattggata   6960
ttggatcaac atattTaatc aagtTTTaga aacaaaaact tttacgaaaa tTTctttagc   7020
tttTTTaaat gaagcggttt tgttcggttt tagaatcggt ttaaaacatt aaactgaatc   7080
gaaccgtata agaaacgatt tcaacataac acaaattgca tacaattgat gtcggttcag   7140
tttggttTgt caaattggtt cgattTtaaa atattTtatg aacaccctta ctcgttataa   7200
gcttagcttt ttcatcaaaa actgaaagca aaaattcaag tagttaaaga aagggagttg   7260
aaaaacttgt tccggaaagt ttagttgttt catccaatTt ctaattacat aagatcatat   7320
tttcttaaga aacacattcc ttcataatca aatTtcaaga atcaaagtaa attTtcaaaa   7380
```

```
ccatcagtac agttacgttt tttaaaacag tgctagaaat tgattaaata ataaagaata    7440
tattagtgta catagacttc ttaaatatat ttgaaataag ttctactttt ttcaagtaca    7500
aaatacaact ctttctctga tctctaaagc caacttccaa acaatttatt aaaatatatt    7560
tacaccaaag aaaagtatat ttttgtacaa aattttgact catgtacaac tcctaatttt    7620
aacaatccaa aaaatacggg ttttgtaggt aataaaaatc taaattctaa accctaaact    7680
ttaacattat actcttttag caaccatttc tttgctttt ctttctaaat taaacttctt    7740
tcctttcttc ctacactaat ttgtttttat caattgttga aggtagataa caaaagaag    7800
aaagttgagg ggacaagagt gtctatagac ttaaattttc aaaaacaaaa tagttaccga    7860
atgaagtttt aagatttgc ccttcccaaa cgggttttat gattttgcat catggcaata    7920
tttcattttt agttctttta aatctgtgtt cgcatctttt caattttaaa tatgattttt    7980
accgttgtta aacatttgaa cttttaatcc aatttgagga gggagggagg gagggaggga    8040
gggaggggag ttcttaaaat tactcttcct tggttggtaa aattatatac tattagtttt    8100
tataagattc atgtgtgaaa aacttagtgt tttctgaaaa gaatagaagc gatgatcaaa    8160
tgatctatgg gcagatgagt gcctttgtat aatatctgtt ttcttcttcc ttggctcttc    8220
tccaacccctt gatgttttgc cctttttta tatttattga cagaccattt cttgtataat    8280
ttattgatat atttaactcg aatgaagttg ggatataatg agggtgttgc caggtatcta    8340
acgtagttgg gattcttttg ccatatcttg taatttttt atgctctatg gaacgatatt    8400
gtcactcctg tagttagtgt actaaatcta atactttctt ttttgtaatt atgatgttta    8460
tactattcct ctctgctgga aggttcttct ctagtttctg ataagatttt aaactcaaga    8520
gaaaatgaaa tacgaaatct tgggggcgat gatattcgat atttatatgt tatgttgtaa    8580
tgttaatgtt atgacctcaa atgaaacatt ccagttttac caacaagaag ccaccaagtt    8640
gaagagacag attagggaaa ttcagaactc aaacaggttg tttggttaat tcaaatatt    8700
ctaaacacta cacacacaca caaaattacc caaaaaaaca accctttagt ttggtattaa    8760
tttaattacc ttcatcaggc atatcctggg agaagcactc agctcattgc cattaaaaga    8820
gctcaaaagt cttgagggca gattggagag aggtatcagc aaagttaggg ctaaaaaggt    8880
ctctcccatt ttcaactctc tcattttgat ttctcttctg tcttgaagta ggggagtccc    8940
acatgttaaa tctctctagc taacatgatt ttctctcctt tcaatcctca ttgcattcca    9000
aatatttata tatgatcgaa ctacattctt ttatcaagta tattctaatt ttgtgttcct    9060
gtatcaaagt aggaagtttt gtgtttgttt gtgttgaaga agcgtattga tatcataaat    9120
ctcattgatt tatgcttttg agttgaatgg tagcgattta gagtatgctt gttctatgag    9180
tttatatata tttatataca aattttaaaa aataacatta ttttcatgtc aatcaacaaa    9240
atagatgtat atatacagca ctattttca tcacccgtta caaattgctc gttcatatca    9300
aataaattta taaacgacca tccttcattt atgtgtgcag aacgaaacct tgtttgcaga    9360
aatggaattc atgcaaaaaa gggtacgtat aactaacaaa gattcgttaa aaaatataaa    9420
gtacttttaa acatttagaa aatcctttat cttgaacata tccattctct ctctcttttg    9480
taaactataa ttaagcattt ttcggtgcag gaaatggaac ttcagagcca caataactat    9540
ctgagaacac aggttaaatt ctcaccttt atccaaaaca ctttggagtt tatttcaatt    9600
atgatattta ttcatcaact ttcaatattt ccaaaactta ctttgcactt ttcatttttc    9660
tccattttaaa ataaggtgga tcgatgcaac agttaacagt taatacatga aaattgaaag    9720
```

```
agacatgtga catcattttc agcatcattc atgtaaactg atgtgacata taggcaattt   9780
ttattattaa cgatgttgaa aatcttttgt atgatcttaa ataatactgt ggtctttcta   9840 attttttatac aagcatcaag agaatatctc acatggtatt agactaaatg tatatcgcag   9900
ggcttcctag ctaatagaaa agctcatatt attattggag ggagtagtcc tcccttgtaa   9960
actcgggtca actaggacta caattttgga aattaaatgt taagctctag tctttcttta  10020
tacgtcttaa gtacttgtaa agtatctaat ttgggtataa acctgtgttg ttgtaaaatg  10080
ttattctaat gaataagacc ataattgaaa taaagtcgaa tgttagagag atatctggta  10140
taatttaacc taaaaagaga aacataacca atatgttttg tgggtttgta tagattgcag  10200
aacacgaaag aatacaacag cagcagcagc aacaacagca aacgaacatg atgcaaaggg  10260
caacatatga gagtgtggga gggcaatatg atgatgagaa tagaagtact tatggggctg  10320
taggggcgct tatggattca gacagccatt atgctcctca agaccatctc actgcccttc  10380
agcttgttta aaatttataa ccctcccccc ccttcttatt tttattacta ttattattca  10440
caatatgcaa ttacccagga tgtcaaataa tactgccttt tggagctcta tgcttctggc  10500
tgagatagtt ctcatggtat ttattttgt ttagtgtcat atatatatct atatagtgtt  10560
atagtacaat caaatgatga catagacttt tttaatatct atatatattg acaaaaagaa  10620
aagaaaatgt ttttttttaa aacttatttt tggtatttgt ttatttccag ctcatcttag  10680
gaatatttca acaataaaga agaaagtata attgtgtttt tctggtgatg tatattgatc  10740
ttcgttcgtt ttattttgtt agtatatatg ttgggataag ttgggagtgt tgtttggatt  10800
tatattgtgt ggtttgtttt taacaattgg tttagagggt tggtttatgg tattatttgg  10860
acaaaagact cacttgactt tcatgtgttt tagatggtga atttgtattg caaggtagag  10920
gtcaccttgt agaacagtca caattgtatc aatgttatac ttgccacata tgctctattg  10980
tttagtttag attttagcat aaactttgat ggaagagttg aactacccta tacagcattt  11040
attctcaata tatagagaga gagagacact gaacccaaac ctataagttt tcttcatcct  11100
tttagaagtt tatgcttaat caggccaaac ctatacatga ctctgagaag cttaatcgga  11160
tcacacaaga gtgatatata tgagtccaag agaataggat ccaaactcca taagagtaa  11220 gccaatctcg accttaaggt ggacgcaagc caatttgata agggggtgat aatagtgagg  11280
acgactatcc ccactagttt gtggccttttt cagatgaacc aaaaaataaa acgaaaacta  11340
tttaattgct tcatccacat ctctcttgaa tttttcttcc tttgttgtaa agatttggta  11400
ttggaatttt ctaaagtctg ttcctttcac caagtatgtg cacgtccaaa aagaaaagta  11460
ctcgaactaa ttacattgtt ctgcattttg tcttaagaaa agaatgttgt gttatttga  11520 tcgtagttct tctggtttag agtttcgtgt tgtttcgatc agtagctggt tgttttttaaa  11580 gtagaagaaa aaccttttgtt agcagacaga ttaatgaagt gttatgttga aatctgatga  11640
aaggtcaaaa gttcatgggg agactccttt gattaactt cttgttgatg ataagaatgt  11700
agcttgatta agatcaactt tgaattatag tgataatgtg atttatatca caattagtac  11760
tgtgtggata agttagtgag aatctccgca ttaaaatcat aatatgttga tttatttatg  11820
attgaatatt atcaaagaaa taagatatct gatcataggg tcaaagaccc caaatctaca  11880
tgcagtatca gcaaactggg                                               11900
```

<210> SEQ ID NO 24
<211> LENGTH: 7901
<212> TYPE: DNA
<213> ORGANISM: Cucumis sativus

<400> SEQUENCE: 24

```
tctatatgta gggatataat gaaaagggtg tgtggtttgc aagtagaatt tagtggggtt      60
ttggtctggg tgtgtttgta tatggagtgg tgagataagg gatggaatga gtgatgttgg     120
ggttgattag attgtgagca ttaagtgatg agttaaaaga gagaagacca tatgtaagaa     180
tagattgtgt tgttgtagaa gtaagtaagt aagtgaatta agaagagaga aattaaaggg     240
gcaaaaaggt aaaagaaaga aagaaaggaa agaaagaaa aagtaaagga aagaattgct      300
ggttgtggtg ggaatttgca gatgcagaga agttttaatt cagctattaa ctccaatgtc     360
ttatatcaat tttaggcaaa ctcccacttc acattttta tttctttttt tttttgtatt      420
tacacaaagt tgcttagtaa agaagcttca tttttctctc tttctttta ttggaaattc      480
tttcccattc atcaacttct ccttctcacc tcaaacccca atttctccaa ggtttgtttt     540
ttcttaattt ccattcatca tctttttca accccctact tcaaaaaaaa aaaaaaaaaa     600
aaaaaaaaaa aaactttaa tttcctatat ttcttccct tcatgcatct tttttttttc      660
cgttatcatt tagatctagt gttcatccat aaaactaaag aaatcattta tcatcatctt     720
ctactttagg tactgatgat gatctgttaa gatctattat gtattgttgt aaatgaattt     780
agtaattatt aaaattgatt aattttttt gttaggaaga agctgaagaa gaagaagaat      840
tcagaagaag gattttatt ggaagatcat ataaataatg gggagaggaa agatagagat      900
aaagagaata gagaacacaa caaatagaca agttacattc tgtaagagaa gaaatggact     960
tttgaaaaaa gcttatgaac tctctgttct ttgtgatgct gaagttgctc tcattgtctt    1020
ctccagccgt ggccgtctct atgaatactc caataacagg ttcttccatt cctacctcca    1080
ttattattat tattcttttc ctcttcatcc atattttact tcattcccca acacctatac    1140
cacaccatta atattattcc aacttctact taattattac ttttaattat ttcctcatct    1200
tcttcatcct cttttctttt tcttttttc ctttttcttt tgggttttt aggggcatac     1260
atgaagaaat attgtgttta attaatcacc tccataagta ataatataga tttagtcttg    1320
gtttatatac ttttaactt ttgtgtccat aaaaataaga ttttatact tattcctaac      1380
tgcttttctc aaaatgatca ttattattgt aactcaactc ttatacaact tcttctatcg    1440
gccatctcga agttggaagt tttatttctg aaaaaaattg ctttcaaaag cccttttaac    1500
ctcaactttc acatgagtat ctacccagta tttccatgaa ttttttaagaa gtttgattag   1560
acacaagatt gaaatttcaa ggaaatatta tactgatgca aaaatttaat ggttaacagg    1620
gtaatttatt taacaaatta taatgtttaa caactaaata tacacaaacc taaacattca    1680
acaacttatt aagaagttac aaaatttgat agactcacta acagactttc aacccaccca    1740
ctgtgaaaag aagcagtatg gatcttgaga gttttcacat gtgagcaagg ggaatctcgg    1800
ctagaatgtc aaagtcaatg tcaatgacaa caccgatacg taaagttttt ggactaaact    1860
tgtaattatt cctaatggtt tattcctaga gggaaatatg aacaaaggat gaggaagaaa    1920
aagtaagaaa aaattggcca tatatatgac tgccaaaacc ccattttca ttgtgttgga     1980
tttggaatgg atattcatca aaagtgtggt ttccttgtat agtttagatt tatgaggcat    2040
gagctatgtt taacaaaatt ctgccctaaa tatgtcatct tttttcaaca atgaaacaac    2100
tgttcatttt acattaaaag ggaagaaaa caaacacttt cttcccttt caaactcaat     2160
gttcccttca tttctagggt ttcaaacctt acacctccga ccaaccccttc aaaataacat   2220
tataaataac aactttttta atttttacag aattagaagt ccttttgtaa acaaatttag    2280
```

```
ttgaaatatt tgagtgcacc ttctcaatca ccttgtttgt ctcttgttaa aaataacctc    2340
attgggtttt aaaaattaag ttttttgtcc tattttttcc aaatttaaat ttgagacatt    2400
gttttaaatt ataagatcta ttaaatcatc tatcaatgtt gtaaatattt tgtttcattt    2460
tgcacaaaca actctttaaa atttcatgaa aatagaaata ttgataaagt atacatattc    2520
ttagaataat catgaaacct ataaaagtat ccaaattaat aagcttaaga aaatctaatc    2580
atcgtgtttt gtaaatatat attgtaaacg tcctccatat ccaattccta gcttagtctc    2640
tctcccctca ttatgttttg atcttttttt acttagatgt ttttcttct cttattatgt     2700 atcatctgct tttctggact tgttttgtt gatttccaag aacatttcct atttctttgg     2760
cttttctgtt cttgtttgtg tgagtgtgtg tttaatgtt ctttaataat gaatcagatt     2820
attgtctgtc aaattttgc cccatcaata ttttaataa ctatatatgg ttaattattt      2880
tgttttctag aacaatgttt cttatcagaa atgtattatt gtttaacttg ttcaaaactt    2940
tccttttctg ttttattatg aaagtatca attcatacta ataactaaga tttgaaattg     3000
tactaattca aacctacgtt taaaccttt ttttaaaaaa aaaatgaac ctgtaaactg      3060 taaaagatc agtattagtt ttatttatgt gtgaagcttg agaaaaccaa gagtgtgagg     3120
tctgacaaaa cagctttgaa acaagctttt ccaatggcat ttaaattttt ataggactat   3180
tcaaaacact tgtctttgc atatccattt tttcacaccc ctttgtattt ttccctctt     3240 gtgtaaatat ccataaacat aatctctata cagaatctat agcccataca tatatacacc   3300
atctctcttt cacttttcca ttttaagcta tcataattag tttaagtttg tttcaattcc   3360
ccatatctcc cttttctct ctttgctatt ttttcttc ttccatgggg tgttctttc       3420 aaatttatag aaaaccctc caaaacaaa cctactggta ccattgccta ttctcatgtc     3480
aacaaaaatt taagctcctg acattagaga gattttgta gggtttgcta ggagaaaaaa    3540
taaatgacca ataccagaga ctgcccatta tactaccagt cttctcatat gctttgaata   3600
tctagatttg aacacactca catactgatt atacaaagag agaaagaatg tttcatatgt   3660
aaactgtaaa ccttccaact tgttttgggt gagtggctcc tactatcata gccatatatt   3720
attaataact aagggtacag taatatttaaa atgagatgat tttgttctta attgacttct  3780
attagtgatt ctaaaaattt gagtttccat ttttattatt ttattttgca aatacgtgat   3840
aaggggagag agaagggtta agatggcctt ttataaactt ctcagagaac acagctgatc   3900
caaaccatct tggtctatat ttattgattg ttgggactaa aaaaaactgg caattaaatt   3960
tggtattaaa gaatataaag aaattagaat gaagcatgtt aaataatatg attgtacagt   4020
ctgttttctg aaatttcatc attttcatga caaagctcag ttcattgaag gatctgtgtc   4080
tgaacataca catttacata tattaggcaa taattggaag tgattttgca tctgctttgg   4140
ccattaaaaa aatcttgctc ctaaatatct tctgttagct tttctaaagt cactttcatc   4200
acacacacac acacacacat ttatttgctt tcatcaatta attaagacaa accaattgat   4260
taagacattt tattattaac taaataaaag taaaggtaca aatctatatc tgtcgtccat   4320
tcaacccaac taaaaaaaaa aaaaaaaacc tttagggaa ggaagaaaat aaaaatctag    4380
ccaatacttt tattattatt gttgttttg tattttctg attaaatatg tttgacactt     4440
taattttaat aggaatgtgt tcaaaatata ggggaaaaaa tcaatatatt tccaaaatat   4500
aacaaaattt tagtatgtat tattactaat cgataaattt ttaatttagt atgtagaatt   4560
acttgtaata tatattttaa gctgttcttc tcattttaac aatgtaatgc aaaggtaagc   4620
cttgcttttg aacaaaaagg caactcattt gttatgatta gaagtgtaag actttcctaa   4680
```

```
atgatacact aaaataaaat aatcaaagtt aaggttgcag aacattgaga atttggtagc    4740
aaaagtttag tatattaaaa acctaaaagg ttttgcagat tatttgaagt tttcctcccc    4800
taaatttatg gaaaaaagca agctcacatg ttaaatgcac ttgcaaaatt tgagtgtaga    4860
tccaagagct cgaggtcttt tcgactttat gttgtttgtg tatagtagta attagctagt    4920
ctagtagtaa aacgggtttg aagccgcaat tcttacatta gtacatagtg atatttggtt    4980
tccaatgtca tttcattttc caattatata ttaactaatt ggccgttgaa ttggtaatta    5040
ttttaagatt aaatatgctg tgttgattag aaaaacaaaa aaaaaaaaga gtgaatgaat    5100
gtttggtaat gaagaatatt aacaatggaa attggtttgt gtaattatat gtgaaaattg    5160
cagcatcaaa acaactattg agaggtacaa gaaggcttgt tctgatagct cagctactag    5220
ctctgtcact gaactaaata ctcaagtcag cttctctctc tctctctctc cctctcctta    5280
attaattatt tttgaaatct cgagagtaat tttagacatt caaaagtgag tgttataaca    5340
catacacgat gttcaataaa ttcataaggt tataatatat aacaagttaa attatttggt    5400
ttcatggtct taaaagtttt ctctagctat gatatagatt ttttttcaca aatttcttaa    5460
tattcatgaa gcctaacatg ttattatgat atgatatatg aagtattatc agcaagaatc    5520
ggctaaactg cgtcaacaga tacaaatgct tcagaattcc aacaggttat tattattagt    5580
gactttaata cgccattcca tttataaaca tatataatat ataatattgg gctaaatata    5640
tagttttatc tttaatattt gtgtctctct tttgtttgta ttctttctct ccaatttcgt    5700
ccctaatttt tctttgtgag tgtgtgtgtt aagtatagag gtattaaaga caaagattag    5760
ggacgaaatc agaagaaaaa agaaaaagaa agaaagagg gaaataaaat attgaaaaag    5820
aaaaagatta tatatttagc caaaaagaaa agaaaaatga aggtggggt tgaataagct    5880 actctcatgt gttgaagcaa tcttgttagg cacttgatgg gggactcctt gagtgctctt    5940
actgtcaaag aactcaagca gcttgaaaat aggcttgaaa gaggcatcac tagaatcaga    6000
tcaaagaagg tttttatata tacattcttc tctatcagtt gaagattgaa caatatgcat    6060
tctagttcta tgcatatata tttagtattt gggcgatgtg agtgtttct ttgtcaaaac    6120 atttgaacgt tacatctctt tttgaatttt gtgatcatga cattagattg tatatttgtc    6180
ttgttttgtt ttacaatatg gggtgggaaa aaaatacaac atttaacttt tgcgagcttg    6240
ataaaaacaa atactatatt agtttaagct atgctatatt ttcttttcca agaatgtctc    6300
atgattaatt atataaagtt aagagtaagt aatatatata tatttgtctt cttaatttgt    6360
tgaacagcac gaaatgttgc tagcagaaat tgagtacctt cagaaaaggg taagtaatct    6420
agactgaaac caccatacac acatataccct ttctaattaa attcctgaac ttttggtaaa    6480
agaaaacgaa agaatttctt gtttcaattt atataaaact ttagatatat aattgggatg    6540
cttttcgttg tattaggaga ttgagctgga gaacgaaaat gtgtgtatta gaaccaaggt    6600
atgtatacat atcaaacatt atgattcctt gtatatgtat gtacatatag atcagagaga    6660
tgggagattg aaatggacaa tatatattat aggattgatg ctacatttgg tgactataat    6720
taatataatg tgtttcaaac atcaaacaga tagcagaagt agagagggt caacaagcaa    6780 acatggtatc tggacaagaa ctgaatgcaa tacaagcatt ggctaactct cgcaatttct    6840
tctctcccaa tatcatggaa cctgctggac ctgtttctta ctctcatcaa gacaagaaaa    6900
tgcttcatct tgggtattct ttctttattt taatttattc tcatcaacac atcttcaaaa    6960
tctatgttaa cattaagaaa gattcaattg gataaaacca aaaagtcaat actgatcttc    7020
```

```
tgagttttc  ttttttttt   ctcttgtgat  accacaggtg  atgctgtttt  ggagaccaaa   7080
atgatgggga  caattgtttg  ttttaattaa  tattcagaaa  atcattgaga  ttacaaaaaa   7140
gaattaaaat  aaaatatgcc  catcattctc  tgaagtacaa  aatttaatta  atttactca    7200
atgatcagtg  atgatcagag  cgtgagatgt  gatttaattt  gcagtttgtg  tgtttcaaat   7260
tctatataaa  tgttattata  tatactacat  acatatgata  tgatatatat  aatatgctac   7320
aatgactcta  atgctaatga  tatgtaattc  tatggatgat  ttttgtggc   tacatggacc   7380
aatatgtagg  aatgtgaaac  tttggcaact  tttaagtttc  ttgctttttc  tcttaaatat   7440
ggttttatct  aagtttaatc  cattcaactc  ttagctttt   ttcttttctg  tttatgagaa   7500
tatatagctc  tcttattaaa  ctgttgttca  ataagtgct   atatattata  cacattattt   7560
tgtaggtata  gtatatttta  taatatcaag  gcataatgca  aaattcataa  atagggcttt   7620
acagaatgac  aatggattta  attacatata  caaatggttg  catacatgaa  ttttctaaag   7680
acactaatat  gaatcttcat  atattgatga  aatgtcacat  attttttttt  atatatatat   7740
attactagta  taaatgtaat  gtaatgttct  aagttagaat  ggggacatga  ttgaaccgat   7800
atcatattta  aatacgaaaa  atcttagaac  atgatcaaag  taaggtaaag  ataatgactt   7860
aaaaaagtaa  aagttactta  cctataccaa  cgagatatac  t                       7901

<210> SEQ ID NO 25
<211> LENGTH: 7301
<212> TYPE: DNA
<213> ORGANISM: Cucumis sativus

<400> SEQUENCE: 25
aaacactaat  taatcattaa  tttttattgt  gactgatgaa  ctctaaatga  ggggtttaga    60
gagagtatta  gtttggcaga  tcatatagaa  tgtttttttt  tccatataac  agctatatgt   120
cattatcttt  tgattttgtt  atggctcttt  ttattctcta  atttgtgtaa  agatttttaa   180
catcaagctc  aataatgcaa  cttattccaa  catccctgtc  aacccattaa  taatcacttc   240
acaagtcctt  ttcctttctt  tctctttctc  tcttttcatc  tctctctctc  tttctcaaga   300
aaaagagttc  tagagaattt  gagatgccat  tgtaatgtcc  aagcattatc  agtcaccact   360
cacaagaatg  attaaggaag  aaggaaaggt  attttgatta  tataatggga  ctgttacatc   420
tttaaccttc  tcttttgttt  cattacttgg  attactttac  tctaaacaaa  atgaaaaaa    480
aaaagaataa  taaacaaaaa  tttacagcta  atagaaaaaa  gttgcaagta  gaatgatttg   540
gtaaataaac  atctgtatag  ctgataaagg  gtcattttct  ttactttata  aatacacaca   600
cttctttggc  taccttactt  ccatttccct  cttctcttct  tctaatcttt  ctgaatacaa   660
gctgtgtgtg  tagagagatt  tcataaagac  agcaaacatc  ccttctttt   gttctgtttt   720
aaaagttccc  ttcttcaacc  agctcttttc  ctcatcaggt  tagtgatcaa  aatactacaa   780
aaaataactt  aatatatact  tgaacaacat  ttcattattg  tccccaaatc  tctctgtctc   840
ttaaaccaat  tgaaaaaga   acttagattc  agcttctgat  tctctcctgc  tcattccact   900
ttgtaaatcc  ataagaatga  gactgaaaga  gcattgtttt  taccccaaa   aattgtatct   960
cataacatgt  tttgtctcct  ttcttatggg  atcaacaata  atagtcagca  aaatggaaac   1020
aaaaatattt  gaagatttgg  gttttgattg  atgattgatc  tgtttggaat  ttgatttagg   1080
gtaagttgca  aataaagggg  atgttccaga  atcaagaaga  gaagatgtca  gactcgcctc   1140
agaggaagat  gggaagagga  aagattgaga  ttaagaggat  tgaaaataca  acaaatcgtc   1200
aagtcacttt  ctgtaagaga  agaaatgggt  tgcttaaaaa  agcttatgaa  ctttctgttc   1260
```

```
tttgtgatgc tgaagttgct ctcatcgttt tctcaagccg tggccgcctc tatgaatatg    1320
ctaacaacag gtaaaacaga aacgctttta ttaaatctct actgatttt acattaatat    1380 tttgttcaaa tcttctttt tcctccaaag ttctagattt gggtcatgga agttttaagg    1440
aagggcaaga ttttgggaat ctgggttgta ttgagaatat agtcatttat tttttttggag   1500 aagatttgag tggtatgaaa tcaaaattta cccaatttct ttttccttt tgcttcatcc    1560 atgagttgtt tttgagtttg tgggatttt tctgatgttt ttgctataat tgtatcagtt    1620
tgctggttct cagtttggtg tatacataga tctggtgtaa cagatggaaa gataggggcat  1680 aatatggaat ggttaatgga aggttgaaag gagtaagggt tttggtaaac ttatggtggt    1740
ctctgagatc accttcttta ccttaccttc ctccattgtt taaagttttt ctgtttcttt    1800
cctttttact tccattattt cttttttctc tctctctctc tctatctata tgtcatctca    1860
ttagtccaat tctcttcata tttccttgac atttccttag tagaaacgtc agttttggat    1920
attaagataa agaaagtaca gtttcaaaac tttgtcaaaa gaccatatag aaataagctt    1980
attagggttt caaccaaag aaaaatggta aagaaaaga aaaactcgta ggtttccttg     2040
aaacatgtta aaacacccctt ttccaaccaa tcacttacaa gtcaagattg aactgcctaa  2100
ttagtttcca ttcaaaaccc tcaaataata atctcattag ctcatctttg ttttttccaa   2160
atatataaat taatcaatca gctttgtct agatcattaa tgggtaaaac ctcagattaa    2220
acatgtttaa aagaaaacta aataaaagcc ctaagacaaa tttatgggaa atgtatattt    2280
caaaaaaaaa aaaaaaaaa gaatggaga ggaaaaagtg tagcttttct accacaaaca    2340
aatggagcca atagcaagtc agaaacttta cacaagtttt atgtttgtct ccattgtttg   2400
ggaaaagagg cgtctggttt tagggttttg gttctgattt ttggtctagg gcttcaagaa   2460
tctttggtca cgtcactcaa tatttttcag ttttcagcct ctctgacaaa caaaagggtt   2520
tctgtcacaa tttctaaaat gggtttcatt ttattttcct acttcagatt caattcaatt  2580
ctaagtcctc cccagcaatt tctattcaaa accttgcgca tttcttttaa aacccgtttc   2640
ccccaaaatc tctttcactc tcactctcac tctctctctc tctctctctc tctctctctc   2700
tctctctctc tctctctctc tctctctctc tctctctctc tctctctctc tctctcatac   2760
ccatgcccca aaatctctcc ttttctcttt cgaagttcaa accacaagaa caaaccagag    2820
aaggatgatt ggattgaaga agaaactaaa ctgggtttcc tcaatttaac aaaaagtttg    2880
aatctttgta caaaaatat atatatttt agagagaggt tagggtacgg aaagtagtag     2940
agccaagcca atgggacagc ttgagcattt atcttaatag gacagctatg gcagccactg    3000
attgaaacgg acggctatga tgtacacaga gtttgagaca caaggattct taccgtcaat    3060
ttctttttcc aaggttttaa tgttgtatca aagtggataa gaggatgtaa ttaagctgat    3120
tgtccattga acaattgtaa ctattgacag ttggcaaatt cttgacccctt gatttgatta   3180 agccaatcat aatgtttgat ctctgcaagc atgtctcaga cacccaatca caacctcgac    3240
gaaattaagg tatcagtgca tcggtaaagg aaataattga tatttaaatc tgggaacttt    3300
tttcttttta ccttaaacct tacattctgt cacatctatt gagagaggca attcactcta    3360
tgaagtgatt tcttcatta attttacttt ttgtgggggt tttcgtgaag aattcagtta    3420
actcagagaa ttgggttaat gtgacagttt agaaacatgt tctttttaa caataaaaag    3480 caatgtttaa tgcttgatt gtatttttt atacttctgt taatcataat tttacttaa     3540 tcgacgttgc atgattaagg agtctcaatc aacttgaaaa tggtgttgat ttgggttata   3600
```

```
ccttggttaa ttgtagtgtg aaggcaacaa ttgatagata taagaaagca tcctcagatt    3660
cctccaacac tggatctact tctgaagcta acactcaggt attcgtactt tttaatttca    3720
ccaaatttag agaggaatgg ctgttcatct gagtgttaag catggaacct aaacacacat    3780
caaagaattt agtccaaagc aaaatttggt gaatagttta gtgattagaa agtaataata    3840
ggttaactac aatatatatg aataagttca agcatagaag taagggattt caatttttga    3900
cctaaaagaa ggaaaatgat gtggatttaa ttttaaccta ttgctcaggt gaacaataga    3960
ttaaccatgc gtggagaata gagttatgat ttatgaaatt gttaagcttc ataattataa    4020
gcaaactttg aacctttttg agctcactga atttgtaact atgagtaaaa atgtattaaa    4080
gaaattaaca acatttgtaa aaaaataata ataacaatgt gagcatacct aagtggtgaa    4140
aagacattta cattgtccta gaaatatggc aggtttgatt gttggcttat attcttagaa    4200
aaagaaaatt aaacatgttt agacgtttca tttctctata agtttgaatt caatcttctg    4260
agggagcatt aatatactga tgggattcta tattccaata ttttcttttg acaggttcgt    4320
tcgttacatt tctttaagac tgtttcttat ccacacacat acacacacta caccaacatg    4380
ttctaaagag tttggaaagt cttggagatt gttcttcaac aaaactacga gattttgtaa    4440
aattacaaca ttaatttgtt aaaatgctca gcacaggaaa ttgatctaaa gagttcgttt    4500
ggcatcagtt tttaagatgt gaaagagtgg ttttgatatt actaaaagaa atgtgctaga    4560
acactctaaa aaataccccaa aaaaacagct gaaattttat aggtattcaa caccttgaaa    4620
aattctctac attttttttt aaaacaaaga atgaagatcg aaaatcacta gtgctcctag    4680
atatcttaac taggttatct ctcaatcttc actgtcctac cccatgcccc aattgcaaaa    4740
atctagtgcc ccaagagata atacaaatga gttcaataga caataagcaa aagctttcaa    4800
agaaaaaaaa actatgtgct tgtgttttat ttatttattt tttgcaagaa tagtattgtg    4860
tgatgttttg gattgatttc aaaattgtta aaacccttttt gttctttgat atggatcata    4920
ttctacgaaa taaaaatctt agggcttccg ctcttcttga aaattttgga caactgtcct    4980
tttgatctga aagttacact tgatatcaat taaaccatgc gggcttaaaa atgatcatat    5040
tctactaaac aatctccatt tcaatcctcg caaaatttaa tagttaattt cattaagatg    5100
gtatgaaatg ggggtggagg gaggatagga gctcatccca gtccggcttc gccgcgtgta    5160
catttctata acccaaatat ttatgatgcc atcaaccttt ttacattgtc aatccaaccc    5220
tatgaatata aatctcacta ttgaatcaca aaccagtttt atcaacaaga agctgccaaa    5280
ctccgagttc agattggtaa cttacagaac tcaaacaggt attttgaagg aaagttattc    5340
gataacattt ccattaatta aaaaatgcaa attttcatct ttcgaagaat gttgttttc    5400 caggaacatg ctaggcgagt ctctaagttc tctgactgca aaagatctga aaggcctgga    5460
gaccaaactt gagaaaggaa ttagtagaat taggtccaaa aaggttggtt ttcatcattg    5520
tttcttaatt atatatttat atatttctat gagaaacaaa ttagttaaca acttttttgtt    5580 tcttgctctc tctctcttcc agaatgaact cctgtttgct gagattgagt atatgcgaaa    5640
aagggtaaac tttcatatcc taatttgact atacttatgc tgttgataac tatatatctt    5700
ctcctaattt ataataatgt attctataca tgtgaataca aaacaaggaa agtgaaagag    5760
ttttgaaatt ctgttgtgaa aatagaaggt ctgaattggg aagtcattag attggctatc    5820
aaaatggaaa attaattcca tggagatgaa accgataatc tattgaagcc taccaataat    5880
gaaacctatt tttctagaaa cttgatgatc aatttcaaac aaaagaaaga aaatttgtga    5940
gtgaaaattc tgatgtgaca atgaagaata ggctgttaat gtgaatatga agaaaaaagg    6000
```

```
gtaccaagaa caagggatca aaaaaaactt ttccttttca accactacgt acgtctggat      6060
cgttagcgct aaacctaagt aattgtttgg tgaaaagaga acaactttc caaataggtt       6120 ggttgaaaaa gtttaaattt cgaatcgggg tttcgttgat tttcttctaa atcatagaaa      6180
gtatatatgt ttttaacgag aaattaaaaa taataacata atgtactttt attagaacgc      6240
cccgaacctg taatccaatt atacacatta tcaaccctct aatccgattg acacatctac      6300
gtctatatta tctgatattt tactcaataa acctgctctc tcatttcgtt gatgttatac      6360
ttggctggta gatttggtct atgttatgag aaagtgattg ttgtttacag gaaattgatt      6420
tgcacaacaa caatcagatg cttcgggcaa aggtttcctt ctttaattaa tttcttcaac      6480
ctctgaatgt tatgagcatt taaaattgaa aactaaagag aataacggtt gcagatagct      6540
gagagtgaaa gaaatgtgaa catgatggga ggagaatttg agctgatgca atctcatccg      6600
tacgatccaa gagacttctt ccaagtgaac ggcttacagc ataatcatca atatccacgc      6660
caagacaaca tggctcttca attagtataa ggttttttgtt tgtttttact gttaaaataa      6720
aaccaaagta aacctctctc tttatataca tacatatata tatctaacca aacacttcgt      6780
tgcagtttat aataaaatgc atggtttgaa gcactctgat tgtggtggat ttggattatg      6840
tataagggag tgcaggccat ttgccaatta ttgaaggta ctcaaacagg aagttgaaga       6900
agttcatcat ctctctcatc tatatgtctt aacaaaagtc ttagcttatg gactctaaaa      6960
caaagactta atttaatata taaatataat tgtgtaatgc tgttgtattg tatggtatgt      7020
atccaaaaac attaataacc tatctttttc ttcaaattat gtctcctttg atacaaaacta    7080 ctaacatatt ttcttatact ttctgtcttt gtcgttactg tttttcactg tctcaacttt     7140
ctcagctgat tcctatttgg attacaagtc ttttgtttct aattatggtt aattattgac     7200
tgattaattc tagagatggg aggataata attaaaaata tggagatttt taattactta      7260
gttaattggc ttcatgttga gttgggaaga gaagaaatta a                         7301
```

<210> SEQ ID NO 26
<211> LENGTH: 5101
<212> TYPE: DNA
<213> ORGANISM: Cucumis sativus

<400> SEQUENCE: 26

```
tattatttca aatcatcata tatcatttta aattaaaaaa attatctcct ctctctaaac       60
ttattatgaa tgaaaagaa acgaaactac ttaccaaaat atatcaaaac atctacaaaa       120
tctttgtaat ttgctacatt ttgtaaataa ttttcggtaa tgaagcttaa aaagagaaa       180 tattattttt caaatgtgga gggtatagta gtaatacacg atggaatcta aaaaggttat      240
ttccaatata taaatgtacc ctaaaaaact ctctctttct atatcgtttc tctcagtttc      300
ctcaggtaat gaattgaatc aaaacatata cttaaaatcc tatttgggta gccaagaaat      360
cgatcaagtt tatattttc ttttgttcat gttttgcagg aaaagaaaaa aaaaatgagt       420
tgttatgagg aagaagatga agaatcagga gtagtaggat taagaagatc atcatcatca     480
tcaagaacag gaagaggaaa gattgaaata aagagaattg aaaatacaac aaatcgtcaa     540
gttactttct gtaaacgaag aaatggtttg cttaagaaag cttatgaact ctctgtcctt     600
tgtgatgctg aggttgctct tatcgtcttc tcctcccgtg gtcgtctcta tgaatacgct     660
aacaacaggt ctcatctctc atctccatat tctccatctc ttgaatgatg tgatattaaa    720
tttattttta ctcatctgtt taaaatttat ggatctggtt taatttacag aaataaaaaa     780
```

```
aattgaagga tcgtttagga ttttaaaaaa attatgtagg atgatcacca tgagagattt    840
aagaatattt tgatgggatt ttaattaata atgttttgaa atgtaaacta taatatttt     900 ttattgttga tctcaaagtt tgatgatgga ttactaataa tccacgtaat taggaaaata    960
aatcataatc aagcaatttg aagagaaatt ttgttcgaaa gtttcacagt tagggtttga    1020
tattcagcat acatcagcga atctttgatt acatcataaa aatggattat ttcgatctgt    1080
tatatgaata tgaactcctg cctttattt ttcttttgtc attattcttt aaatgccttt     1140
tcttaattat cttttttat atataaaatt taaggtttgt tttcatttca ttttgttata     1200
tataaatata taaatttagt tagtgtgtgt gtcactaatg ttataaatta gaattatgaa    1260
acatattcac atatagtaat tttcttttac atgaaaatta tgatttactt aacacattcc    1320
atataattta gtagcccaag gtggaagtta agcattgcat ttaaagcttg aaatcagatt    1380
aaaacctcaa aaacataaaa tgaaacaatc attttgccat tactttttc ttttattaat     1440 tgaaagaaaa aaagaaaaac acatgaaact taaaaataga aataaaacaa agaaagcaat    1500
aatgaagaaa tttgaagcag tgaaaagata ggatgttttg tagaaagatt tgagagagag    1560
ataaaatgag aagctttaag caagcagctg caggtttctg ggcattgcta taataatgaa    1620
aaaacaaaat aaatgcaggt ttgactttca tggattttga ttcaatgacc atattttgaa    1680
gaagagatta ttgaattggt ttatatcatt ttaagataga taatcattaa tatagtaatt    1740
tatagggaac ccaaacgcat agaatttcgt gacacaaaag caaaagtct ctaatgcttc     1800 atttgtcgt taatatctgc ctaataccc attcgtatca caattttaca tttttgttt      1860 ggggaattga agtgttaggg ctacgatttc gaggtacaaa aaggcatatt cggatccctc    1920
caccgccatg accgtttcag aagccaatac tcaggtgatc agctagctct ccattttag    1980 ggtttcattc tgaactctaa attgtgaatc cctccttctc ttctgtttat gtttcagttc    2040
taccagcaag aatctgccaa attacgagct caaatcggaa atttgcaaaa cctaaacagg    2100
taattcatat aaatgaatta gtttatgtgt gtgtatattt gaatttggat ggatgatgat    2160
gataattgtg tgtgtgtgaa tggttggaat taataaaatt taattgaagg catttgttgg    2220
gggaatccat cagttcgtta tcagttaaag atttgaaaag cctagaggtg aaattggaga    2280
aaggaattag ccgaattcga tccagaaagg ttaatattca ttcttaagtc tttaaaacac    2340
atatacataa ttgattaatt aatctagatt ttcattaatg atataaattg ttgttttgt    2400 ttttgttttt gtgttacaga atgagcttct gttttcggag attgaataca tgcaaaaaag    2460
ggtataatca ttttcttctt tttactaatt actttattt aaacacacac acacacatat     2520
atatatttag aagttaaaaa acattcttac ccactaagct taacaattca atttagaatt    2580
tatttctaat cattaggttt agttgcaaaa gttaatttaa agttatcaat tagtaactaa    2640
ttaaaattgt tttttataat taattatggt aaaaaatcta ttttttattta tttatttatt   2700 tgttttttgtt aaattcagtt ttgatatatg tttatagaaa gaaaactcaa aacatatata   2760 atttttatt aataatttaa tgacagacgg tcaatttaag attaaaaaaaa tcacatataa    2820 ttggaaaaca atatttaaat aaaattgaat tagatagccg tgatttctgg ttaatcaata    2880
aacaataatc acttttcacc taatctctct taaatcattc taaaatgatt ttgattatct    2940
caaacatagt catactactt tagctttgtt ttgtaatgat tttacccttg gtactctagc    3000
tttgtttttt taataattta gtttatatgt attttttaatt ttgtaacaat ttaatctatt   3060
ttctttgaaa tttgttcacg ctcttacttt aaaaaattca ataaaattag gtgtcattgt    3120
ttattatttt ataatttata atgttcacta atttataatt gataaaaata ttgaaactct    3180
```

```
aaccttgtta agatgataag gactaaaatt aaaagtacaa gaactaagtt gttacacgtc    3240
aaagtttaat aactaaagtt aaaaatttag agaccaaaag tgactttaa ctttttaaaa    3300 actatataac aaaacctatc aatattcaac ggtgaaaata ttgtatacaa gttcaagttt    3360
aggtagaaaa aaaaaatcaa acacaactta atgcatgttt ttaaaaatta atgtctaaaa    3420
aatatgtgtt tttgtaacta attcttttc ttttagaaaa tacattaata attagaaaag    3480
gtttggttag cgataaaaat atagagtaaa gttgagttga taataattat gaaaagtta    3540 ttaggagagt tgacatgaat gatataaaaa atgagcta aggtgaataa caagttaata    3600
aacctcctta atcattgatg aattgagcat gacgttggtt tgcttttta cccatccaat    3660 cacacgtccc gttagttcgc attaaaataa gagtaagatt caaaatgttt ttttttttc    3720 ttttaaactt catgtactat gaagggaga ttttttaaatt gaaatttat tgattacatg    3780 gacattgttt tgaaagttta acaaaaata gatataatat acataacatt tttaatttac    3840
tctaaatcta aactttcaat ttgaatggtt ataacatttt aaaattgatt attctgaact    3900
cattgttata gtttataact aatttaaaac ttacatgaac ataatatatt aaaatacatg    3960
attgaattaa aagtagaaac aattacaatt gattttgaaa gattacaata aaggattgag    4020
attaaatgta atattatttt gtaataaata taggaaattg aactgcacac taacaaccag    4080
ctgatacgtg caaggtacg gacctctttt caccgttact ctctctatta tattaacata    4140
ttctttctta ttacttaatc caatatatta tcatcaaatt ctaacttctc atctttccca    4200
atcaaaatcc cttaagtttt ttttaaagat tataccatt ttgttttcga gttttaagaa    4260
aaagtatata atctaaggat atctttcttt ttaaaagaa ttattgttct aattaaaatt    4320
ttatttataa ttgtttaaaa tattggagca atttgtagat agccgagaca gagagaagcc    4380
aacaaaacac aaatgcaagt aataacaatg gaatagcaac aagaagagga gaggaaggat    4440
caatgggtac aaatttagag gacaacaatc atcatcaata tgactcaaca aactactttg    4500
atccccatca taatcacct atctctcttc aacttgtgta agtaagtcca tttcttcttt    4560
atatatatat gttttatata tatatatata gataaactat attttaaaaa ggatgggcat    4620
gcatgggcat ataattatta gtaattaagc aatataatgt tggatgtttg tttgttattg    4680 tagcccttg tattttcaa atatatattt tgtgaaaaga atgtgcttca ttttccatgt    4740
ttctatcttc tctatatcat aacatcaaca tatatgtttt gttttggtta tgtgaatgca    4800
atcggatctc tctatattac atattattat atgtcacttt ttctagttta atacattgtt    4860
tttgttaatt aataactctc ctagtttatc gggtgtgttt gggttcattt ttttaaaaaa    4920
atattattca aataactcat ttttatttaa gttatatcga taaaaatggt attaactaaa    4980
cgttaaaatc gatttttcg tgattatcca ttaatctaat ttttttcttt ctaaattata    5040
aaaaaatatc ttaaacttc aaatatttca aaaatgtcct taaaactta aaaaaatgtt    5100 c                                                                   5101
```

<210> SEQ ID NO 27
<211> LENGTH: 9501
<212> TYPE: DNA
<213> ORGANISM: Lycopersicon esculentum

<400> SEQUENCE: 27

```
tgttgaatga tggaatgaaa tacaaactta caaaattttt attattttct actttcagaa      60
atcatttttt ttatttttta ttttacaag aaaagccatt cttattgtt aaattatctt     120
```

```
ccttttttga aaaaaagat attgaccaat ttaacattaa aattacagaa aaacacaatc    180
atgttgcgat aatagaattg cataattctg tcttaattaa gtataaatca gctgactgaa    240
ttctatgtgg aactcaacaa atcaaccta actttcattt caacgtgcgg tttcacaaaa    300
ccctaaaaaa gttaaatctt cactttatct atcaattgac actccataac ggatttagaa    360
ttttaattcc atgagttaag catttctaga tgtttagtat tgagtcaatt atatgtttga    420
agttataatt catgtaactt tgcctatgaa tttatgcttc atcagaagtt atgatttcaa    480
ttaaacttgt atccttccct atagatatga tatgaattta tatcatcgag ttaaattact    540
tcaagtttga cggaaatatt attcttaaat ttcaaacaag ttgatattga ttatatgaat    600
ttttaccatg aattcagaag tagaattaat atctatgttt ttcttaatta aacaaaatta    660
gagcccgttt gaataggttt agtagtcggt caaacctact tttaaatcaa ttttttgactt    720 ctgaaagtgt taggcaaata taaaaagtaa ctaaataag ttacgaagtg tctgacaaag    780 taaaaatga ctcaaaacaa ataaaaaatg atttaaaata agtcaaaaac caaaagtaga    840 tccctatta cttttatttt tttgacttaa aagtcatttc attttgattt tttatttta    900 atttaaaagc tatttttta agccaatcca gacggtctct taatatacag gtcaaacctc    960
attaaataaa atttaaatat ttgaaagaaa agtttgagag attttaaaca gcacaagggg   1020
catattagtc aagaagaaac aaaaataaca cgctttgcaa taattggtga aattttagtc   1080
tgcaataaac aatcccataa catcacgtct ggttatatc tggaaaaaag ccatttgaat   1140 gtcatttct tggccagcca tctctattat ctctcttcac tttaattttg agtgatactt   1200
tcttcgtcca tccgactcaa cacacatctt ttaagaaata ataaattcga agagtaattt   1260
tattatatat catcagtcac ccctattggt aacacgtcat ctaaatatta aaaagtaaat   1320
aaaatggtaa aacatctctt gtgttttca aattgaataa ttattttag tatagtaaac   1380 aagtaaaaat agtcgtagct agggataaag ttagggtaag tagggatata atataaaag   1440 aaagaaaagc atataagtat tatgtttttt cttcattgat cagtgtacaa ataagaagtc   1500
tttggaagtt gtgtgagttt tcagaaagcc tttgaagttc gccggaaaat agcaatattt   1560
tcaattcaag ccaatcaggt ctattacgtt gatatttac atagcatcaa attttagaaa   1620 gaaaaaata tatgaaaaaa cttaaatttc ccattcttcc atgcattttt taaattttt   1680 ttttttgca gattctgaaa tgtttctctc tgtgttcatt atgacaaaat taatttgtgt   1740
ttcgtgtgga actaagtcaa gctttagatc tatctgcaaa ttacataggt tatagaaata   1800
tgaaagattt catttttata tctatcaagc gcgtgcattt tttttttctt ttaatctttc   1860
acttatttga aagggaaggg tgcttactat ctgagtaacc tcctcttgtc acggaaattt   1920
tggttgatca ataaaagatc tccttgaaac atgatgatct tgtgtgtaag ttatgtttac   1980
acaagatttt tttaatttg tgtgtatctt ttcttgcata tcatgaggag aaaaaaagg   2040 aattggaaaa acatttgtac tacttttta ttatatttgg aggtagcttc tcccaagaaa   2100
ataaaaattt aattcttcaa atactaatta atttggatga ttatgtgagt tattattgct   2160
taaattcttg tattggatgg ttgtttttt tttagtgata gagagatttt agaatcattt   2220
ctcaaatctc ttgttttaaa tttcttcttt gtttaatctc tttgaatact tagttctaca   2280
catgcacgac ttttaatatg aggtgtttta gagatacata taacaatttt accagtcgtt   2340
tttaataata ctacttttttt tttttaaaaa aaaaagaca gtctaattg gagcaattct   2400 ccaagaaaga actagtttaa aacattgatt ttgtattata aatttatttt acttcatcat   2460
caaacatgga gttacttctg cttcatcttt cgtttattta gttagaccta actacctctt   2520
```

| | |
|---|---|
| caatttctac tgaatggaag aaaaaaaatg atataagtta ttgcttagat tcttgtattg | 2580 |
| aaagcgtttt cataaattta atcgaaactt taaaattttt tatagaagat gaattgaaga | 2640 |
| atcaatttt ggatttcttt ttggagtata agcgaaattt atccgaaaaa ctgatttggg | 2700 |
| caaattttg gagttagatt tttttttttg aagatggtaa attttcaaga aaagaaaaga | 2760 |
| aaaaaacaaa tctcatgaag aaacggtatt ttaatttttt tagaaaaaat ctatgatcga | 2820 |
| accagagcta attagttcat agatttcttg ttctagattt ctactaattt ttctcttgtt | 2880 |
| atagaatgag atatgtccga tttattcatt actctcaaaa ttaaaacata ggtattaatt | 2940 |
| aattaaatat aaatgtgtta tattctcttt tatgtggtta atacagatgg gaagaggaaa | 3000 |
| gatagagata aagaggatag agaacaacac aaacaggcag gttacatttt gcaagagaag | 3060 |
| aaatggattg ttgaagaaag cctatgaact ctctgttcta tgtgaagctg agattgctct | 3120 |
| tattgtttc tccacacgtg gacgcgtcta tgaatactct aacaacaagt aatttcttat | 3180 |
| ttatctctca tatagttaaa tttgttcaat tagacgatca tatatatcgt tatataacat | 3240 |
| ataatatatg gacataatat ggcatttcat tagcatctac ttctttcttg atatcataat | 3300 |
| cattcgctta tctcttgatg tttgaaatct gaataatcat tttgttagtg cataaaataa | 3360 |
| ttgagctgta agaaagcata tatgaataca ctgttcctca aaatttatag tagttgtttg | 3420 |
| attcacacac aaatgacaga atcggaggtg gaggatactt acaatcaact cttctcgtct | 3480 |
| ttaattgtgt ttgagttata tgtaaaaaat attatcataa aaggatttac atataataat | 3540 |
| ctagataaat aatactatga aaggtttgag gatagataac ataatcaata tagaatgtta | 3600 |
| tttgtgaaac ttattgtcct tactttcact agaaaattag tctatttttc tcaatttaa | 3660 |
| gaaatttgtt ttttttttg aaaaaaaaat tattctaaaa ttttggctaa ccaaaatgga | 3720 |
| gaagataaaa aaaaaaagt aaaatagaaa atattttccc ccatatcgaa aatatcctat | 3780 |
| atatccaaca ccgtacctaa gtcacaaaag atcaataaga aaagtgatct tgagcctaac | 3840 |
| tttatcttcg aaggtttgct tatgaggtaa aaattataat aagaaaagtg atttgaggca | 3900 |
| taattaactc tacttcaaaa cttagttcat gaggtaaaaa ctatccaaaa tcatatagga | 3960 |
| agacacatcg gtcattaacc atcaatatga gatactaata ttttcgtac aattagtcct | 4020 |
| gtcaactaaa gcgtgaacaa tataatataa agatccaacg tcaaaataag ttaagaaatg | 4080 |
| agatgaatat aaatttacta tctcttaatc acaattaaaa aaaggaaggc attctcaggt | 4140 |
| gatatcgaat aatagtacac tagtgttta ggagatgttc acacatatag tttaacttag | 4200 |
| ttgaatctct acccaatcct cgagccctct gtcgaagctt agttaataat tcaatctcaa | 4260 |
| ttgctagttc atgagaatga gatctgccaa aagttaaacc atcttagaag attaataatt | 4320 |
| gccactttgt tttgaatttt gaataacaca aattttctt ttaaaaaaaa aaaaatatta | 4380 |
| ataaaaaaaa tttgccacat ccatcaccag cctgtgaaat aattaaagtg aaatgaaata | 4440 |
| tcctctcgcg ataaactttt acatgagatg atttatactt caatataatt atagtataat | 4500 |
| agtaccaaag ctataggtat aagtcttgag tttgaatcgt acagtaacta actcatcatc | 4560 |
| atcaattaaa aacgaatttt tcacgtgctt ggccgtacat attctctctc taacttcttt | 4620 |
| aaattcttaa ataagatggt ttatgcactt caaacaacta tgataattac cttgaaagat | 4680 |
| ccatgtgtga gtatatatat atatatat gcaagaaaag tgaatgagtg acaaataata | 4740 |
| tttattggtt ttatacatga aaaagtgtca aggcacactcc agattaataa gtactaaaag | 4800 |
| aagtatatat tgagaagtcc catcatgagt gacttgtgac tattgtgttc tgctgttatg | 4860 |

```
agggcctttt tgtttcctct tgtagcttat gcattataaa gttctcctgc tttggtttgt    4920
atctattcta gttctagtca atatatgttc tctctttcac ttttatgtct acatatatta    4980
attaattaaa aaagtacttc tcccatatat aaggtctccc tattgcatgc atatggaata    5040
ttaaaaaaaa ataaaaaaag tacatattat tatcacccta aaatgtaaaa aagatatgat    5100
tccaaagata gtgcaacata aaaggagaga agagaaatct tcaaaaatta catcatcaca    5160
aattagattt tcttatcaat gtttttttt ttaatctgca ctctgatgag taaatcattc    5220
tcttgctttt agttgtttcc attgctagct tttggtttca ttgaacatga tcttttatg    5280 caacacaaag tactacctat ctttgtacta atttatattg cattgtttga atttcaaaag    5340
agtcagttta aatagtaaga ccgaatacaa acatataaaa agtgtttat aataaaattt     5400 acatatttaa aaattagata aaaaatatga taagtcgtaa taattaactt tgtggataga    5460
gatggctcat taaaggttta atgcaatggc ttgttttaat tgaccacctg aaaatatata    5520
ttataaaaaa atattcttat tagacacttc ccgtttaaat ttagaaaatg acttttgggc    5580
atgtgtgttc tcaagtacct tgactactta aaatatgtat caccttattt ttaattatat    5640
acattagcct cgaatattta ttgtttataa agtatatgat aaaactttg gtatacacag     5700 cattaaggca actattgaac gatacaagaa ggcaactgct gaaacctcta atgcttgcac    5760
cactcaagag ctcaatgctc aggtaattag ttaagcaaaa tcatttaact ttttgatgct    5820
aaacaataaa aattcatcat taattctatt tcgggatgga ttataaaaaa aaaacaaatt    5880
attagctata tgacaaaata ttgttttggc tgtcatgtat gtagtttat caacaagaat     5940 caaaaaagct gcgccaacag atacaaatga tgcagaattc aaacaggtaa caccataatt    6000
aattcaataa attaaatttg ggatgaattt taaaactaat tcgattatat gcacaaaata    6060
ttttatatat tccacgtgta ggcatctggt tggtgaagga ttaagttgtt tgaacgtaag    6120
agagctgaag cagttggaaa atagacttga acgaggcatc agcagaatca gatcaaaaaa    6180
ggtatatttg taatggttgg attactaaaa tattgttgta agtgcatact attgcattgt    6240
ttggagttgt aaaccaaaca catttttcct tagaagttac tcgcgctttg aaattacgcg    6300
ttatgataaa attatttcat aaaaatatga ctcggaaagt ttgtttcaag ccatttggat    6360
ctgctcacat atagtacaag gccctaaatg agtaatagga aaccttgcac ttttttttt    6420 gataagtgtc atatagagaa aggaaacaaa aactttgata ttattttgt ttggtaatta    6480 aatgaattat aagaaaacaa atgaattaat tgaaacttga taagagttag acaacattga    6540
ttatgatcca tttttagtc catcgtgatc caacttgtga cagataatcg atatacgatc    6600
cgttcattta ttaacttaac tcactttaat tttgatctgt ccatctgaca acattacatg    6660
tagtgaaaat gtcagcctaa gtagcaaaat ttttatgtt gattatacaa atcctcataa    6720
cagtagcttt gatgtttgtt atgtggttga acagcatgag atgatactgg ctgaaactga    6780
gaatttgcag aagagggtaa taatttattg aaaaattgtt tttatccttt ttatgtttta    6840
ggttcagact aaatataatt atgctttggc atattttata atctttcaac ttgctgtttt    6900
aataggaaat tctactggaa caggagaatg cattccttag atcaaaggta cttaattagt    6960
agcacacatt tcttttaaat tggttactta gaaaagaat acatttttaat atttatagat    7020 agacattaac atcgataatc acttaatctt gttagtatat ttttttagac ccttgaacta    7080
tggtctattc cacttaagca acggaacacg ataaagtgtt cctaattata agaaacttct    7140
ggtttaactt tttgacagat gtttgcgcgt gttcttaatt atatattagg tattaactaa    7200
tcacaaaata tgtcatttca ttttaattat tcacatcgac ctcaattaaa acatgcatgc    7260
```

```
ttaagacttt gttacttatt gaggctaatg catgtaatct aagcaagcga tgacactttt    7320
taagcgatca ccttctccat gtaattgact cttagaatat tccgaaaagt tattaaagtg    7380
ccaaatagaa acactttatc atatgtttag gcgctcaatt agaataaaac aagcaaaagt    7440
ttgtttaaat gaaactgacg tacactttaa tccccaaaaa ttgcaaattt tcatttagtt    7500
actttattat tagtacttta tttttaaaag agaatccggg aggggattat aaggtggaaa    7560
aacaaactct taccaataag gtgagagtta agataacgaa ccatctggct agctacgtac    7620
taagattccc atttagttat tttctctcat ggagattaat gaaaatatta ttgctttcag    7680
atagcagaaa atgagaggct tcaggaacta agcatgatgc cagcagcagg aggacaagat    7740
tacagtgcaa tacagcaata tttagcaaga aatatgcttc aacttaatat gatggaaggc    7800
caaggagtct cttcctatga tccattgcct cctcctcatc atgacaagaa gtcccttgaa    7860
cttcagtaga gtatgtagtc ttcacttcct caaacaaata tctttatatt gtcactatta    7920
attttttagt tcaagttata tacactgtta gagtaattaa gtaaagtttt gtactatcca    7980
taagtcacat ctacatgtca tagcaaataa cctatcttac tttcgagatt ccaaatatca    8040
caatacaagt agtatcattt aggtgaaaaa gcccacaatt tgagccaaga gtctttcaaa    8100
gacagtctct ctatctctat gaggtagggt taagatttgc gtacactcta ctctctccag    8160
gatttcaccg gatatgttct tattgcagat actgtaaaag atttacacca atggtatata    8220
taacttgaac cttttgttg caaaactaag ctcaaaatgt atgtttgaac gtaccgattt    8280
ctccactgat gattcgtgtt tcttttgatg cagataaaat ccccagcaag aggtttgaga    8340
attttacaaa agaacttta atgtctacaa cctatcaagt aatctctaat gactgtatgt    8400
tgcttaaatt agtaccttat tttgtgtatt tgaattgttt gttttgggat ttgtaagaaa    8460
tttgaactta tgatgagctt agagagtatg ttgaagttca ctttctatta gtctttgaga    8520
aactatagcc ctcaaagtca atagaaatag gattgataaa ccagcaaatc cgacttatta    8580
ggaatgagta catatatact ttctgaagac aatcgcgaat acagaaaatt tataaaacag    8640
aagtaacaaa atcagttaat tatgaggaac aaaagatgtt ataacgtgaa atgaaagtag    8700
caatacggat ggttgataat tctgatggaa agttaggtag tgcgaaagct cagaaacgga    8760
gaaaaaatac ttgcatcaaa gtactaacat ataaaataaa aaagactctg gttatgagtt    8820
accaattgtc tttaacaatt ttgcatagct cgagtacgaa tttcccttcc ttgtacttct    8880
gcgatggctc aacagttctt tcatacttcc agcccaatac ctcgttgcaa tccacacagt    8940
gtatgtcagc aattgtgtgg agaccagttg tgagacgttt ttgttcatag gttccaacaa    9000
caacatttct cacatgagca aaaggaaag ccttgctatt ctttgactga aaaacagata    9060
ataatttttt ctacagttaa tggacagaaa ccagacgatc acagataaag tgcacgacaa    9120
taccaatcta gtaactatac atgggcagat gaaatcgttc acctggaagt tggtagagat    9180
gatatcatcg tgaaatgaga catgtcttcg acatttgtag cagctgtaag agcgagtttt    9240
gactaattca tccatccaac aaaaccgtaa cacgaaagtt aatactttac accaggacaa    9300
ctggatacaa ggagtaagcc aaacttagaa ggaaatgaga acgatccaga aatctgtact    9360
agtttaaact tacaaaatta catcaacaac taatagaata gatactgacc tgtgagctcc    9420
tcagtctctc tttgagcttt ctctaagcta tctttcaatt cacgaatttc ttttttctgcc    9480 tctaaacgag cagtacgctc t                                              9501
```

<210> SEQ ID NO 28

```
<211> LENGTH: 22
<212> TYPE: DNA
<213> ORGANISM: Lycopersicon esculentum

<400> SEQUENCE: 28
ttgacttctg aaagtgttag gc                                                  22

<210> SEQ ID NO 29
<211> LENGTH: 20
<212> TYPE: DNA
<213> ORGANISM: Lycopersicon esculentum

<400> SEQUENCE: 29 attgctatttt tccggcgaac                                                    20

<210> SEQ ID NO 30
<211> LENGTH: 139
<212> TYPE: PRT
<213> ORGANISM: Artificial Sequence
<220> FEATURE:
<223> OTHER INFORMATION: Consensus sequence of FIG 2

<400> SEQUENCE: 30

Met Arg Met Ile Lys Glu Glu Gly Lys Gly Lys Leu Gln Ile Lys Gly
1               5                   10                  15

Glu Val Gly Leu Arg Ser Gly Arg Gly Lys Ile Glu Ile Lys Arg
            20                  25                  30

Ile Glu Asn Thr Asn Arg Gln Val Thr Phe Cys Lys Arg Arg Asn Gly
        35                  40                  45

Leu Leu Lys Lys Ala Tyr Glu Leu Ser Val Leu Cys Ala Glu Ala Leu
    50                  55                  60

Ile Val Phe Ser Arg Gly Arg Tyr Glu Tyr Asn Asn Thr Ile Arg Tyr
65                  70                  75                  80

Lys Lys Ala Ser Leu Glu Asn Gln Tyr Gln Gln Glu Lys Leu Gln Ile
                85                  90                  95

Asn Asn Ser Asn Leu Val Arg Gly Ser Leu Leu Lys Leu Glu Leu Glu
            100                 105                 110

Gly Arg Lys Glu Glu Glu Arg Glu Leu Asn Arg Ile Ala Glu Glu Arg
        115                 120                 125

Gln Glu Gly Ser Pro Leu Pro Pro Leu Leu
    130                 135
```